United States Patent
Achiron et al.

(10) Patent No.: US 9,758,831 B2
(45) Date of Patent: Sep. 12, 2017

(54) METHODS OF PREDICTING CLINICAL COURSE AND TREATING MULTIPLE SCLEROSIS

(71) Applicant: Tel HaShomer Medical Research Infrastructure and Services Ltd., Ramat-Gan (IL)

(72) Inventors: Anat Achiron, Tel-Aviv (IL); Michael Gurevich, Rechovot (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 0 days.

(21) Appl. No.: 14/703,942

(22) Filed: May 5, 2015

(65) Prior Publication Data

US 2015/0315646 A1    Nov. 5, 2015

Related U.S. Application Data

(62) Division of application No. 13/260,573, filed as application No. PCT/IB2010/051344 on Mar. 28, 2010, now abandoned.

(60) Provisional application No. 61/202,703, filed on Mar. 30, 2009.

(51) Int. Cl.
| | | |
|---|---|---|
| C12N 15/11 | (2006.01) | |
| C12N 15/12 | (2006.01) | |
| C12Q 1/68  | (2006.01) | |

(52) U.S. Cl.
CPC ..... *C12Q 1/6883* (2013.01); *C12Q 2600/106* (2013.01); *C12Q 2600/112* (2013.01); *C12Q 2600/136* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

| | | | | |
|---|---|---|---|---|
| 2004/0143110 A1* | 7/2004 | Krolewski | ............ | C07K 14/47 536/23.2 |
| 2008/0280779 A1* | 11/2008 | Shaughnessy, Jr. | . | C12Q 1/6809 506/10 |
| 2012/0020954 A1 | 1/2012 | Achiron et al. | | |

FOREIGN PATENT DOCUMENTS

| | | |
|---|---|---|
| CA | 2610057 | 5/2008 |
| EP | 0983256 | 3/2000 |
| IL | 199523 | 6/2009 |
| WO | WO 98/52933 | 11/1998 |
| WO | WO 03/081201 | 10/2003 |
| WO | WO 2005/108610 | 11/2005 |
| WO | WO 2007/090280 | 8/2007 |
| WO | WO 2008/081435 | 7/2008 |
| WO | WO 2010/113096 | 10/2010 |

OTHER PUBLICATIONS

Invitation Pursuant to Article 94(3) and Rule 71(1) EPC Dated Dec. 14, 2015 From the European Patent Office Re. Application No. 10713522.0.
Office Action Dated Feb. 11, 2016 From the Israel Patent Office Re. Application No. 215392 and Its Translation Into English.
Communication Pursuant to Article 94(3) EPC Dated Aug. 5, 2014 From the European Patent Office Re. Application No. 10713522.0.
Communication Pursuant to Article 94(3) EPC Dated Jan. 17, 2013 From the European Patent Office Re. Application No. 10713522.0.
Communication Pursuant to Article 94(3) EPC Dated Mar. 17, 2014 From the European Patent Office Re. Application No. 10713522.0.
International Preliminary Report on Patentability Dated Oct. 13, 2011 From the International Bureau of WIPO Re. Application No. PCT/IB2010/051344.
International Search Report and the Written Opinion Dated Jun. 18, 2010 From the International Searching Authority Re. Application No. PCT/IB2010/051344.
Notice of Non-Compliant Amendment Dated Nov. 21, 2011 From the US Patent and Trademark Office Re. U.S. Appl. No. 13/260,573.
Office Action Dated Feb. 18, 2013 From the Israel Patent Office Re. Application No. 215392 and Its Translation Into English.
Office Action Dated May 22, 2014 From the Israel Patent Office Re. Application No. 215392 and Its Translation Into English.
Office Action Dated Oct. 23, 2013 From the Israel Patent Office Re. Application No. 215392 and Its Translation Into English.
Official Action Dated Feb. 12, 2015 From the US Patent and Trademark Office Re. U.S. Appl. No. 13/260,573.
Official Action Dated Oct. 22, 2013 From the US Patent and Trademark Office Re. U.S. Appl. No. 13/260,573.
Official Action Dated Aug. 26, 2014 From the US Patent and Trademark Office Re. U.S. Appl. No. 13/260,573.
Restriction Official Action Dated Jul. 18, 2013 From the US Patent and Trademark Office Re. U.S. Appl. No. 13/260,573.
Achiron et al. Zinc-Ion Binding and Cytokine Activity Regulation Pathways Predicts Outcome in Relapsing-Remitting Multiple Sclerosis, Clinical and Experimental Immunology, XP002480403, 149(2): 235-242, Aug. 1, 2007. p. 238, r-h Col., § 1, 2.
Affymetrix "GeneChip® Human Genome U133 Arrays. The Most Comprehensive Coverage of the Human Genome in Two Flexible Formats: Single-Array Cartridges and Multi-Array Plates", Datasheet Affymetrix, XP007921348, p. 1-8, p. 1-8, Jan. 1, 2003.

(Continued)

*Primary Examiner* — James Martinell

(57) ABSTRACT

Provided are methods and kits for classifying a subject as being more likely to have benign multiple sclerosis (BMS) or as being more likely to have typical relapsing remitting multiple sclerosis (RRMS). Classification of multiple sclerosis disease course is performed by comparing a level of expression of at least one gene involved in the RNA polymerase I pathway in a cell of the subject to a reference expression data of said at least one gene obtained from a cell of at least one subject pre-diagnosed as having BMS and/or from a cell of at least one subject pre-diagnosed as having typical RRMS, thereby classifying the subject as being more likely to have BMS or as being more likely to have typical RRMS. Also provided are methods of diagnosing and treating multiple sclerosis and methods of monitoring treatment efficiency.

4 Claims, 2 Drawing Sheets
(2 of 2 Drawing Sheet(s) Filed in Color)

(56) References Cited

OTHER PUBLICATIONS

Bouwmeester et al. "A Physical and Functional Map of the Human TNF-Alpha/NF-KB Signal Transduction Pathway", Nature Cell Biology, 6(2): 97-105, Feb. 2004.
Cavanaugh et al. "Rrn3 Phosphorylation Is a Regulatory Checkpoint for Ribosome Biogenesis", Journal of Biological Chemistry, 277(30): 27423-27432, 2002.
Costelloe et al. "Long-Term Clinical Relevance of Criteria for Designating Multiple Sclerosis as Benign After 10 Years of Disease", Journal of Neurology, Neurosurgery & Psychiatry, 79(11): 1245-1248, 2008. Abstract.
Gurevich et al. "Prediction of Acute Multiple Sclerosis Relapses by Transcription Levels of Peripheral Blood Cells", BMC Medical Genomics, 2(46): 1-14, Jul. 22, 2009.
Hirschler-Laszkiewicz et al. "Rrn3 Becomes Inactivated in the Process of Ribosomal DNA Transcription", Journal of Biological Chemistry, 278(21): 18953-18959, 2003.
Hong et al. Gene Expression Profiling of Relevant Biomarkers for Treatment Evaluation in Multiple Sclerosis, Journal of Neuroimmunology, XP002566863, 152(1-2): 126-139, Jul. 1, 2004. § [03.2]-[03.3], Fig.4, Tables 5, 6.
Leuenroth et al. "Triptolide-Induced Transcriptional Arrest Is Associated With Changes in Nuclear Substructure", Cancer Research, 68(13):5257-5266, 2008.
Liu et al. "Triptolide, A Component of Chinese Herbal Medicine, Modulates the Functional Phenotype of Dendritic Cells", Transplantation, 84(11): 1517-1526, 2007. Abstract.
Miller et al. "HRRN3 Is Essential in the SL1-Mediated Recruitment of RNA Polymerase I to rRNA Gene Promoters", The EMBO Journal , 20(6): 1373-1382, 2001.
Mootha et al. "Identification of a Gene Causing Human Cytochrome C Oxidase Deficiency by Integrative Genomics", Proc. Natl. Acad. Sci. USA, 100: 605-610, Jan. 21, 2003.
Pittock "Benign Multiple Sclerosis: A Distinct Clinical Entity With Therapeutic Implications", Current Topics in Microbiology and Immunology, 318: 1-17, 2008. Abstract.
Wang "Triptolide Modulates T-Cell Inflammatory Responses and Ameliorates Experimental Autoimmune Encephalomyelitis", Journal of Neuroscience Research, XP002585665, 86(11): 2441-2449, Aug. 2008.
Invitation Pursuant to Article 94(3) and Rule 71(1) EPC Dated Aug. 12, 2016 From the European Patent Office Re. Application No. 10713522.0.
Office Action Dated Aug. 11, 2016 From the Israel Patent Office Re. Application No. 215392 and Its Translation Into English.

* cited by examiner

METHODS OF PREDICTING CLINICAL COURSE AND TREATING MULTIPLE SCLEROSIS

RELATED APPLICATIONS

This application is a division of U.S. patent application Ser. No. 13/260,573 filed on Sep. 27, 2011, which is a National Phase of PCT Patent Application No. PCT/IB2010/051344 having International filing date of Mar. 28, 2010, which claims the benefit of priority of U.S. Provisional Patent Application No. 61/202,703 filed on Mar. 30, 2009. The contents of the above applications are all incorporated herein by reference.

SEQUENCE LISTING STATEMENT

The ASCII file, entitled 62191SequenceListing.txt, created on Sep. 27, 2011, comprising 7,168,844 bytes, submitted concurrently with the filing of this application is incorporated herein by reference.

FIELD AND BACKGROUND OF THE INVENTION

The present invention, in some embodiments thereof, relates to methods of classifying a subject as having benign multiple sclerosis or typical relapsing remitting multiple sclerosis and, more particularly, but not exclusively, to methods of treating multiple sclerosis based on same.

Multiple sclerosis (MS) is the most common demyelinating disease of the central nervous system (CNS) affecting young adults (disease onset between 20 to 40 years of age) and is the third leading cause for disability after trauma and rheumatic diseases, with an estimated annual cost 34,000 USD per patient (total life time cost of 2.2 million USD per patient).

The disease is characterized by destruction of myelin, associated with death of oligodendrocytes and axonal loss. The main pathologic finding in MS is the presence of infiltrating mononuclear cells, predominantly T lymphocytes and macrophages, which surpass the blood brain barrier and induce an active inflammation within the brain and spinal cord. The neurological symptoms that characterize MS include complete or partial vision loss, diplopia, sensory symptoms, motor weakness that can worsen to complete paralysis, bladder dysfunction and cognitive deficits, which eventually may lead to a significant disability. The associated multiple inflammatory foci lead to myelin destruction, plaques of demyelination, gliosis and axonal loss within the brain and spinal cord and are the reasons contribute to the clinical manifestations of neurological disability.

The etiology of MS is not fully understood. The disease develops in genetically predisposed subjects exposed to yet undefined environmental factors and the pathogenesis involves autoimmune mechanisms associated with autoreactive T cells against myelin antigens. It is well established that not one dominant gene determines genetic susceptibility to develop MS, but rather many genes, each with different influence, are involved.

Clinically, in 85% of MS patients the illness is initiated with a relapsing-remitting course (RRMS), and in about 10-15% of MS patients have an a-priori primary progressive course (PPMS) without relapses. RRMS is characterized by inflammatory attacks associated with neurological deficits with periods of remissions between the relapses that vary in time. After a period of 10 years, about 50% of RRMS patients will progress to a secondary progressive MS (SPMS) course, characterized by permanent neurological dysfunction, with or without relapses and progressive disability.

Benign M S (BMS) is a clinical variant of RRMS in which the patients develop low neurological disability if at all after a disease duration of at least 10 years. Accordingly, this group of MS patients do not experience devastating accumulating disability over-time and when these patients are examined neurologically and scored by the Expanded Disability Status Scale (EDSS) they receive a score that is equal to or lower than 3.0. This low EDSS score signifies mild disability and when this low disability occurs more than 10 years after disease onset, the course of MS is defined as benign (Pittock S J and Rodriguez M, 2008; Costelloe, L., et al., 2008). Prediction of patients that will have BMS is currently impossible and the definition of these patients is retrospective. The molecular events accountable for the BMS variant of disease are not understood.

Diterpenoid triepoxide Triptolide (TPT), isolated from the Chinese herb *Tripterygium wilfordii* (Leuenroth S J and Crews C M. Triptolide-induced transcriptional arrest is associated with changes in nuclear substructure. Cancer Res. 2008; 68:5257-5266) has various anti-inflammatory effects (Liu Y, et al. Triptolide, a component of Chinese herbal medicine, modulates the functional phenotype of dendritic cells. Transplantation. 2007; 84:1517-1526), it modulates T-cell inflammatory responses and ameliorates Experimental Autoimmune Encephalomyelitis (Wang Y, et al. Triptolide modulates T-cell inflammatory responses and ameliorates experimental autoimmune encephalomyelitis. J Neurosci Res. 2008; 86:2441-2449). Derivatives of TPT were suggested for treating autoimmune diseases (EP 0983256, PCT/US1998/008562; WO9852933A1).

Cycloheximide, inhibits the phosphorylation of RRN3 and causes its dissociation from RNA polymerase I. RRN3 interacts with the rpa43 subunit of RNA polymerase I, and treatment with cycloheximide inhibits the formation of a RRN3/rpa43 complex in vivo (Alice H. Cavanaugh, et al., 2002. Rrn3 Phosphorylation is a regulatory checkpoint for ribosome biogenesis J. Biol. Chem., 2002; 277: 27423-27432).

PCT Application No. PCT/IL2007/32856 discloses methods and kits for predicting prognosis of multiple sclerosis.

PCT Application No. PCT/IL2007/001617 discloses methods and kits for predicting the prognosis of a subject diagnosed with multiple sclerosis and methods of selecting a treatment regimen of a subject diagnosed with multiple sclerosis.

Achiron A, et al., 2007 (Clinical and Experimental Immunology, 149: 235-242) describe genes of the zinc-ion binding and cytokine activity regulation pathways which predict outcome in relapsing—remitting multiple sclerosis.

Additional background art includes PCT Pub. No. WO03081201A2.

SUMMARY OF THE INVENTION

According to an aspect of some embodiments of the present invention there is provided a method of classifying a subject as being more likely to have benign multiple sclerosis (BMS) or as being more likely to have typical relapsing remitting multiple sclerosis (RRMS), the method comprising comparing a level of expression of at least one gene involved in the RNA polymerase I pathway in a cell of the subject to a reference expression data of the at least one gene obtained from a cell of at least one subject pre-diagnosed as having BMS and/or from a cell of at least one subject pre-diagnosed as having typical RRMS, thereby classifying the subject as being more likely to have BMS or as being more likely to have typical RRMS.

According to an aspect of some embodiments of the present invention there is provided a method of diagnosing a subject pre-diagnosed with multiple sclerosis (MS) as having benign multiple sclerosis (BMS) or typical relapsing remitting multiple sclerosis (RRMS), the method comprising:

(a) classifying the subject as being more likely to have BMS or as being more likely to have typical RRMS according to the method of the present invention, (i) wherein when the subject is classified as being more likely to have the BMS then the subject is diagnosed as having BMS;

(ii) wherein when the subject is classified as being more likely to have the typical RRMS, then the subject is diagnosed as having typical RRMS; and (c) informing the subject of the diagnosis, thereby diagnosing the subject pre-diagnosed with the MS as having the BMS or the typical RRMS.

According to an aspect of some embodiments of the present invention there is provided a method of monitoring an efficiency of an anti multiple sclerosis (MS) drug in treating a subject diagnosed with a typical relapsing remitting multiple sclerosis (RRMS) course, the method comprising:

(a) treating the subject with the anti MS drug; and (b) comparing a level of expression of least one gene involved in the RNA polymerase I pathway in a cell of the subject following the treating with the anti MS drug to a level of expression of the at least one gene in a cell of the subject prior to the treating the subject with the anti MS drug, (i) wherein a decrease above a predetermined threshold in the level of expression of the at least one gene following the treating with the anti MS drug relative to the level of expression of the at least one gene prior to the treating with the anti MS drug indicates that the anti MS drug is efficient for treating the subject;

(ii) wherein an increase above a predetermined threshold in the level of expression of the at least one gene following the treating with the anti MS drug relative to the level of expression of the at least one gene prior to the treating with the anti MS drug indicates that the anti MS drug is not efficient for treating the subject; or (iii) wherein when a level of expression of the at least one gene following the treating with the anti MS drug is identical or changed below a predetermined threshold as compared to prior to the treating with the anti MS drug then the treatment is not efficient for treating the subject.

thereby monitoring the efficiency of the anti multiple sclerosis (MS) drug in treating the subject diagnosed with the typical RRMS course.

According to an aspect of some embodiments of the present invention there is provided an in vitro method of predicting an efficiency of an anti multiple sclerosis (MS) drug for treatment of a subject diagnosed with a typical relapsing remitting multiple sclerosis (RRMS), the method comprising:

(a) contacting cells of the subject with a therapeutically effective amount of the anti MS drug; and (b) comparing a level of expression in the cells of at least one gene involved in the RNA polymerase I pathway following the contacting with the anti MS drug to a level of expression of the at least one gene in the cells prior to the contacting with the anti MS drug, (i) wherein a decrease above a predetermined threshold in the level of expression of the at least one gene following the contacting with the anti MS drug relative to the level of expression of the at least one gene prior to the contacting with the anti MS drug indicates that the treatment is efficient for treating the subject;

(ii) wherein an increase above a predetermined threshold in the level of expression of the at least one gene following the contacting with the anti MS drug relative to the level of expression of the at least one gene prior to the contacting with the anti MS drug indicates that the treatment is not efficient for treating the subject; or (iii) wherein when a level of expression of the at least one gene following the contacting with the anti MS drug is identical or changed below a predetermined threshold as compared to prior to the contacting with the anti MS drug then the treatment is not efficient for treating the subject.

thereby predicting the efficiency of the anti MS drug for treatment of the subject diagnosed with the typical RRMS.

According to an aspect of some embodiments of the present invention there is provided a method of treating a subject diagnosed with multiple sclerosis, the method comprising (a) classifying the subject as being more likely to have BMS or typical RRMS according to the method of the present invention, (b) selecting a treatment regimen based on classification results of step (a); thereby treating the subject diagnosed with multiple sclerosis.

According to an aspect of some embodiments of the present invention there is provided a method of treating a subject diagnosed with multiple sclerosis, the method comprising:

(a) diagnosing a typical relapsing remitting multiple sclerosis (RRMS) according to the method of the present invention, (b) administering to the subject a therapeutically effective amount of diterpenoid triepoxide Triptolide (TPT) or a derivative thereof, thereby treating the subject.

According to an aspect of some embodiments of the present invention there is provided a probeset comprising a plurality of oligonucleotides and no more than 50 oligonucleotides, wherein an oligonucleotide of the plurality of oligonucleotides specifically recognizes a polynucleotide of at least one gene involved in the RNA polymerase pathway.

According to an aspect of some embodiments of the present invention there is provided a kit for classifying a disease course in a subject diagnosed with multiple sclerosis (MS), comprising the probeset of the present invention.

According to an aspect of some embodiments of the present invention there is provided a method of selecting a drug for treating a typical relapsing remitting multiple sclerosis (RRMS) in a subject, the method comprising:

contacting cells of a subject classified as having a typical RRMS with a plurality of drug molecules, identifying at least one drug molecule which downregulates a level of expression of at least one gene involved in the RNA polymerase I pathway, the at least one drug molecule is suitable for treating the typical RRMS in the subject, thereby selecting the drug for treating the typical RRMS in the subject.

According to some embodiments of the invention, a decrease above a predetermined threshold in the level of expression of the at least one gene in the cell of the subject relative to the reference expression data of the at least one gene obtained from the at least one subject having the typical RRMS classifies the subject as being more likely to have the BMS.

According to some embodiments of the invention, an increase above a predetermined threshold in the level of expression of the at least one gene in the cell of the subject relative to the reference expression data of the at least one gene obtained from the at least one subject having the BMS classifies the subject as being more likely to have the typical RRMS.

According to some embodiments of the invention, a level of expression of the at least one gene in the cell of the subject is identical or changed below a predetermined threshold as compared to the reference expression data of the at least one gene obtained from the at least one subject having the BMS, then the subject is classified as being more likely to have the BMS.

According to some embodiments of the invention, a level of expression of the at least one gene in the cell of the subject is identical or changed below a predetermined threshold as compared to the reference expression data of the at least one gene obtained from the at least one subject having the typical RRMS, then the subject is classified as being more likely to have the typical RRMS.

According to some embodiments of the invention, when the subject being more likely to have typical RRMS then the treatment regimen comprises administering to the subject an agent which downregulates the level of expression of the at least one gene involved in the RNA polymerase I pathway.

According to some embodiments of the invention, the at least one gene involved in the RNA polymerase 1 pathway is selected from the group consisting of POLR1D, LRPPRC, RRN3 and NCL.

According to some embodiments of the invention, the at least one gene involved in the RNA polymerase 1 pathway comprises the POLR1D, LRPPRC, RRN3 and NCL genes.

According to some embodiments of the invention, the agent is selected from the group consisting of an siRNA, an antisense, an antibody and a small molecule.

According to some embodiments of the invention, the small molecule is Cycloheximide According to some embodiments of the invention, the at least one gene is RRN3, and whereas the downregulating is effected using diterpenoid triepoxide Triptolide (TPT) or a derivative thereof.

According to some embodiments of the invention, the at least one gene is RRN3, and whereas the downregulating is effected using Cycloheximide According to some embodiments of the invention, the kit further comprising a positive control for an expression level of the at least one gene involved in the RNA polymerase pathway.

According to some embodiments of the invention, each of the plurality of oligonucleotides is bound to a solid support.

According to some embodiments of the invention, the plurality of oligonucleotides are bound to the solid support in an addressable location.

According to some embodiments of the invention, the level of expression is determined using an RNA detection method.

According to some embodiments of the invention, the level of expression is determined using a protein detection method.

According to some embodiments of the invention, the cell is a blood cell.

According to some embodiments of the invention, the method further comprising administering to the subject a therapeutically effective amount of an anti MS agent.

According to some embodiments of the invention, the anti-MS agent is selected from the group consisting of Diterpenoid triepoxide Triptolide (TPT), Adderall, Ambien, Avonex, Baclofen, Beta interferon, Betaseron, Celexa, Clonazepam, Copaxone, Corticosteroids, Cymbalta, Cytoxan, Dexamethasone, Effexor, Elavil, Gabapentin, Hydrocodone, Lexapro, Lyrica, Mitoxantrone, Naltrexone, Neurontin, Novantrone, Prednisone, Provigil, Rebif, Solumedrol, Symmetrel, Topamax, Tysabri, Wellbutrin, Xanax, Zanaflex, Zoloft, fingolimod, laquinimod, Mylinax (cladribine), teriflunomide, BG-12 (Biogen Idec's), firategrast (GSK/Mitsubishi Tanabe Pharma), ibudilast (MediciNova's), and CDP323 (Biogen/UCB).

According to an aspect of some embodiments of the present invention there is provided a method of predicting a benign multiple sclerosis course in a subject diagnosed with multiple sclerosis, the method comprising: (a) determining in a biological sample of the subject a level of expression of at least one polynucleotide selected from the group consisting of C22orf8, TLK1, HNRPH1, PLXDC1, TLK1, PKN2, ALS2CR8, FLJ12547, ZNF238, PDPR, NT5E, PASK, HPGD, IL6ST, JARID1A, PASK, LEF1, FLJ10246, MTUS1, FLJ14011, VSIG4, MARCH-VI, FLJ10613, EWSR1, ATP8A1, SLC4A7, FLJ21127, HNRPH1, ABLIM1, ITGA6, ADCY9, CROCC, SH3YL1, SMA4, SPTBN1, DPEP3, PDE3B, AF5Q31, NRCAM, DOCK9, IPW, FLJ20152, SIRPB2, GALNT4, CD28, TXK, ETS1, DGCR5, ZNF192, TCF7, CAMK4, SIM2, MGEA5, TGFBR2, RET, MAPK8IP3, RRN3, DKFZp547H025, FBXW11, ZNF423, DLG1, MGC17330, CD164L1, REPS1, ACHE, ITGB1BP2, LOC94431, LTK, RUNX1, EVER1, KIAA2010, CEACAM7, STX16, SLC4A5, CRTAP, RECQL5, MAGEF1, VIPR1, FLJ10979, TTC3, CRSP2, BAZ2A, GTF2I, MGC50853, KIAA0508, BPHL, LTBP4, FN3KRP, SCARB1, MGC17330, HYAL4, DGKA, FLJ11196, DHRS6, EPHB4, IDI2/GTPBP4, SNTG2, SLC7A6, PMS2L2, KIAA0436, TOSO, THRAP3, T3JAM, LOC283232, LOC92482, PTER, ATM, NUCB2, PIK3R2, MGC1136, CD59, JARID1A, FLJ39616, ABLIM1, PBP, MAPK8IP3, FTS, LHX5, TNFRSF7, MYC, PBXIP1, DATF1, HTF9C, PUS1, KIAA0924, C6orf4, KIAA0372, WDR42A, CRYZL1, TERE1, LTBP4, TTC3, NFATC1, POM121/LOC340318, TOSO, LOC348926/MGC16279/ SB153/FLJ10661, SPOCK2, KIAA0515, SLC37A4, CD44, SMARCA2, SPTBN1, C6orf130, TTC3, DLG1, SLC35E2, MCCC1, PMS2L11, RCN3, STX16, FLJ20618, STAT5B, SMARCA2, SATB1, POLR1D, ASXL1, REV1L, PMS2L2/ PMS2L5, FLJ12355, CCNB1IP1, FLJ12270, KIAA0692, MCM7, GPSN2, STX16, MMS19L, GTF2I/GTF2IP1, AKAP7, ZNF444, SLC35A3, MGEA5, RUTBC3, C20orf36, RAD17, ALG12, LOC112869, C6orf48, CUTC, LGTN, DEF6, WAC, HNRPH3, NS, KIAA0892, LRPPRC, HMG20A, DDX42, TINP1, ZDHHC17, C19orf2, EIF4B, LOC376745, DKFZP434C171, TH1L, C19orf13, RPL22, PHF15, EWSR1, EIF4B, FAM48A, YT521, NEK9, EIF3S7, RPS6, RPL35A, EEF2, RPL3, RPS6, UBA52, RPL6, RPS6, RPL13, AL353949, AL580863, AF052160, AW128846, AW974481, N92920, BG178274, AW303460, BF057458, AL050035, M59917, AK025422, AI693985, AU158442, AK021460, AL023773, NM_003790, AC005011, M90355, AL353580, U38964, D50683 and BE967207, wherein downregulation below a predetermined threshold in the level of expression relative to a level of expression of the at least one polynucleotide in a biological sample of a subject diagnosed with typical relapsing-remitting multiple sclerosis (RRMS) is indicative of the prediction of the benign multiple sclerosis course of the subject; (b) informing the subject of the prediction of the benign multiple sclerosis course; thereby predicting the benign multiple sclerosis course in the subject diagnosed with the multiple sclerosis.

According to an aspect of some embodiments of the present invention there is provided a method of predicting a benign multiple sclerosis course in a subject diagnosed with multiple sclerosis, the method comprising: (a) determining in a biological sample of the subject a level of expression of at least one polynucleotide selected from the group consisting of YWHAB, ATP6V1E1, UBB, MRLC2/MRCL3, UQCR, MRLC2, RTN4, UBE2A, RTN4, WDR1, PSMA6, C14orf123, PP1201, TBK1, CAST, CAST, RSN, PSME1, SDF2, GSTO1, CAST, DNCL1, SQRDL, ADIPOR2, ICMT, NDUFA6, NDUFA6, COX17, HIF1AN, FLJ20257, TBPL1, RAPGEF2, CRSP8, APOL1, PAOX, CNDP2, ETFA, DPP3, KPNA1, MGC3036, TUBB2, PDCL, CCL5, CDS2, RAP1GDS1, ATP6V1D, OBRGRP/LEPR, SF4, GCLC, MGST3, BICD2, BRF1, CHST12, EXOSC7, TOR1B, ZFP95, ILK, UNC13A, MTHFD2, CASP10, FLJ45850, CMRF-35H, ARF3, NDOR1, DUSP10, AP1M2, VRK2, GSN, PTRF, RBM19, RABGAP1L, ATP5S, STOM, TFPI2, SLCO3A1, PTPN12, CSF1, SIGLEC6, KIRREL, OBRGRP, TP53AP1, SUHW1, NUP98, IL15RA, MICB, CMRF-35H, SPHK1, TNFRSF6, FLJ1301, LRP5, STOM, EPHA2, SRC, FLJ11301, PSTPIP2, EBP, MCPH1, PTPRF, LIMK2, FSTL4, CBR1, MGC2654, MYCT1, NOL3, MITF, ATP10B, FBXO31, TBX21, LSS, SLC17A3, MNAB, CHPPR, GIF, VAMPS, ABCG2, KIF1B, LOH11CR2A, NID2, RBBP8, ETV7, CTSL, RUFY1, RSU1, PARD3, APOB, ACOX3, DAB2, LDLR, TJP2, GNAS, PARD3, NCKAP1, TAP2, HDGFRP3, LDLR, PIK3R3, HTR2B, GAS2L1, FER1L3, C3orf14, TP53TG3, LEPR, CLIC5, PDE4DIP, ATP9A, ITGB1BP1, INDO, SELP, FHL2, FER1L3, EGF, SIAT8A, HDGFRP3, LRAP, VWF, FLJ10134, IMP-3, DMN, MCTP1, FSTL1, CTNNAL1, RAB27B, THBS1, PROS1, MMRN1, CTTN, AL078596, AI148659, U00956 and M29383, wherein upregulation above a predetermined threshold in the level of expression relative to a level of expression of the at least one polynucleotide in a biological sample of a subject diagnosed with typical relapsing-remitting multiple sclerosis (RRMS) is indicative of the prediction of the benign multiple sclerosis course of the subject; (b) informing the subject of the prediction of the benign multiple sclerosis course; thereby predicting the benign multiple sclerosis course in the subject diagnosed with the multiple sclerosis.

According to an aspect of some embodiments of the present invention there is provided a method of monitoring treatment with an anti MS drug in a subject in need thereof, the method comprising: (a) treating the subject with the anti MS drug; and (b) determining in a biological sample of the subject a level of expression of at least one polynucleotide selected from the group consisting of YWHAB, ATP6V1E1, UBB, MRLC2/MRCL3, UQCR, MRLC2, RTN4, UBE2A, RTN4, WDR1, PSMA6, C14orf123, PP1201, TBK1, CAST, CAST, RSN, PSME1, SDF2, GSTO1, CAST, DNCL1, SQRDL, ADIPOR2, ICMT, NDUFA6, NDUFA6, COX17, HIF1AN, FLJ20257, TBPL1, RAPGEF2, CRSP8, APOL1, PAOX, CNDP2, ETFA, DPP3, KPNA1, MGC3036, TUBB2, PDCL, CCL5, CDS2, RAP1GDS1, ATP6V1D, OBRGRP/LEPR, SF4, GCLC, MGST3, BICD2, BRF1, CHST12, EXOSC7, TOR1B, ZFP95, ILK, UNC13A, MTHFD2, CASP10, FLJ45850, CMRF-35H, ARF3, NDOR1, DUSP10, AP1M2, VRK2, GSN, PTRF, RBM19, RABGAP1L, ATP5S, STOM, TFPI2, SLCO3A1, PTPN12, CSF1, SIGLEC6, KIRREL, OBRGRP, TP53AP1, SUHW1, NUP98, IL15RA, MICB, CMRF-35H, SPHK1, TNFRSF6, FLJ11301, LRP5, STOM, EPHA2, SRC, FLJ11301, PSTPIP2, EBP, MCPH1, PTPRF, LIMK2, FSTL4, CBR1, MGC2654, MYCT1, NOL3, MITF, ATP10B, FBXO31, TBX21, LSS, SLC17A3, MNAB, CHPPR, GIF, VAMPS, ABCG2, KIF1B, LOH11CR2A, NID2, RBBP8, ETV7, CTSL, RUFY1, RSU1, PARD3, APOB, ACOX3, DAB2, LDLR, TJP2, GNAS, PARD3, NCKAP1, TAP2, HDGFRP3, LDLR, PIK3R3, HTR2B, GAS2L1, FER1L3, C3orf14, TP53TG3, LEPR, CLIC5, PDE4DIP, ATP9A, ITGB1BP1, INDO, SELP, FHL2, FER1L3, EGF, SIAT8A, HDGFRP3, LRAP, VWF, FLJ10134, IMP-3, DMN, MCTP1, FSTL1, CTNNAL1, RAB27B, THBS1, PROS1, MMRN1, CTTN, AL078596, AI148659, U00956 and M29383, wherein an upregulation above a predetermined threshold in the level of expression relative to a level of expression of the at least one polynucleotide in a biological sample of a subject diagnosed with typical relapsing-remitting multiple sclerosis (RRMS) is indicative of treatment efficacy.

According to some embodiments of the invention, step (b) is effected also prior to step (a) and wherein the upregulation is with respect to a level of the at least one polynucleotide prior to the treating.

According to an aspect of some embodiments of the present invention there is provided a method of monitoring treatment with an anti MS drug in a subject in need thereof, the method comprising: (a) treating the subject with the anti MS drug; and (b) determining in a biological sample of the subject a level of expression of at least one polynucleotide selected from the group consisting of C22orf8, TLK1, HNRPH1, PLXDC1, TLK1, PKN2, ALS2CR8, FLJ12547, ZNF238, PDPR, NT5E, PASK, HPGD, IL6ST, JARID1A, PASK, LEF1, FLJ10246, MTUS1, FLJ14011, VSIG4, MARCH-VI, FLJ10613, EWSR1, ATP8A1, SLC4A7, FLJ21127, HNRPH1, ABLIM1, ITGA6, ADCY9, CROCC, SH3YL1, SMA4, SPTBN1, DPEP3, PDE3B, AF5Q31, NRCAM, DOCK9, IPW, FLJ20152, SIRPB2, GALNT4, CD28, TXK, ETS1, DGCR5, ZNF192, TCF7, CAMK4, SIM2, MGEA5, TGFBR2, RET, MAPK8IP3, RRN3, DKFZp547H025, FBXW11, ZNF423, DLG1, MGC17330, CD164L1, REPS1, ACHE, ITGB1BP2, LOC94431, LTK, RUNX1, EVER1, KIAA2010, CEACAM7, STX16, SLC4A5, CRTAP, RECQL5, MAGEF1, VIPR1, FLJ10979, TTC3, CRSP2, BAZ2A, GTF2I, MGC50853, KIAA0508, BPHL, LTBP4, FN3KRP, SCARB1, MGC17330, HYAL4, DGKA, FLJ11196, DHRS6, EPHB4, IDI2/GTPBP4, SNTG2, SLC7A6, PMS2L2, KIAA0436, TOSO, THRAP3, T3JAM, LOC283232, LOC92482, PTER, ATM, NUCB2, PIK3R2, MGC1136, CD59, JARID1A, FLJ39616, ABLIM1, PBP, MAPK8IP3, FTS, LHX5, TNFRSF7, MYC, PBXIP1, DATF1, HTF9C, PUS1, KIAA0924, C6orf4, KIAA0372, WDR42A, CRYZL1, TERE1, LTBP4, TTC3, NFATC1, POM121/LOC340318, TOSO, LOC348926/MGC16279/SB153/FLJ10661, SPOCK2, KIAA0515, SLC37A4, CD44, SMARCA2, SPTBN1, C6orf130, TTC3, DLG1, SLC35E2, MCCC1, PMS2L11, RCN3, STX16, FLJ20618, STAT5B, SMARCA2, SATB1, POLR1D, ASXL1, REV1L, PMS2L2/PMS2L5, FLJ12355, CCNB1IP1, FLJ12270, KIAA0692, MCM7, GPSN2, STX16, MMS19L, GTF2I/GTF2IP1, AKAP7, ZNF444, SLC35A3, MGEA5, RUTBC3, C20orf36, RAD17, ALG12, LOC112869, C6orf48, CUTC, LGTN, DEF6, WAC, HNRPH3, NS, KIAA0892, LRPPRC, HMG20A, DDX42, TINP1, ZDHHC17, C19orf2, EIF4B, LOC376745, DKFZP434C171, TH1L, C19orf13, RPL22, PHF15, EWSR1, EIF4B, FAM48A, YT521, NEK9, EIF3S7, RPS6, RPL35A, EEF2, RPL3, RPS6, UBA52, RPL6, RPS6, RPL13, AL353949, AL580863, AF052160, AW128846, AW974481, N92920, BG178274, AW303460, BF057458, AL050035, M59917, AK025422, AI693985, AU158442, AK021460, AL023773, NM_003790, AC005011, M90355, AL353580, U38964, D50683 and BE967207, wherein downregulation below a predetermined threshold in the level of expression relative to a level of expression of the at least one polynucleotide in a biological sample of a subject diagnosed with typical relapsing-remitting multiple sclerosis (RRMS) is indicative of treatment efficacy.

According to some embodiments of the invention, step (b) is effected also prior to step (a) and wherein the downregulation is with respect to a level of the at least one polynucleotide prior to the treating.

According to an aspect of some embodiments of the present invention there is provided a method of predicting a typical relapsing-remitting multiple sclerosis (RRMS) course in a subject diagnosed with multiple sclerosis, the method comprising: (a) determining in a biological sample of the subject a level of expression of at least one polynucleotide selected from the group consisting of YWHAB, ATP6V1E1, UBB, MRLC2/MRCL3, UQCR, MRLC2, RTN4, UBE2A, RTN4, WDR1, PSMA6, C14orf123, PP1201, TBK1, CAST, CAST, RSN, PSME1, SDF2, GSTO1, CAST, DNCL1, SQRDL, ADIPOR2, ICMT, NDUFA6, NDUFA6, COX17, HIF1AN, FLJ20257, TBPL1, RAPGEF2, CRSP8, APOL1, PAOX, CNDP2, ETFA, DPP3, KPNA1, MGC3036, TUBB2, PDCL, CCL5, CDS2, RAP1GDS1, ATP6V1D, OBRGRP/LEPR, SF4, GCLC, MGST3, BICD2, BRF1, CHST12, EXOSC7, TOR1B, ZFP95, ILK, UNC13A, MTHFD2, CASP10, FLJ45850, CMRF-35H, ARF3, NDOR1, DUSP10, AP1M2, VRK2, GSN, PTRF, RBM19, RABGAP1L, ATP5S, STOM, TFPI2, SLCO3A1, PTPN12, CSF1, SIGLEC6, KIRREL, OBRGRP, TP53AP1, SUHW1, NUP98, IL15RA, MICB, CMRF-35H, SPHK1, TNFRSF6, FLJ11301, LRP5, STOM, EPHA2, SRC, FLJ11301, PSTPIP2, EBP, MCPH1, PTPRF, LIMK2, FSTL4, CBR1, MGC2654, MYCT1, NOL3, MITF, ATP10B, FBXO31, TBX21, LSS, SLC17A3, MNAB, CHPPR, GIF, VAMPS, ABCG2, KIF1B, LOH11CR2A, NID2, RBBP8, ETV7, CTSL, RUFY1, RSU1, PARD3, APOB, ACOX3, DAB2, LDLR, TJP2, GNAS, PARD3, NCKAP1, TAP2, HDGFRP3, LDLR, PIK3R3, HTR2B, GAS2L1, FER1L3, C3orf14, TP53TG3, LEPR, CLIC5, PDE4DIP, ATP9A, ITGB1BP1, INDO, SELP, FHL2, FER1L3, EGF, SIAT8A, HDGFRP3, LRAP, VWF, FLJ10134, IMP-3, DMN, MCTP1, FSTL1, CTNNAL1, RAB27B, THBS1, PROS1, MMRN1, CTTN, AL078596, AI148659, U00956 and M29383, wherein downregulation below a predetermined threshold in the level of expression relative to a level of expression of the at least one polynucleotide in a biological sample of a subject diagnosed with benign multiple sclerosis (BMS) is indicative of the prediction of the relapsing-remitting multiple sclerosis course of the subject; (b) informing the subject of the prediction of the relapsing-remitting multiple sclerosis course; thereby predicting the relapsing-remitting multiple sclerosis course in the subject diagnosed with the multiple sclerosis.

According to an aspect of some embodiments of the present invention there is provided a method of predicting a typical relapsing-remitting multiple sclerosis (RRMS) course in a subject diagnosed with multiple sclerosis, the method comprising: (a) determining in a biological sample of the subject a level of expression of at least one polynucleotide selected from the group consisting of C22orf8, TLK1, HNRPH1, PLXDC1, TLK1, PKN2, ALS2CR8, FLJ12547, ZNF238, PDPR, NT5E, PASK, HPGD, IL6ST, JARID1A, PASK, LEF1, FLJ10246, MTUS1, FLJ14011, VSIG4, MARCH-VI, FLJ10613, EWSR1, ATP8A1, SLC4A7, FLJ21127, HNRPH1, ABLIM1, ITGA6, ADCY9, CROCC, SH3YL1, SMA4, SPTBN1, DPEP3, PDE3B, AF5Q31, NRCAM, DOCK9, IPW, FLJ20152, SIRPB2, GALNT4, CD28, TXK, ETS1, DGCR5, ZNF192, TCF7, CAMK4, SIM2, MGEA5, TGFBR2, RET, MAPK8IP3, RRN3, DKFZp547H025, FBXW11, ZNF423, DLG1, MGC17330, CD164L1, REPS1, ACHE, ITGB1BP2, LOC94431, LTK, RUNX1, EVER1, KIAA2010, CEACAM7, STX16, SLC4A5, CRTAP, RECQL5, MAGEF1, VIPR1, FLJ10979, TTC3, CRSP2, BAZ2A, GTF2I, MGC50853, KIAA0508, BPHL, LTBP4, FN3KRP, SCARB1, MGC17330, HYAL4, DGKA, FLJ11196, DHRS6, EPHB4, IDI2/GTPBP4, SNTG2, SLC7A6, PMS2L2, KIAA0436, TOSO, THRAP3, T3JAM, LOC283232, LOC92482, PTER, ATM, NUCB2, PIK3R2, MGC1136, CD59, JARID1A, FLJ39616, ABLIM1, PBP, MAPK8IP3, FTS, LHX5, TNFRSF7, MYC, PBXIP1, DATF1, HTF9C, PUS1, KIAA0924, C6orf4, KIAA0372, WDR42A, CRYZL1, TERE1, LTBP4, TTC3, NFATC1, POM121/LOC340318, TOSO, LOC348926/MGC16279/SB153/FLJ10661, SPOCK2, KIAA0515, SLC37A4, CD44, SMARCA2, SPTBN1, C6orf130, TTC3, DLG1, SLC35E2, MCCC1, PMS2L11, RCN3, STX16, FLJ20618, STAT5B, SMARCA2, SATB1, POLR1D, ASXL1, REV1L, PMS2L2/PMS2L5, FLJ12355, CCNB1IP1, FLJ12270, KIAA0692, MCM7, GPSN2, STX16, MMS19L, GTF2I/GTF2IP1, AKAP7, ZNF444, SLC35A3, MGEA5, RUTBC3, C20orf36, RAD17, ALG12, LOC112869, C6orf48, CUTC, LGTN, DEF6, WAC, HNRPH3, NS, KIAA0892, LRPPRC, HMG20A, DDX42, TINP1, ZDHHC17, C19orf2, EIF4B, LOC376745, DKFZP434C171, TH1L, C19orf13, RPL22, PHF15, EWSR1, EIF4B, FAM48A, YT521, NEK9, EIF3S7, RPS6, RPL35A, EEF2, RPL3, RPS6, UBA52, RPL6, RPS6, RPL13, AL353949, AL580863, AF052160, AW128846, AW974481, N92920, BG178274, AW303460, BF057458, AL050035, M59917, AK025422, AI693985, AU158442, AK021460, AL023773, NM_003790, AC005011, M90355, AL353580, U38964, D50683 and BE967207, wherein upregulation above a predetermined threshold in the level of expression relative to a level of expression of the at least one polynucleotide in a biological sample of a subject diagnosed with benign multiple sclerosis (BMS) is indicative of the prediction of the relapsing-remitting multiple sclerosis course of the subject; (b) informing the subject of the prediction of the relapsing-remitting multiple sclerosis course; thereby predicting the relapsing-remitting multiple sclerosis course in the subject diagnosed with the multiple sclerosis.

According to an aspect of some embodiments of the present invention there is provided a method of treating a subject diagnosed with multiple sclerosis, the method comprising: (a) determining if the subject is predicted to have a relapsing-remitting multiple sclerosis course according to the method of the invention, (b) selecting a treatment regimen based on the prediction of the relapsing-remitting multiple sclerosis course; thereby treating the subject diagnosed with multiple sclerosis.

According to an aspect of some embodiments of the present invention there is provided a method of treating a subject diagnosed with multiple sclerosis, the method comprising: (a) determining in a biological sample of the subject a level of expression of RRN3, wherein upregulation above a predetermined threshold in the level of expression relative to a level of expression of the RRN3 in a biological sample of a subject diagnosed with benign multiple sclerosis (BMS) is indicative of the prediction of the relapsing-remitting multiple sclerosis course of the subject; (b) administering to the subject a therapeutically effective amount of diterpenoid triepoxide Triptolide (TPT) or a derivative thereof, thereby treating the subject.

According to an aspect of some embodiments of the present invention there is provided a method of treating a subject diagnosed with multiple sclerosis, the method comprising: administering to the subject an agent which downregulates the expression level and/or activity of at least one polynucleotide or polypeptide of the RNA polymerase 1 pathway, with the proviso that the agent is not diterpenoid triepoxide Triptolide (TPT), thereby treating the subject.

According to an aspect of some embodiments of the present invention there is provided a probeset comprising a plurality of oligonucleotides and no more than 500 oligonucleotides, the plurality of oligonucleotides specifically recognizing the polynucleotides of C22orf8, TLK1, HNRPH1, PLXDC1, TLK1, PKN2, ALS2CR8, FLJ12547, ZNF238, PDPR, NT5E, PASK, HPGD, IL6ST, JARID1A, PASK, LEF1, FLJ10246, MTUS1, FLJ14011, VSIG4, MARCH-VI, FLJ10613, EWSR1, ATP8A1, SLC4A7, FLJ21127, HNRPH1, ABLIM1, ITGA6, ADCY9, CROCC, SH3YL1, SMA4, SPTBN1, DPEP3, PDE3B, AF5Q31, NRCAM, DOCK9, IPW, FLJ20152, SIRPB2, GALNT4, CD28, TXK, ETS1, DGCR5, ZNF192, TCF7, CAMK4, SIM2, MGEA5, TGFBR2, RET, MAPK8IP3, RRN3, DKFZp547H025, FBXW11, ZNF423, DLG1, MGC17330, CD164L1, REPS1, ACHE, ITGB1BP2, LOC94431, LTK, RUNX1, EVER1, KIAA2010, CEACAM7, STX16, SLC4A5, CRTAP, RECQL5, MAGEF1, VIPR1, FLJ10979, TTC3, CRSP2, BAZ2A, GTF2I, MGC50853, KIAA0508, BPHL, LTBP4, FN3KRP, SCARB1, MGC17330, HYAL4, DGKA, FLJ11196, DHRS6, EPHB4, IDI2/GTPBP4, SNTG2, SLC7A6, PMS2L2, KIAA0436, TOSO, THRAP3, T3JAM, LOC283232, LOC92482, PTER, ATM, NUCB2, PIK3R2, MGC1136, CD59, JARID1A, FLJ39616, ABLIM1, PBP, MAPK8IP3, FTS, LHX5, TNFRSF7, MYC, PBXIP1, DATF1, HTF9C, PUS1, KIAA0924, C6orf4, KIAA0372, WDR42A, CRYZL1, TERE1, LTBP4, TTC3, NFATC1, POM121/LOC340318, TOSO, LOC348926/MGC16279/SB153/FLJ10661, SPOCK2, KIAA0515, SLC37A4, CD44, SMARCA2, SPTBN1, C6orf130, TTC3, DLG1, SLC35E2, MCCC1, PMS2L11, RCN3, STX16, FLJ20618, STAT5B, SMARCA2, SATB1, POLR1D, ASXL1, REV1L, PMS2L2/PMS2L5, FLJ12355, CCNB1IP1, FLJ12270, KIAA0692, MCM7, GPSN2, STX16, MMS19L, GTF2I/GTF2IP1, AKAP7, ZNF444, SLC35A3, MGEA5, RUTBC3, C20orf36, RAD17, ALG12, LOC112869, C6orf48, CUTC, LGTN, DEF6, WAC, HNRPH3, NS, KIAA0892, LRPPRC, HMG20A, DDX42, TINP1, ZDHHC17, C19orf2, EIF4B, LOC376745, DKFZP434C171, TH1L, C19orf13, RPL22, PHF15, EWSR1, EIF4B, FAM48A, YT521, NEK9, EIF3S7, RPS6, RPL35A, EEF2, RPL3, RPS6, UBA52, RPL6, RPS6, RPL13, AL353949, AL580863, AF052160, AW128846, AW974481, N92920, BG178274, AW303460, BF057458, AL050035, M59917, AK025422, AI693985, AU158442, AK021460, AL023773, NM_003790, AC005011, M90355, AL353580, U38964, D50683, BE967207, YWHAB, ATP6V1E1, UBB, MRLC2/MRCL3, UQCR, MRLC2, RTN4, UBE2A, RTN4, WDR1, PSMA6, C14orf123, PP1201, TBK1, CAST, CAST, RSN, PSME1, SDF2, GSTO1, CAST, DNCL1, SQRDL, ADIPOR2, ICMT, NDUFA6, NDUFA6, COX17, HIF1AN, FLJ20257, TBPL1, RAPGEF2, CRSP8, APOL1, PAOX, CNDP2, ETFA, DPP3, KPNA1, MGC3036, TUBB2, PDCL, CCL5, CDS2, RAP1GDS1, ATP6V1D, OBRGRP/LEPR, SF4, GCLC, MGST3, BICD2, BRF1, CHST12, EXOSC7, TOR1B, ZFP95, ILK, UNC13A, MTHFD2, CASP10, FLJ45850, CMRF-35H, ARF3, NDOR1, DUSP10, AP1M2, VRK2, GSN, PTRF, RBM19, RABGAP1L, ATP5S, STOM, TFPI2, SLCO3A1, PTPN12, CSF1, SIGLEC6, KIRREL, OBRGRP, TP53AP1, SUHW1, NUP98, IL15RA, MICB, CMRF-35H, SPHK1, TNFRSF6, FLJ11301, LRP5, STOM, EPHA2, SRC, FLJ11301, PSTPIP2, EBP, MCPH1, PTPRF, LIMK2, FSTL4, CBR1, MGC2654, MYCT1, NOL3, MITF, ATP10B, FBXO31, TBX21, LSS, SLC17A3, MNAB, CHPPR, GIF, VAMPS, ABCG2, KIF1B, LOH11CR2A, NID2, RBBP8, ETV7, CTSL, RUFY1, RSU1, PARD3, APOB, ACOX3, DAB2, LDLR, TJP2, GNAS, PARD3, NCKAP1, TAP2, HDGFRP3, LDLR, PIK3R3, HTR2B, GAS2L1, FER1L3, C3orf14, TP53TG3, LEPR, CLIC5, PDE4DIP, ATP9A, ITGB1BP1, INDO, SELP, FHL2, FER1L3, EGF, SIAT8A, HDGFRP3, LRAP, VWF, FLJ10134, IMP-3, DMN, MCTP1, FSTL1, CTNNAL1, RAB27B, THBS1, PROS1, MMRN1, CTTN, AL078596, AI148659, U00956 and M29383.

According to an aspect of some embodiments of the present invention there is provided a kit for predicting a benign or relapsing-remitting course in a subject diagnosed with multiple sclerosis, comprising the probeset of the invention.

According to some embodiments of the invention, the kit further comprising a positive control for an expression level of at least one of the polynucleotides.

According to some embodiments of the invention, the at least one polynucleotide comprises the polynucleotides of RRN3, POLR1D and LRPPRC.

According to some embodiments of the invention, the treatment regimen comprises administering to the subject an agent which downregulates the expression level and/or activity of at least one polynucleotide or polypeptide of the RNA polymerase 1 pathway, thereby treating the subject.

According to some embodiments of the invention, the at least one polynucleotide or polypeptide of the RNA polymerase 1 pathway comprises RRN3.

According to some embodiments of the invention, the at least one polynucleotide or polypeptide of the RNA polymerase 1 pathway further comprises POLR1D and LRPPRC.

According to some embodiments of the invention, the method further comprising determining in the biological sample of the subject the level of expression of POLR1D and/or LRPPRC, wherein upregulation above a predetermined threshold in the level of expression relative to a level of expression of the POLR1D and/or LRPPRC in a biological sample of a subject diagnosed with benign multiple sclerosis (BMS) is indicative of the prediction of the relapsing-remitting multiple sclerosis course of the subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
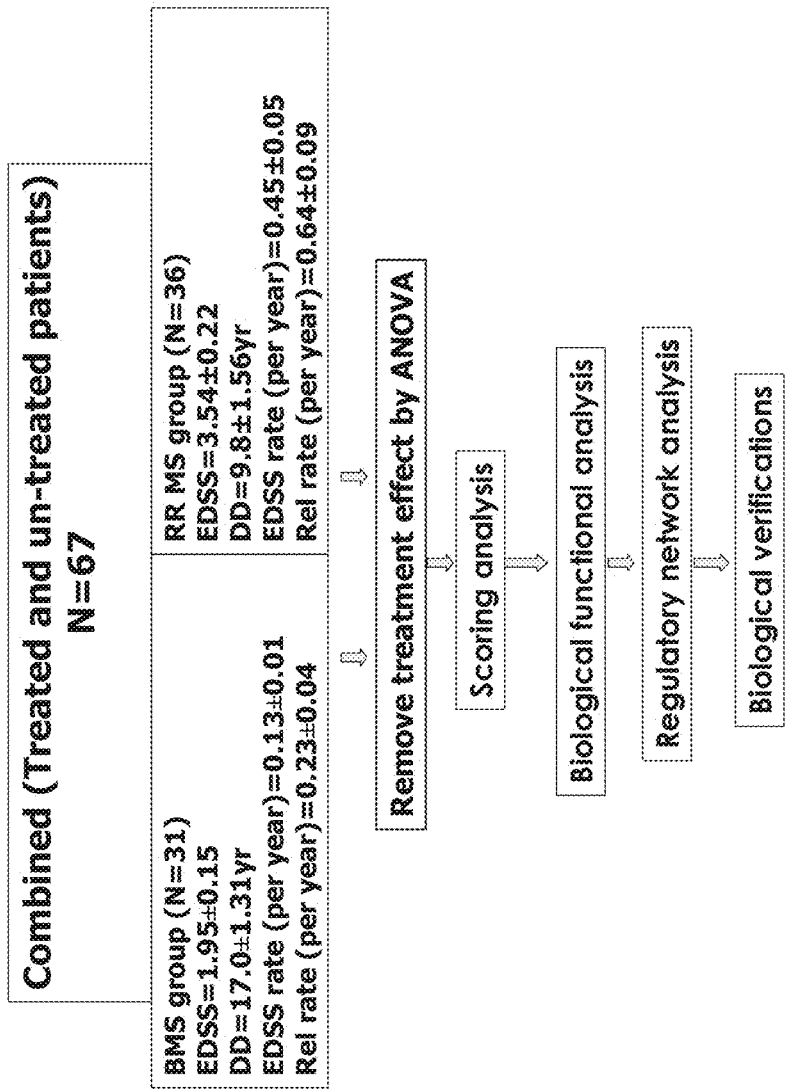
FIG. 1 is a schematic illustration depicting the design of the study for identification of genes which predict benign multiple sclerosis.

The present invention, in some embodiments thereof, relates to methods of classifying a subject as being more likely to have BMS or to be more likely to have typical RRMS and, more particularly, but not exclusively, to methods of diagnosing typical RRMS or BMS and treating a subject based on the diagnosis.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have applied a high throughput gene expression technology to identify biomarkers for the diagnosis of benign multiple sclerosis (BMS) and for potential targets for therapeutic interventions in order switch RRMS course of disease to a BMS course of disease.

Thus, as shown in Example 1 of the Examples section which follows, the present inventors have identified 406 genes which are differentially expressed between multiple sclerosis subjects having a benign MS course or an RRMS course (typical RRMS) (Tables 1 and 2). These genes can be used for classification of MS disease course, diagnosis of a typical RRMS course and selecting a suitable treatment regimen for a subject diagnosed with MS which will prevent deterioration in the subject's state while avoiding unnecessary side effects. In addition, as shown in Table 3 (Example 1) and Tables 4A-C (Example 2) the present inventors have uncovered that the expression level of genes which are involved in the RNA polymerase I pathway such as POLR1D, LRPPRC, RRN3 and NCL is downregulated in subjects having a BMS course of MS as compared to the expression level of these genes in subjects having an RRMS course of MS. Moreover, as shown in Tables 5 and 6 (Example 2) the present inventors identified MIGs (most informative genes) discriminating between BMS and typical RRMS and genes which can classify subjects as having a BMS or a typical RRMS. These results suggest the use of genes involved in the RNA polymerase I pathway as diagnostic markers and drug targets for treating and preventing a typical RRMS course in a subject diagnosed with MS.

Thus, according to an aspect of some embodiments of the invention there is provided a method of classifying a subject as being more likely to have benign multiple sclerosis (BMS) or as being more likely to have typical relapsing remitting multiple sclerosis (RRMS), the method comprising comparing a level of expression of at least one gene involved in the RNA polymerase I pathway in a cell of the subject to a reference expression data of the at least one gene obtained from a cell of at least one subject pre-diagnosed as having BMS and/or from a cell of at least one subject pre-diagnosed as having typical RRMS, thereby classifying the subject as being more likely to have BMS or as being more likely to have typical RRMS.

The term "subject" refers to mammal, preferably a human being.

According to some embodiments of the invention, the subject is diagnosed with multiple sclerosis.

As used herein, the phrase "diagnosed with multiple sclerosis" refers to a subject who experienced at least one neurological attack affecting the central nervous system (CNS) accompanied by demyelinating lesions within the brain or spinal cord, which may have, but not necessarily confirmed by magnetic resonance imaging (MRI). The neurological attack can involve acute or sub-acute neurological symptomatology (attack) manifested by various clinical presentations like unilateral loss of vision, vertigo, ataxia, incoordination, gait difficulties, sensory impairment characterized by paresthesia, dysesthesia, sensory loss, urinary disturbances until incontinence, diplopia, dysarthria, various degrees of motor weakness until paralysis, cognitive decline either as a monosymptomatic or in combination. The symptoms usually remain for several days to few weeks, and then partially or completely resolve.

The accepted diagnostic criteria of multiple sclerosis are presented in Hypertext Transfer Protocol://World Wide Web (dot) mult-sclerosis (dot) org/DiagnosticCriteria (dot) html.

According to some embodiments of the invention, the subject is suspected of having multiple sclerosis.

According to some embodiments of the invention, the subject has probable multiple sclerosis.

According to some embodiments of the invention, the subject does not have a primary progressive course (PPMS).

According to some embodiments of the invention, the subject does not have a secondary progressive MS course (SPMS).

As used herein the term "classifying" refers to determining if the subject is more likely to have benign multiple sclerosis (BMS) or typical relapsing remitting multiple sclerosis (RRMS).

As used herein the phrase "being more likely to have" refers to having increased probability to have a certain disease course (classification of disease) than another disease course.

According to some embodiments of the invention, the phrase "being more likely to have" refers to a probability of at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, e.g., about 100% that the subject has a certain disease course and not the other disease course, i.e., a BMS or typical RRMS.

As used herein, the phrase "benign multiple sclerosis" refers to a subject having MS and exhibiting an Expanded Disability Status Scale (EDSS) of less than 3.0 following at least 10 years from onset and/or diagnosis of MS.

As used herein, the phrase "typical RRMS" or a "relapsing-remitting multiple sclerosis course", which is interchangeably used herein, refers to a subject having MS and exhibiting an Expanded Disability Status Scale (EDSS) higher than 3.0 within less than 10 years of disease onset and/or diagnosis.

The phrase "onset of multiple sclerosis (MS)" as used herein refers to the time of occurrence of the first clinical neurological symptomatology suggestive of MS.

The Kurtzke EDSS is a method scale of quantifying disability in MS by scoring eight Functional Systems (FS) (pyramidal, cerebellar, brainstem, sensory, bowel and bladder, visual, cerebral, and other) and allows neurologists to assign a Functional System Score (FSS) in each and to combine the FSS scores into the EDSS score as follows:

EDSS 0.0—Normal neurological examination;
EDSS 1.0—No disability, minimal signs in one FS;
EDSS 1.5—No disability, minimal signs in more than one FS;
EDSS 2.0—Minimal disability in one FS;
EDSS 2.5—Mild disability in one FS or minimal disability in two FS;
EDSS 3.0—Moderate disability in one FS, or mild disability in three or four FS. Fully ambulatory;
EDSS 3.5—Fully ambulatory but with moderate disability in one FS and more than minimal disability in several others;
EDSS 4.0—Fully ambulatory without aid, self-sufficient, up and about some 12 hours a day despite relatively severe disability; able to walk without aid or rest some 500 meters;
EDSS 4.5—Fully ambulatory without aid, up and about much of the day, able to work a full day, may otherwise have some limitation of full activity or require minimal assistance; characterized by relatively severe disability; able to walk without aid or rest some 300 meters;
EDSS 5.0—Ambulatory without aid or rest for about 200 meters; disability severe enough to impair full daily activities (work a full day without special provisions);
EDSS 5.5—Ambulatory without aid or rest for about 100 meters; disability severe enough to preclude full daily activities;
EDSS 6.0—Intermittent or unilateral constant assistance (cane, crutch, brace) required to walk about 100 meters with or without resting;
EDSS 6.5—Constant bilateral assistance (canes, crutches, braces) required to walk about 20 meters without resting;
EDSS 7.0—Unable to walk beyond approximately five meters even with aid, essentially restricted to wheelchair; wheels self in standard wheelchair and transfers alone; up and about in wheelchair some 12 hours a day;
EDSS 7.5—Unable to take more than a few steps; restricted to wheelchair; may need aid in transfer; wheels self but cannot carry on in standard wheelchair a full day, May require motorized wheelchair;
EDSS 8.0—Essentially restricted to bed or chair or perambulated in wheelchair, but may be out of bed itself much of the day; retains many self-care functions; generally has effective use of arms;
EDSS 8.5—Essentially restricted to bed much of day, has some effective use of arms retains some self care functions;
EDSS 9.0—Confined to bed; can still communicate and eat;
EDSS 9.5—Totally helpless bed patient; unable to communicate effectively or eat/swallow;
EDSS 10.0—Death due to MS;

As mentioned, the diagnosis of MS is performed by clinical neurological symptoms and/or findings such as laboratory tests involving evaluation of IgG synthesis and oligoclonal bands (immunoglobulins) in the cerebrospinal fluid (CSF) which provide evidence of chronic inflammation of the central nervous system, and brain or spinal cord MRI according to the McDonald criteria [McDonald W I, Compston A, Edan G, et al., 2001, "Recommended diagnostic criteria for multiple sclerosis: guidelines from the International Panel on the diagnosis of multiple sclerosis". Ann Neurol. 50 (1): 121-7; Polman C H, Reingold S C, Edan G, et al., 2005, "Diagnostic criteria for multiple sclerosis: 2005 revisions to the "McDonald Criteria"". Ann Neurol. 58 (6): 840-6].

It should be noted that onset of multiple sclerosis and the diagnosis of multiple sclerosis could occur on the same time.

As used herein, the phrase "level of expression" refers to the degree of gene expression and/or gene product activity in a specific cell. For example, up-regulation or down-regulation of various genes can affect the level of the gene product (i.e., RNA and/or protein) in a specific cell.

Sequence information regarding gene products (i.e., RNA transcripts and polypeptide sequences) of the genes of the polynucleotides of the invention such as the genes of RNA polymerase I pathway and of probes which can be used to detect thereof can be found in Tables 1, 2, 3, 5 and 6 of the Examples section which follows.

It should be noted that the level of expression can be determined in arbitrary absolute units, or in normalized units (relative to known expression levels of a control reference). For example, when using DNA chips, the expression levels are normalized according to the chips' internal controls or by using quantile normalization such as RMA.

As used herein the phrase "a cell of the subject" refers to at least one cell (e.g., an isolated cell), cell culture, cell content and/or cell secreted content which contains RNA and/or proteins of the subject. Examples include a blood cell, a cell obtained from any tissue biopsy [e.g., cerebrospinal fluid, (CSF), brain biopsy], a bone marrow cell, body fluids such as plasma, serum, saliva, spinal fluid, lymph fluid, the external sections of the skin, respiratory, intestinal, and genitourinary tracts, tears, saliva, sputum and milk. According to an embodiment of the invention, the cell is a blood cell (e.g., white blood cells, macrophages, B- and T-lymphocytes, monocytes, neutrophiles, eosinophiles, and basophiles) which can be obtained using a syringe needle from a vein of the subject. It should be noted that the cell may be isolated from the subject (e.g., for in vitro detection) or may optionally comprise a cell that has not been physically removed from the subject (e.g., in vivo detection).

According to some embodiments of the invention, the white blood cell comprises peripheral blood mononuclear cells (PBMC). The phrase, "peripheral blood mononuclear cells (PBMCs)" as used herein, refers to a mixture of monocytes and lymphocytes. Several methods for isolating white blood cells are known in the art. For example, PBMCs can be isolated from whole blood samples using density gradient centrifugation procedures. Typically, anticoagulated whole blood is layered over the separating medium. At the end of the centrifugation step, the following layers are visually observed from top to bottom: plasma/platelets, PBMCs, separating medium and erythrocytes/granulocytes. The PBMC layer is then removed and washed to remove contaminants (e.g., red blood cells) prior to determining the expression level of the polynucleotide(s) therein.

The cell or the biological sample comprising same can be obtained from the subject at any time, e.g., immediately after an attack or at any time during remission.

According to some embodiments of the invention, the level of expression of the gene(s) of the invention is determined using an RNA and/or a protein detection method.

According to some embodiments of the invention, the RNA or protein molecules are extracted from the cell of the subject.

Methods of extracting RNA or protein molecules from cells of a subject are well known in the art. Once obtained, the RNA or protein molecules can be characterized for the expression and/or activity level of various RNA and/or protein molecules using methods known in the arts.

Non-limiting examples of methods of detecting RNA molecules in a cell sample include Northern blot analysis, RT-PCR, RNA in situ hybridization (using e.g., DNA or RNA probes to hybridize RNA molecules present in the cells or tissue sections), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface [e.g., a glass wafer) with addressable location, such as Affymetrix microarray (Affymetrix®, Santa Clara, Calif.)].

For example, the level of RRN3 in a sample can be determined by RT-PCR using primers available from Santa Cruz Biotechnology Inc. (sc-106866-PR), or Taqman Gene Expression Assay HS00607907_m1 (Applied Biosystems, Foster City, Calif., USA), according to manufacturer's recommendation.

Non-limiting examples of methods of detecting the level and/or activity of specific protein molecules in a cell sample include Enzyme linked immunosorbent assay (ELISA), Western blot analysis, radio-immunoassay (RIA), Fluorescence activated cell sorting (FACS), immunohistochemical analysis, in situ activity assay (using e.g., a chromogenic substrate applied on the cells containing an active enzyme), in vitro activity assays (in which the activity of a particular enzyme is measured in a protein mixture extracted from the cells). For example, in case the detection of the expression level of a secreted protein is desired, ELISA assay may be performed on a sample of fluid obtained from the subject (e.g., serum), which contains cell-secreted content.

As used herein the phrase "reference expression data" refers to the expression level of the gene in a cell of at least one subject who is pre-diagnosed as having BMS or typical RRMS. Such as an expression level can be known from the literature, from the database, or from biological samples comprising RNA or protein molecules obtained from a reference subject who is already diagnosed as having BMS or typical RRMS.

As used herein the phrase "pre-diagnosed" refers to being diagnosed based on the acceptable clinical tools/markers as described above (e.g., by evaluating the EDSS score after 10 years from onset or diagnosis of MS).

According to some embodiments of the invention, the reference expression data is obtained from at least subject who is pre-diagnosed as having BMS, e.g., from at least 2, from at least 3, from at least 4, from at least 5, from at least 6, from at least 7, from at least 8, from at least 9, from at least 10, from at least 20, from at least 30, from at least 40, from at least 50, from at least 100 or more subjects who are pre-diagnosed as having BMS.

According to some embodiments of the invention, the reference expression data is obtained from at least one subject who is pre-diagnosed as having typical RRMS, e.g., from at least 2, from at least 3, from at least 4, from at least 5, from at least 6, from at least 7, from at least 8, from at least 9, from at least 10, from at least 20, from at least 30, from at least 40, from at least 50, from at least 100 or more subjects who are pre-diagnosed as having typical RRMS.

It should be noted that when more than one reference subjects (i.e., a subject who is pre-diagnosed as having BMS or typical RRMS) is used, the reference expression data may comprise an average of the expression level of several or all subjects, and those of skills in the art are capable of averaging expression levels from 2 or more subject, using e.g., normalized expression values.

According to some embodiments of the invention, a decrease above a predetermined threshold in the level of expression of the at least one gene in the cell of the subject relative to the reference expression data of the at least one gene obtained from a cell of the at least one subject having the typical RRMS classifies the subject as being more likely to have the BMS.

As used herein the phrase "a decrease above a predetermined threshold" refers to a decrease in the level of expression in the cell of the subject relative to the reference expression data obtained from a cell of the at least one subject having the typical RRMS which is higher than a predetermined threshold such as a about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the reference expression data obtained from a cell of the at least subject having the typical RRMS.

According to some embodiments of the invention, an increase above a predetermined threshold in the level of expression of the at least one gene in the cell of the subject relative to the reference expression data of the at least one gene obtained from a cell of the at least one subject having the BMS classifies the subject as being more likely to have the typical RRMS.

As used herein the phrase "an increase above a predetermined threshold" refers to an increase in the level of expression in the cell of the subject relative to the reference expression data obtained from a cell of the at least one subject having the BMS which is higher than a predetermined threshold such as a about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the reference expression data obtained from a cell of the at least one subject having the BMS.

According to some embodiments of the invention, when a level of expression of the at least one gene in the cell of the subject is identical or changed below a predetermined threshold as compared to the reference expression data of the at least one gene obtained from a cell of the at least one subject having the BMS, then the subject is classified as being more likely to have the BMS.

As used herein the phrase "changed below a predetermined threshold as compared to the reference expression data . . . subject having the BMS" refers to an increase or a decrease in the level of expression in the cell of the subject relative to the reference expression data obtained from a cell of the at least one subject having the BMS which is lower than a predetermined threshold, such as lower than about 10 times, e.g., lower than about 9 times, e.g., lower than about 8 times, e.g., lower than about 7 times, e.g., lower than about 6 times, e.g., lower than about 5 times, e.g., lower than about 4 times, e.g., lower than about 3 times, e.g., lower than about 2 times, e.g., lower than about 90%, e.g., lower than about 80%, e.g., lower than about 70%, e.g., lower than about 60%, e.g., lower than about 50%, e.g., lower than about 40%, e.g., lower than about 30%, e.g., lower than about 20%, e.g., lower than about 10%, e.g., lower than about 9%, e.g., lower than about 8%, e.g., lower than about 7%, e.g., lower than about 6%, e.g., lower than about 5%, e.g., lower than about 4%, e.g., lower than about 3%, e.g., lower than about 2%, e.g., lower than about 1% relative to the reference expression data obtained from the at least one subject having the BMS.

According to some embodiments of the invention, when a level of expression of the at least one gene in the cell of the subject is identical or changed below a predetermined threshold as compared to the reference expression data of the at least one gene obtained from a cell of the at least one subject having the typical RRMS, then the subject is classified as being more likely to have the typical RRMS.

As used herein the phrase "changed below a predetermined threshold as compared to the reference expression data . . . subject having the typical RRMS" refers to an increase or a decrease in the level of expression in the cell of the subject relative to the reference expression data obtained from a cell of the one subject having the typical RRMS which is lower than a predetermined threshold, such as lower than about 10 times, e.g., lower than about 9 times, e.g., lower than about 8 times, e.g., lower than about 7 times, e.g., lower than about 6 times, e.g., lower than about 5 times, e.g., lower than about 4 times, e.g., lower than about 3 times, e.g., lower than about 2 times, e.g., lower than about 90%, e.g., lower than about 80%, e.g., lower than about 70%, e.g., lower than about 60%, e.g., lower than about 50%, e.g., lower than about 40%, e.g., lower than about 30%, e.g., lower than about 20%, e.g., lower than about 10%, e.g., lower than about 9%, e.g., lower than about 8%, e.g., lower than about 7%, e.g., lower than about 6%, e.g., lower than about 5%, e.g., lower than about 4%, e.g., lower than about 3%, e.g., lower than about 2%, e.g., lower than about 1% relative to the reference expression data obtained from the at least one subject having the typical RRMS.

Non-limiting examples of genes involved in the RNA polymerase I pathway which can be used according to the method of the invention are provided in Table 3 along with representative polynucleotides thereof and probes which can be used to detect thereof (Example 1 of the Examples section which follows; e.g., RRN3, LRPPRC, POLR1B, POLR1C, POLR1D, POLR2A, POLR2B, POLR2C, POLR2D, POLR2E, POLR2E, POLR2F, POLR2G, POLR2H, POLR2I, POLR2J, POLR2J2, MGC13098, POLR2K, POLR2L, POLR3B, POLR3C, POLR3D, POLR3E, POLR3F, POLR3G, POLR3K, POLRMT, POLRMT and POLS).

According to some embodiments of the invention, the at least one gene involved in the RNA polymerase 1 pathway is selected from the group consisting of POLR1D, LRPPRC, RRN3 and NCL.

According to some embodiments of the invention, the at least one gene involved in the RNA polymerase 1 pathway is RRN3.

According to some embodiments of the invention, the at least one gene involved in the RNA polymerase 1 pathway is LRPPRC.

According to some embodiments of the invention, the at least one gene involved in the RNA polymerase 1 pathway is POLR1D.

According to some embodiments of the invention, the at least one gene involved in the RNA polymerase 1 pathway comprises RRN3 and POLR1D.

According to some embodiments of the invention, the at least one gene involved in the RNA polymerase 1 pathway comprises RRN3 and LRPPRC.

According to some embodiments of the invention, the at least one gene involved in the RNA polymerase 1 pathway comprises POLR1D and LRPPRC.

According to some embodiments of the invention, the at least one gene involved in the RNA polymerase 1 pathway comprises RRN3, LRPPRC and POLR1D.

According to some embodiments of the invention, the at least one gene involved in the RNA polymerase 1 pathway is RRN3 and NCL.

According to some embodiments of the invention, the at least one gene involved in the RNA polymerase 1 pathway is LRPPRC and NCL.

According to some embodiments of the invention, the at least one gene involved in the RNA polymerase 1 pathway is POLR1D and NCL.

According to some embodiments of the invention, the at least one gene involved in the RNA polymerase 1 pathway comprises RRN3, POLR1D and NCL.

According to some embodiments of the invention, the at least one gene involved in the RNA polymerase 1 pathway comprises RRN3, LRPPRC and NCL.

According to some embodiments of the invention, the at least one gene involved in the RNA polymerase 1 pathway comprises POLR1D, LRPPRC and NCL.

According to some embodiments of the invention, the at least one gene involved in the RNA polymerase 1 pathway comprises RRN3, LRPPRC, POLR1D and NCL.

Tables 4A-C in the Examples section which follows demonstrate exemplary combinations of genes of the RNA polymerase I pathway along with their classification rates for BMS and typical RRMS.

The prediction of the MS course is important in terms of monitoring the clinical state of the subject (e.g., how often does the patient need to be evaluated for the disease progression in terms of neurological evaluation and EDSS), planning of subject's future life (e.g., making decisions regarding marriage, having children, being involved in high risk activities, getting a life-insurance, etc.) and planning the treatment regimen of the subject.

For example, a subject who is more likely to have BMS may be advised to reduce the frequency of neurological clinical evaluations to no more than once per year; to avoid frequent MRI examinations; to not be included in treatment schedule of MS; and/or to avoid receiving immunomodulatory drugs which have side effects or adverse events that can be even life-threatening [e.g., progressive multifocal leukoencephalopathy (PML) in MS patients treated with natalizumab (Tysabri®, Biogen-Idec); Hypertext Transfer Protocol://World Wide Web (dot) va (dot) gov/MS/pressreleases/Treating_Natalizumab_and_Risk_of_PML (dot) asp].

On the other hand, a subject who is more likely to have typical RRMS may be advised to have neurological clinical evaluations at a higher frequency, e.g., about 3-4 times per year; to have frequent MRI examinations; to be included in treatment schedule of MS; and/or to receive immunomodulatory drugs.

It should be noted that the classification of the subject as being more likely to have BMS or typical RRMS can be used to diagnose the subject as having BMS or typical RRMS.

As used herein the term "diagnosing" refers to determining presence or absence of a pathology (e.g., a disease, disorder, condition or syndrome) and/or likelihood of same, classifying a pathology or a symptom, determining a severity of the pathology, monitoring pathology progression, forecasting an outcome of a pathology and/or prospects of recovery and screening of a subject for a specific disease.

According to some embodiments of the invention the method of diagnosing is effected by (a) classifying the subject as being more likely to have BMS or as being more likely to have typical RRMS according to the method of the invention, (i) wherein when the subject is classified as being more likely to have the BMS then the subject is diagnosed as having BMS;

(ii) wherein when the subject is classified as being more likely to have the typical RRMS, then the subject is diagnosed as having typical RRMS; and (c) informing the subject of the diagnosis, thereby diagnosing the subject pre-diagnosed with the MS as having the BMS or the typical RRMS.

According to some embodiments of the invention, the subject is pre-diagnosed with multiple sclerosis (MS), i.e., has a confirmed diagnosis of MS without knowing the disease course, e.g., typical RRMS, BMS.

As used herein the term "informing" refers to providing to the subject the results of the diagnosis of the disease sub-class (i.e., BMS or typical RRMS). The results may be provided as a computer output and/or oral conversation with the subject.

The teachings of the invention can be also used to determine efficiency anti multiple sclerosis drugs by determining the effect of the drug(s) on the expression level of the at least one gene of the RNA polymerase I pathway.

Thus, according to an aspect of some embodiments of the invention, there is provided a method of monitoring an efficiency of an anti multiple sclerosis (MS) drug in treating a subject diagnosed with a typical relapsing remitting multiple sclerosis (RRMS) course, the method is effected by:

(a) treating the subject with the anti MS drug; and (b) comparing a level of expression of least one gene involved in the RNA polymerase I pathway in a cell of the subject following treating with the anti MS drug to a level of expression of the at least one gene in a cell of the subject prior to the treating the subject with the anti MS drug, (i) wherein a decrease above a predetermined threshold in the level of expression of the at least one gene following the treating with the anti MS drug relative to the level of expression of the at least one gene prior to the treating with the anti MS drug indicates that the anti MS drug is efficient for treating the subject;

(ii) wherein an increase above a predetermined threshold in the level of expression of the at least one gene following the treating with the anti MS drug relative to the level of expression of the at least one gene prior to the treating with the anti MS drug indicates that the anti MS drug is not efficient for treating the subject; or (iii) wherein when a level of expression of the at least one gene following the treating with the anti MS drug is identical or changed below a predetermined threshold as compared to prior to the treating with the anti MS drug then the treatment is not efficient for treating the subject.

thereby monitoring the efficiency of the anti multiple sclerosis (MS) drug in treating the subject diagnosed with the typical RRMS course.

As used herein the phrase "treating" refers to inhibiting or arresting the development of pathology [multiple sclerosis, e.g., typical RRMS] and/or causing the reduction, remission, or regression of a pathology and/or optimally curing the pathology. Those of skill in the art will understand that various methodologies and assays can be used to assess the development of pathology, and similarly, various methodologies and assays may be used to assess the reduction, remission or regression of the pathology.

According to some embodiments of the invention, treating the subject refers to changing the disease course of the subject from a typical RRMS course to a BMS course.

According to some embodiments of the invention, treating the subject refers to preventing a typical RRMS course.

As used herein the phrase "following treating with the anti MS drug" refers to any time period after administering the anti MS drug to the subject, e.g., from a few minutes to hours, or from a few days to weeks or months after drug administration.

According to some embodiments of the invention the level of expression is determined following the first dose of the anti MS drug.

According to some embodiments of the invention the level of expression is determined following any dose of the anti MS drug.

As used herein the phrase "prior to treating with the anti MS drug" refers to any time period prior administering the anti MS drug to the subject, e.g., from a few minutes to hours, or from a few days to weeks or months prior to drug administration.

According to some embodiments of the invention the level of expression is determined prior any dose of the anti MS drug (e.g., when the subject is naïve to treatment).

According to some embodiments of the invention prior to treating refers to when the subject is first diagnosed with multiple sclerosis.

According to some embodiments of the invention prior to treating refers to when the subject is suspected of having multiple sclerosis, or diagnosed with probable multiple sclerosis.

According to some embodiments of the invention prior to treating refers to upon MS disease onset.

According to some embodiments of the invention the effect of the treatment on the subject can be evaluated by monitoring the level of expression of at least one of the polynucleotides described hereinabove. For example, down-regulation in the level of RRN3 in the subject following treatment can be indicative of the positive effect of the treatment on the subject, i.e., switching from a typical RRMS to a BMS course of disease.

The teachings of the invention can be also used to predict efficiency of a drug in vitro.

Thus, according to an aspect of some embodiments of the invention there is provided an in vitro method of predicting an efficiency of an anti multiple sclerosis (MS) drug for treatment of a subject diagnosed with a typical relapsing remitting multiple sclerosis (RRMS), the method is effected by:

(a) contacting cells of the subject with a therapeutically effective amount of the anti MS drug; and (b) comparing a level of expression in the cells of at least one gene involved in the RNA polymerase I pathway following the contacting with the anti MS drug to a level of expression of the at least one gene in the cells prior to the contacting with the anti MS drug, (i) wherein a decrease above a predetermined threshold in the level of expression of the at least one gene following the contacting with the anti MS drug relative to the level of expression of the at least one gene prior to the contacting with the anti MS drug indicates that the treatment is efficient for treating the subject;

(ii) wherein an increase above a predetermined threshold in the level of expression of the at least one gene following the contacting with the anti MS drug relative to the level of expression of the at least one gene prior to the contacting with the anti MS drug indicates that the treatment is not efficient for treating the subject; or (iii) wherein when a level of expression of the at least one gene following the contacting with the anti MS drug is identical or changed below a predetermined threshold as compared to prior to the contacting with the anti MS drug then the treatment is not efficient for treating the subject.

thereby predicting the efficiency of the anti MS drug for treatment of the subject diagnosed with the typical RRMS.

Contacting cells with the anti MS drug can be performed by any in vitro conditions including for example, adding the anti MS drug to cells derived from a subject (e.g., a primary cell culture, a cell line) or to a biological sample comprising same (e.g., a fluid, liquid which comprises the cells) such that the drug is in direct contact with the cells. According to some embodiments of the invention, the cells of the subject are incubated with the anti MS drug. The conditions used for incubating the cells are selected for a time period/concentration of cells/concentration of drug/ratio between cells and drug and the like which enable the drug to induce cellular changes, such as changes in transcription and/or translation rate of specific genes, proliferation rate, differentiation, cell death, necrosis, apoptosis and the like.

Methods of monitoring cellular changes induced by the drugs are known in the art and include for example, the MTT test which is based on the selective ability of living cells to reduce the yellow salt MTT (3-(4,5-dimethylthiazolyl-2)-2,5-diphenyltetrazolium bromide) (Sigma, Aldrich St Louis, Mo., USA) to a purple-blue insoluble formazan precipitate; the BrDu assay [Cell Proliferation ELISA BrdU colorimetric kit (Roche, Mannheim, Germany]; the TUNEL assay [Roche, Mannheim, Germany]; the Annexin V assay [ApoAlert® Annexin V Apoptosis Kit (Clontech Laboratories, Inc., CA, USA)]; the Senescence associated-β-galactosidase assay (Dimri G P, Lee X, et al. 1995. A biomarker that identifies senescent human cells in culture and in aging skin in vivo. Proc Natl Acad Sci USA 92:9363-9367); as well as various RNA and protein detection methods (which detect level of expression and/or activity) which are further described hereinabove.

According to some embodiments of the invention, the cells are incubated under conditions which enable the effect of the drug on cellular processes such as downregulation of the at least one gene of the RNA polymerase I pathway.

According to an aspect of some embodiments of the invention there is provided a method of treating a subject diagnosed with multiple sclerosis, the method is effected by: (a) classifying the subject as being more likely to have BMS or typical RRMS according to the method of the invention, (b) selecting a treatment regimen based on classification results of step (a); thereby treating the subject diagnosed with multiple sclerosis.

As used herein the phrase "treatment regimen" refers to a treatment plan that specifies the type of treatment, dosage, schedule and/or duration of a treatment provided to a subject in need thereof (e.g., a subject diagnosed with MS). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., a damage to healthy cells or tissue). The dosage, schedule and duration of treatment can vary, depending on the severity of pathology and the selected type of treatment, and those of skills in the art are capable of adjusting the type of treatment with the dosage, schedule and duration of treatment.

For example, when the subject is classified as being more likely to have typical RRMS (or being diagnosed with typical RRMS) then the treatment regimen is an aggressive therapy such as an immunomodulation therapy, e.g., a high dosage of interferon beta 1a [Rebif, which can be administered subcutaneously, at a dosage of e.g., 44 µg, three times a week].

MS drugs which can be administered to a subject predicted to have an RRMS course of disease according to the present teachings include, but are not limited to Diterpenoid triepoxide Triptolide (TPT), Adderall; Ambien; Avonex; Baclofen; Beta interferon; Betaseron; Celexa; Clonazepam; Copaxone; Corticosteroids; Cymbalta; Cytoxan; Dexamethasone; Effexor; Elavil; Gabapentin; Hydrocodone; Lexapro; Lyrica; Mitoxantrone; Naltrexone; Neurontin; Novantrone; Prednisone; Provigil; Rebif; Solumedrol; Symmetrel; Topamax; Tysabri; Wellbutrin; Xanax; Zanaflex; Zoloft; Novartis' fingolimod [sphingosine 1-phosphate receptor (S1P-R) modulator]; Teva's laquinimod; Merck KGaA's Mylinax (cladribine); Sanofi-aventis' teriflunomide; Biogen Idec's BG-12 (Phase III); GSK/Mitsubishi Tanabe Pharma's firategrast; MediciNova's ibudilast; Biogen/UCB's CDP323 (Phase II).

One the other hand, when the subject is classified as being more likely to have BMS (or is diagnosed with BMS) then the aggressive treatment is not recommended, and these patients would not be treated or treatment can be delayed.

In addition, knowing the prediction or classification of MS disease course (BMS or typical RRMS) is highly beneficial in terms of saving un-necessary costs to the health system.

According to an aspect of some embodiments of the invention there is provided a method of treating a subject diagnosed with multiple sclerosis, the method is effected by (a) diagnosing a typical relapsing remitting multiple sclerosis (RRMS) according to the method of the invention, and (b) administering to the subject a therapeutically effective amount of diterpenoid triepoxide Triptolide (TPT) or a derivative thereof, thereby treating the subject TPT derivatives and preparation thereof are described in WO9852933A1, which is fully incorporated herein by reference. Non-limiting examples of TPT derivatives include, compounds of the general formulas.

Formula (1)

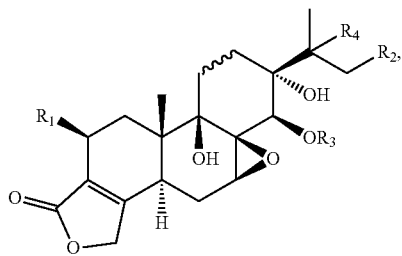

formula (2)

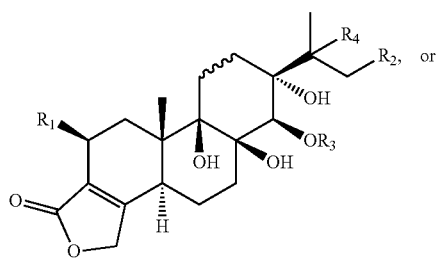

-continued formula (3)

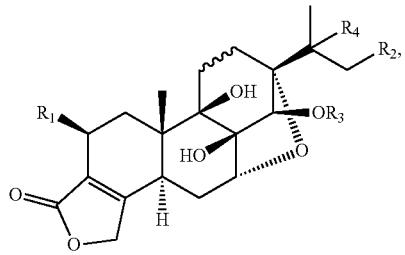

Wherein

∼ represents a single or double bond;
$R_1$ and $R_2$ each independently is H or —$OR_5$;
R3 is H, —C(═O)(CH2)nCO2H or a suitable amino acid;
$R_1$ is H or —OH; $R_1$ is H, —C(═O)(CH2)nCO2H or a suitable amino acid;
n is the integer 2, 3, 4, 5 or 6;
and the stereoisomers, enantiomers and pharmaceutically acceptable salts thereof; provided that R, and R2 are H when R, is other than H (for further details see WO9852933A1).

A commercially available preparation of Triptolide which can be used according to the teachings of the invention is Trisoxireno(4b,5:6,7:8a,9)phenanthro(1,2-c)furan-1(3H)-one, 3b,4,4a,6,6a,7a,7b,8b,9,10-decahydro-6-hydroxy-8b-methyl-6a-(1-methylethyl)-, (3bS,4aS,5aS,6R,6aR,7aS,7bS,8aS,8bS)-[CAS No.: 38748-32-2; PG490, Chengdu Biopurify Phytochemicals Ltd. Chengdu, Sichuan, China].

According to some embodiments of the invention, when the subject is more likely to have typical RRMS then the treatment regimen comprises administering to the subject an agent which downregulates the level of expression of the at least one gene involved in the RNA polymerase I pathway.

According to some embodiments of the invention, treating the subject is effected by downregulating the expression level and/or activity (RNA and/or polypeptide encoded thereby) of at least one polynucleotide of the polymerase I pathway (for details see the list of genes/polynucleotide in Table 3 in Example 1 of the Examples section which follows).

Following is a list of downregulating agents which can decrease the expression level of the gene product (RNA or protein molecules) of at least one of the polynucleotides of the polymerase I pathway.

Downregulation can be effected on the genomic and/or the transcript level using a variety of molecules which interfere with transcription and/or translation (e.g., RNA silencing agents, Ribozyme, DNAzyme and antisense), or on the protein level using e.g., an antibody, antagonists, enzymes that cleave the polypeptide and the like.

One example, of an agent capable of downregulating a polypeptide-of-interest is an antibody or antibody fragment capable of specifically binding the polypeptide-of-interest. Preferably, the antibody specifically binds at least one epitope of the polypeptide-of-interest. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments directly and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

In case the target antigen (the protein which is detected by the antibody) is presented within the cell, the antibody of the invention can be expressed within the cell intracellular antibodies (also known as "intrabodies") or a particular compartment thereof. Intrabodies are essentially SCA to which intracellular localization signals have been added (e.g., ER, mitochondrial, nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R. et al., 1994, J. Biol. Chem. 269:23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

For cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In another embodiment, the vector encodes a single chain antibody (scFv) wherein the variable regions of the light and heavy chains are linked by a flexible peptide linker [e.g., $(Gly_4Ser)_3$ and expressed as a single chain molecule. To inhibit marker activity in a cell, the expression vector encoding the intracellular antibody is introduced into the cell by standard transfection methods, as discussed hereinbefore.

Once antibodies are obtained, they may be tested for activity, for example via ELISA.

Downregulation of the polynucleotide-of-interest can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

The RNA silencing agent can be directed to a specific compartment within the cells, such as to the nucleus (see e.g., Shim M S and Kwon Y J. 2009, "Controlled cytoplasmic and nuclear localization of plasmid DNA and siRNA by differentially tailored polyethylenimine"; J. Control Release. 133:206-13, Epub 2008 Nov. 1), nucleoli, and the like.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The present invention also contemplates introduction of long ds-RNA specifically designed not to induce the interferon and PKR pathways for downregulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

A non-limiting example for an siRNA which can be used to down regulate RRN3 (RNA polymerase I transcription factor homolog) expression level in a cell of a subject is Rrn3 siRNA (h): sc-106866 (Santa Cruz Biotechnology, Inc. Santa Cruz, Calif., USA). In addition, downregulation of RRN3 can be achieved by Rrn3 shRNA plasmid (h): sc-106866-SH and Rrn3 shRNA (h) Lentiviral Particles: sc-106866-V ((Santa Cruz Biotechnology, Inc. Santa Cruz, Calif., USA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al.

(2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with the present invention can be effected as follows. First, the mRNA sequence of the polynucleotide-of-interest is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tusch1 ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm nih gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIsl, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of the present invention may be targeted to a bridging region on either side of the deletion. Introduction of such RNA silencing agents into a cell would cause a down-regulation of the mutated protein while leaving the non-mutated protein unaffected.

Another agent capable of downregulating the polynucleotide-of-interest is a DNAzyme molecule capable of specifically cleaving an mRNA transcript or DNA sequence of the polynucleotide-of-interest. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther World Wide Web (dot) asgt (dot) org). In another application, DNAzymes complementary to bcr-ab1 oncogenes were successful in inhibiting the oncogenes expression in leukemia cells, and lessening relapse rates in autologous bone marrow transplant in cases of CML and ALL.

Downregulation of the polynucleotide-of-interest can also be effected by using an antisense polynucleotide capable of specifically hybridizing with an mRNA transcript encoding the polynucleotide-of-interest.

Design of antisense molecules which can be used to efficiently downregulate the polynucleotide-of-interest must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating the polynucleotide-of-interest is a ribozyme molecule capable of specifically cleaving an mRNA transcript encoding the polynucleotide-of-interest. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

An additional method of regulating the expression of the polynucleotide-of-interest in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

Another agent capable of downregulating the expression level of the polynucleotide-of-interest is a small molecule which inhibits the activity, level and/or interactions of the gene product of polynucleotide-of-interest, such as by interfering with the pathway in which the gene product of the polynucleotide-of-interest is involved.

Non-limiting examples of small molecules which can be used along with the method of the invention to treat the subject include Cycloheximide and diterpenoid triepoxide Triptolide (TPT) or a derivative thereof.

For example, when RRN3 is upregulated in the typical RRMS subject then the treatment can be with diterpenoid triepoxide Triptolide (TPT) or a derivative thereof; and/or with Cycloheximide or a derivative thereof.

Any of the downregulating agents described hereinabove (e.g., the agent which downregulates the gene of the RNA polymerase I pathway, e.g., siRNA, antibody) can be provided to the subject in need thereof along with any of the known multiple sclerosis therapies (e.g., the anti MS drugs) described hereinabove (combination therapy) and/or with Triptolide or a derivative thereof.

Any of the downregulating agents described above can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the down-regulating agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

For example, the pharmaceutical composition may be administered using a dermal patch which releases the active ingredient [e.g., Diterpenoid triepoxide Triptolide (TPT) has a molecular weight of 360.40 and it will thus be suitable to be used in a dermal patch].

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (the downregulating agent) effective to prevent, alleviate or ameliorate symptoms of a disorder (e.g., RRMS) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to an aspect of some embodiments of the invention, there is provided a method of selecting a drug for treating a typical relapsing remitting multiple sclerosis (RRMS) in a subject, the method is effected by (a) contacting cells of a subject classified as having a typical RRMS with a plurality of drug molecules, (b) identifying at least one drug molecule which downregulates a level of expression of at least one gene involved in the RNA polymerase I pathway, the at least one drug molecule is suitable for treating the typical RRMS in the subject, thereby selecting the drug for treating the typical RRMS in the subject.

The plurality of drug molecules can be peptides, RNA, DNA, aptamers and small molecules.

According to some embodiments of the invention the polynucleotides described hereinabove (e.g., oligonucleotides) can form a part of a probeset.

According to some embodiments of the invention, the probeset comprises a plurality of oligonucleotides and no more than 50 oligonucleotides (e.g., no more than about 40, no more than about 30, e.g., no more than about 20, e.g., no more than about 15, e.g., no more than about 10 oligonucleotides) wherein an oligonucleotide of the plurality of oligonucleotides specifically recognizes a polynucleotide of at least one gene involved in the RNA polymerase pathway. For example, each of the oligonucleotides can specifically recognize a polynucleotide of the RNA polymerase I pathway.

According to some embodiments of the invention the probeset comprises a plurality of oligonucleotides and no more than 500 oligonucleotides wherein each of the plurality of oligonucleotides is capable of specifically recognizing at least one polynucleotide sequence selected from the group consisting of C22orf8, TLK1, HNRPH1, PLXDC1, TLK1, PKN2, ALS2CR8, FLJ12547, ZNF238, PDPR, NT5E, PASK, HPGD, IL6ST, JARID1A, PASK, LEF1, FLJ10246, MTUS1, FLJ14011, VSIG4, MARCH-VI, FLJ10613, EWSR1, ATP8A1, SLC4A7, FLJ21127, HNRPH1, ABLIM1, ITGA6, ADCY9, CROCC, SH3YL1, SMA4, SPTBN1, DPEP3, PDE3B, AF5Q31, NRCAM, DOCK9, IPW, FLJ20152, SIRPB2, GALNT4, CD28, TXK, ETS1, DGCR5, ZNF192, TCF7, CAMK4, SIM2, MGEA5, TGFBR2, RET, MAPK8IP3, RRN3, DKFZp547H025, FBXW11, ZNF423, DLG1, MGC17330, CD164L1, REPS1, ACHE, ITGB1BP2, LOC94431, LTK, RUNX1, EVER1, KIAA2010, CEACAM7, STX16, SLC4A5, CRTAP, RECQL5, MAGEF1, VIPR1, FLJ10979, TTC3, CRSP2, BAZ2A, GTF2I, MGC50853, KIAA0508, BPHL, LTBP4, FN3KRP, SCARB1, MGC17330, HYAL4, DGKA, FLJ11196, DHRS6, EPHB4, IDI2/GTPBP4, SNTG2, SLC7A6, PMS2L2, KIAA0436, TOSO, THRAP3, T3JAM, LOC283232, LOC92482, PTER, ATM, NUCB2, PIK3R2, MGC1136, CD59, JARID1A, FLJ39616, ABLIM1, PBP, MAPK8IP3, FTS, LHX5, TNFRSF7, MYC, PBXIP1, DATF1, HTF9C, PUS1, KIAA0924, C6orf4, KIAA0372, WDR42A, CRYZL1, TERE1, LTBP4, TTC3, NFATC1, POM121/LOC340318, TOSO, LOC348926/MGC16279/SB153/FLJ10661, SPOCK2, KIAA0515, SLC37A4, CD44, SMARCA2, SPTBN1, C6orf130, TTC3, DLG1, SLC35E2, MCCC1, PMS2L11, RCN3, STX16, FLJ20618, STAT5B, SMARCA2, SATB1, POLR1D, ASXL1, REV1L, PMS2L2/PMS2L5, FLJ12355, CCNB1IP1, FLJ12270, KIAA0692, MCM7, GPSN2, STX16, MMS19L, GTF2I/GTF2IP1, AKAP7, ZNF444, SLC35A3, MGEA5, RUTBC3, C20orf36, RAD17, ALG12, LOC112869, C6orf48, CUTC, LGTN, DEF6, WAC, HNRPH3, NS, KIAA0892, LRPPRC, HMG20A, DDX42, TINP1, ZDHHC17, C19orf2, EIF4B, LOC376745, DKFZP434C171, TH1L, C19orf13, RPL22, PHF15, EWSR1, EIF4B, FAM48A, YT521, NEK9, EIF3S7, RPS6, RPL35A, EEF2, RPL3, RPS6, UBA52, RPL6, RPS6, RPL13, AL353949, AL580863, AF052160, AW128846, AW974481, N92920, BG178274, AW303460, BF057458, AL050035, M59917, AK025422, AI693985, AU158442, AK021460, AL023773, NM_003790, AC005011, M90355, AL353580, U38964, D50683, BE967207, YWHAB, ATP6V1E1, UBB, MRLC2/MRCL3, UQCR, MRLC2, RTN4, UBE2A, RTN4, WDR1, PSMA6, C14orf123, PP1201, TBK1, CAST, CAST, RSN, PSME1, SDF2, GSTO1, CAST, DNCL1, SQRDL, ADIPOR2, ICMT, NDUFA6, NDUFA6, COX17, HIF1AN, FLJ20257, TBPL1, RAPGEF2, CRSP8, APOL1, PAOX, CNDP2, ETFA, DPP3, KPNA1, MGC3036, TUBB2, PDCL, CCL5, CDS2, RAP1GDS1, ATP6V1D, OBRGRP/LEPR, SF4, GCLC, MGST3, BICD2, BRF1, CHST12, EXOSC7, TOR1B, ZFP95, ILK, UNC13A, MTHFD2, CASP10, FLJ45850, CMRF-35H, ARF3, NDOR1, DUSP10, AP1M2, VRK2, GSN, PTRF, RBM19, RABGAP1L, ATP5S, STOM, TFPI2, SLCO3A1, PTPN12, CSF1, SIGLEC6, KIRREL, OBRGRP, TP53AP1, SUHW1, NUP98, IL15RA, MICB, CMRF-35H, SPHK1, TNFRSF6, FLJ11301, LRP5, STOM, EPHA2, SRC, FLJ11301, PSTPIP2, EBP, MCPH1, PTPRF, LIMK2, FSTL4, CBR1, MGC2654, MYCT1, NOL3, MITF, ATP10B, FBXO31, TBX21, LSS, SLC17A3, MNAB, CHPPR, GIF, VAMPS, ABCG2, KIF1B, LOH11CR2A, NID2, RBBP8, ETV7, CTSL, RUFY1, RSU1, PARD3, APOB, ACOX3, DAB2, LDLR, TJP2, GNAS, PARD3, NCKAP1, TAP2, HDGFRP3, LDLR, PIK3R3, HTR2B, GAS2L1, FER1L3, C3orf14, TP53TG3, LEPR, CLIC5, PDE4DIP, ATP9A, ITGB1BP1, INDO, SELP, FHL2, FER1L3, EGF, SIAT8A, HDGFRP3, LRAP, VWF, FLJ10134, IMP-3, DMN, MCTP1, FSTL1, CTNNAL1, RAB27B, THBS1, PROS1, MMRN1, CTTN, AL078596, AI148659, U00956 and M29383.

It will be appreciated that the isolated nucleic acid sequences included in the kit or the probeset of the present invention can be bound to a solid support e.g., a glass wafer in a specific order, i.e., in the form of a microarray. Alternatively, isolated nucleic acid sequences can be synthesized directly on the solid support using well known prior art approaches (Seo T S, et al., 2004, Proc. Natl. Acad. Sci. USA, 101: 5488-93.). In any case, the isolated nucleic acid sequences are attached to the support in a location specific manner such that each specific isolated nucleic acid sequence has a specific address on the support (i.e., an addressable location) which denotes the identity (i.e., the sequence) of that specific isolated nucleic acid sequence.

The kit may further include a positive control for an expression level of at least one of the polynucleotides of the invention (e.g., which involves in the RNA polymerase I pathway). The positive control can be any biological sample derived from a reference subject (i.e., a subject with a known course of MS, i.e., BMS or typical RRMS), a biological sample with known amount/concentration of the gene product (i.e., RNA or protein) of at least one of the polynucleotides of the invention; or a pre-determined level (amount/concentration) of purified, chemically synthesized or recombinantly generated RNA or protein molecules (gene products) of the at least one polynucleotide of the invention. The kit may further comprise instructions for use in classifying a subject as being more like to have BMS or typical RRMS, to diagnose BMS or typical RRMS, to monitor treatment efficiency, to select a treatment regimen, to treat a subject having multiple sclerosis and/or to select for drugs suitable for treating multiple sclerosis.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Subjects—

31 patients (age 44.5±1.5; female to male ratio 24:7) with BMS were characterized by mean EDSS 1.95±0.15, disease duration 17.0±1.3 years, annual EDSS rate 0.13±0.01, annual relapse rate 0.23±0.04. 36 patients (age 40.3±1.8; female to male ratio 8:3) with typical RRMS were characterized by mean EDSS 3.54±0.23, disease duration 10.9±1.4 years, annual EDSS rate 0.45±0.06, annual relapse rate 0.64±0.09.

RNA Isolation and Microarray Expression Profiling—

Peripheral blood mononuclear cells (PBMC) were separated on ficoll-hypaque gradient. Total RNA was isolated using the TRIzol Reagent (Invitrogen, Carlsbad, Calif.), and cDNA was synthesized, labeled and hybridized to HG-U133A-2 array (Affymetrix, Inc, Santa Clara, Calif.) containing 22,215 gene-transcripts, washed and scanned (Hewlett Packard, GeneArray-TM scanner G2500A) according to manufacturer's protocol Affymetrix (Inc, Santa Clara, Calif.).

Data Analysis—

Data analysis was performed using the Partek Genomics Solution software [World Wide Web (dot) partek (dot) com]. Expression values were computed from raw CEL (cell) files by applying the Robust Multi-Chip Average (RMA) background correction algorithm. The RMA correction included: 1) values background correction; 2) quantile normalization; 3) log 2 transformation; 4) median polish summarization. In order to avoid the noise caused by variable set effects each set was normalized to pre-saved distribution pattern of a well balanced set used as a reference distribution. To reduce batch effect ANOVA multiple model analysis was applied. Source of variation was analyzed; nuisance batches effects such as working batch, patient age, gender and treatment were eliminated. Most informative genes (MIGs) were defined as genes with $p<0.01$ by ANOVA linear contrasts model. For samples classification, principal component analyses (PCA) were performed.

Gene functional annotation, enrichment and pathway analysis were performed using functional classification tools, David Bioinformatics Resources [Hypertext Transfer Protocol://david (dot) abcc (dot) nciferf (dot) gov/home (dot) jsp], and Ingenuity Pathways Analysis web-software [World Wide Web (dot) ingenuity (dot) com]. Enrichment was defined as significantly ($p<0.05$) higher proportion of genes in a given gene set than expected by chance analysis. The study design is demonstrated in FIG. 1.

Example 1

Experimental Results

Identification of Differentiating Genes Between Patients with BMS and Patients with Typical RRMS—

Figure 2:
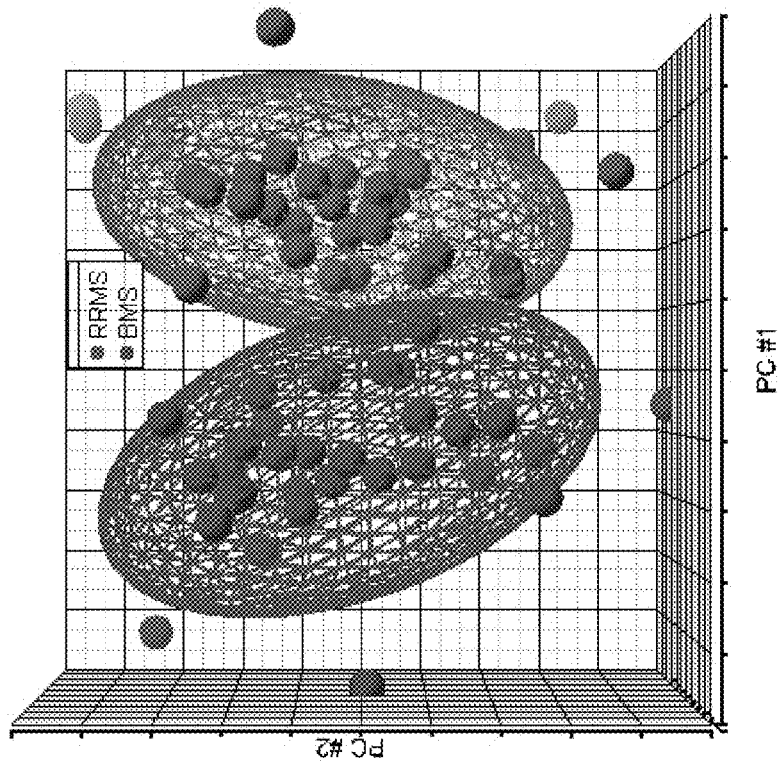
FIG. 2 depicts Principal Component Analysis (PCA) based on 406 most informative genes (MIGs)

BMS patients differentiated from typical RRMS by 406 MIGs (most informative genes), 171 genes were over-expressed (upregulated) and 235 were down-expressed (downregulated), with the log fold change ranged from −3.1 to 3.3 (FIG. 2).

Table 1 hereinbelow provides the differentiating genes between BMS and typical RRMS patients.

TABLE 1

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 216683_at | 1 | AL353949 | 407 | 6.85E−04 | −1.129 | — | — |
| 219629_at | 2 | NM_017911 | 408 | 5.51E−03 | −1.117 | C22orf8 | chromosome 22 open reading frame 8 |
| 210379_s_at | 3 | AI469203 | 409 | 7.42E−03 | −1.083 | TLK1 | tousled-like kinase 1 |
| 213472_at | 4 | AI022387 | 410 | 4.25E−03 | −1.081 | HNRPH1 | heterogeneous nuclear ribonucleoprotein H1 (H) |
| 219700_at | 5 | NM_020405 | 411 | 5.56E−05 | −1.081 | PLXDC1 | plexin domain containing 1 |
| 211077_s_at | 6 | Z25421 | 412 | 9.89E−04 | −1.080 | TLK1 | tousled-like kinase 1 /// tousled-like kinase 1 |
| 210969_at | 7 | AF118089 | 413 | 4.20E−04 | −1.078 | PKN2 | protein kinase N2 |
| 216298_at | 8 | AL580863 | 414 | 3.57E−03 | −1.075 | — | Similar to T-cell receptor gamma chain V region PT-gamma-1/2 precursor /// Simil |
| 219834_at | 9 | NM_024744 | 415 | 1.20E−03 | −1.069 | ALS2CR8 | amyotrophic lateral sclerosis 2 (juvenile) chromosome region, candidate 8 |
| 215262_at | 10 | AF052160 | 416 | 2.29E−04 | −1.068 | — | Clone 24629 mRNA sequence |
| 220715_at | 11 | NM_024992 | 417 | 1.53E−04 | −1.067 | FLJ12547 | hypothetical protein FLJ12547 |
| 207164_s_at | 12 | NM_006352 | 418 | 4.17E−03 | −1.067 | ZNF238 | zinc finger protein 238 |
| 220236_at | 13 | NM_017990 | 419 | 7.14E−04 | −1.067 | PDPR | pyruvate dehydrogenase phosphatase regulatory subunit |
| 203939_at | 14 | NM_002526 | 420 | 1.84E−03 | −1.065 | NT5E | 5′-nucleotidase, ecto (CD73) |
| 216945_x_at | 15 | U79240 | 421 | 2.45E−03 | −1.063 | PASK | PAS domain containing serine/threonine kinase |
| 203913_s_at | 16 | NM_000860 | 422 | 4.09E−03 | −1.062 | HPGD | hydroxyprostaglandin dehydrogenase 15-(NAD) |
| 204864_s_at | 17 | BE856546 | 423 | 9.98E−03 | −1.060 | IL6ST | interleukin 6 signal transducer (gp130, oncostatin M receptor) |
| 215698_at | 18 | AF007135 | 424 | 3.73E−03 | −1.057 | JARID1A | Jumonji, AT rich interactive domain 1A (RBBP2-like) |
| 213534_s_at | 19 | D50925 | 425 | 3.86E−03 | −1.056 | PASK | PAS domain containing serine/threonine kinase |
| 210948_s_at | 20 | AF294627 | 426 | 1.98E−03 | −1.056 | LEF1 | lymphoid enhancer-binding factor 1 |
| 220458_at | 21 | NM_018038 | 427 | 8.30E−03 | −1.055 | FLJ10246 | hypothetical protein FLJ10246 |
| 212093_s_at | 22 | AI695017 | 428 | 8.37E−03 | −1.052 | MTUS1 | mitochondrial tumor suppressor 1 |
| 207120_at | 23 | NM_022103 | 429 | 1.75E−03 | −1.050 | FLJ14011 | hypothetical zinc finger protein FLJ14011 |
| 204787_at | 24 | NM_007268 | 430 | 3.61E−03 | −1.050 | VSIG4 | V-set and immunoglobulin domain containing 4 |
| 215512_at | 25 | AK000970 | 431 | 1.74E−03 | −1.049 | MARCH-VI | membrane-associated RING-CH protein VI |
| 46947_at | 26 | T87245 | 432 | 1.23E−03 | −1.049 | FLJ10613 | Hypothetical protein FLJ10613 |

TABLE 1-continued

Genes which are differentially expressed in blood samples of benign multiple sclerosis
(BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 210012_s_at | 27 | BC000527 | 433 | 7.10E−03 | −1.048 | EWSR1 | Ewing sarcoma breakpoint region 1 |
| 210192_at | 28 | AB013452 | 434 | 7.32E−03 | −1.048 | ATP8A1 | ATPase, aminophospholipid transporter (APLT), Class I, type 8A, member 1 |
| 207603_at | 29 | NM_003615 | 435 | 2.30E−03 | −1.047 | SLC4A7 | solute carrier family 4, sodium bicarbonate cotransporter, member 7 |
| 218584_at | 30 | NM_024549 | 436 | 7.79E−03 | −1.047 | FLJ21127 | hypothetical protein FLJ21127 |
| 213470_s_at | 31 | BF983406 | 437 | 8.91E−03 | −1.047 | HNRPH1 | heterogeneous nuclear ribonucleoprotein H1 (H) |
| 210461_s_at | 32 | BC002448 | 438 | 1.63E−03 | −1.047 | ABLIM1 | actin binding LIM protein 1 |
| 217656_at | 33 | AW128846 | 439 | 5.27E−04 | −1.045 | — |  |
| 215177_s_at | 34 | AV733308 | 440 | 4.01E−04 | −1.045 | ITGA6 | integrin, alpha 6 |
| 204498_s_at | 35 | NM_001116 | 441 | 3.72E−04 | −1.043 | ADCY9 | adenylate cyclase 9 |
| 216419_at | 36 | AK026910 | 442 | 7.82E−03 | −1.043 | CROCC | ciliary rootlet coiled-coil, rootletin |
| 204019_s_at | 37 | NM_015677 | 443 | 1.11E−03 | −1.043 | SH3YL1 | SH3 domain containing, Ysc84-like 1 (*S. cerevisiae*) |
| 214850_at | 38 | X75940 | 444 | 4.48E−03 | −1.043 | SMA4 | SMA4 |
| 200672_x_at | 39 | NM_003128 | 445 | 1.59E−03 | −1.043 | SPTBN1 | spectrin, beta, non-erythrocytic 1 |
| 220179_at | 40 | NM_022357 | 446 | 1.40E−03 | −1.042 | DPEP3 | dipeptidase 3 |
| 208591_s_at | 41 | NM_000922 | 447 | 6.54E−05 | −1.042 | PDE3B | phosphodiesterase 3B, cGMP-inhibited |
| 219199_at | 42 | NM_014423 | 448 | 5.72E−03 | −1.042 | AF5Q31 | ALL1 fused gene from 5q31 |
| 216959_x_at | 43 | U55258 | 449 | 1.65E−03 | −1.041 | NRCAM | neuronal cell adhesion molecule |
| 215041_s_at | 44 | BE259050 | 450 | 6.36E−03 | −1.040 | DOCK9 | dedicator of cytokinesis 9 |
| 213447_at | 45 | AI672541 | 451 | 5.32E−05 | −1.040 | IPW | imprinted in Prader-Willi syndrome |
| 218532_s_at | 46 | NM_019000 | 452 | 4.80E−03 | −1.040 | FLJ20152 | hypothetical protein FLJ20152 |
| 220485_s_at | 47 | NM_018556 | 453 | 1.56E−03 | −1.039 | SIRPB2 | signal-regulatory protein beta 2 |
| 220442_at | 48 | NM_003774 | 454 | 8.94E−03 | −1.039 | GALNT4 | UDP-N-acetyl-alpha-D-galactosamine: polypeptide N-acetylgalactosaminyltransferase |
| 211856_x_at | 49 | AF222341 | 455 | 9.84E−03 | −1.039 | CD28 | CD28 antigen (Tp44) |
| 206828_at | 50 | NM_003328 | 456 | 1.62E−03 | −1.039 | TXK | TXK tyrosine kinase |
| 214447_at | 51 | NM_005238 | 457 | 3.28E−03 | −1.038 | ETS1 | v-ets erythroblastosis virus E26 oncogene homolog 1 (avian) |
| 215244_at | 52 | AI479306 | 458 | 6.97E−03 | −1.038 | DGCR5 | DiGeorge syndrome critical region gene 5 (non-coding) |
| 206579_at | 53 | NM_006298 | 459 | 5.64E−03 | −1.038 | ZNF192 | zinc finger protein 192 |
| 205254_x_at | 54 | AW027359 | 460 | 3.05E−03 | −1.038 | TCF7 | transcription factor 7 (T-cell specific, HMG-box) |
| 210349_at | 55 | L24959 | 461 | 3.07E−03 | −1.037 | CAMK4 | calcium/calmodulin-dependent protein kinase IV |

TABLE 1-continued

Genes which are differentially expressed in blood samples of benign multiple sclerosis
(BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 208157_at | 56 | NM_009586 | 462 | 9.47E−03 | −1.037 | SIM2 | single-minded homolog 2 (Drosophila) |
| 214972_at | 57 | AU144791 | 463 | 4.25E−03 | −1.037 | MGEA5 | Meningioma expressed antigen 5 (hyaluronidase) |
| 207334_s_at | 58 | NM_003242 | 464 | 2.70E−03 | −1.037 | TGFBR2 | transforming growth factor, beta receptor II (70/80 kDa) |
| 217666_at | 59 | AW974481 | 465 | 1.06E−03 | −1.037 | — | — |
| 215771_x_at | 60 | X15786 | 466 | 1.14E−03 | −1.036 | RET | ret proto-oncogene (multiple endocrine neoplasia and medullary thyroid carcinoma |
| 216139_s_at | 61 | AL031718 | 467 | 7.40E−03 | −1.036 | MAPK8IP3 | mitogen-activated protein kinase 8 interacting protein 3 |
| 216902_s_at | 62 | AF001549 | 468 | 4.86E−05 | −1.036 | RRN3 | RRN3 RNA polymerase I transcription factor homolog (yeast) |
| 208265_at | 63 | NM_020161 | 469 | 6.06E−04 | −1.036 | DKFZp547H025 | hypothetical protein DKFZp547H025 |
| 209456_s_at | 64 | AB033281 | 470 | 3.49E−03 | −1.036 | FBXW11 | F-box and WD-40 domain protein 11 |
| 217237_at | 65 | Y10615 | 471 | 7.72E−03 | −1.035 | ZNF423 | Zinc finger protein 423 |
| 217208_s_at | 66 | AL121981 | 472 | 2.91E−03 | −1.035 | DLG1 | discs, large homolog 1 (Drosophila) |
| 221757_at | 67 | BE042976 | 473 | 1.83E−04 | −1.035 | MGC17330 | HGFL gene /// HGFL gene |
| 213481_at | 68 | N92920 | 474 | 4.47E−03 | −1.035 | — | — |
| 219025_at | 69 | NM_020404 | 475 | 2.84E−03 | −1.035 | CD164L1 | CD164 sialomucin-like 1 |
| 215201_at | 70 | AW166925 | 476 | 9.15E−03 | −1.034 | REPS1 | RALBP1 associated Eps domain containing 1 |
| 205378_s_at | 71 | NM_015831 | 477 | 6.79E−03 | −1.034 | ACHE | acetylcholinesterase (YT blood group) |
| 219829_at | 72 | NM_012278 | 478 | 6.24E−03 | −1.033 | ITGB1BP2 | integrin beta 1 binding protein (melusin) 2 |
| 216908_x_at | 73 | AF001549 | 468 | 6.22E−04 | −1.033 | LOC94431 | similar to RNA polymerase I transcription factor RRN3 |
| 217184_s_at | 74 | X52213 | 479 | 4.40E−03 | −1.033 | LTK | leukocyte tyrosine kinase |
| 211181_x_at | 75 | AF312386 | 480 | 4.63E−03 | −1.033 | RUNX1 | runt-related transcription factor 1 (acute myeloid leukemia 1; aml1 oncogene) |
| 214958_s_at | 76 | AK021738 | 481 | 1.62E−03 | −1.033 | EVER1 | epidermodysplasia verruciformis 1 |
| 220369_at | 77 | NM_017936 | 482 | 7.90E−03 | −1.033 | KIAA2010 | KIAA2010 |
| 211848_s_at | 78 | AF006623 | 483 | 8.77E−04 | −1.033 | CEACAM7 | carcinoembryonic antigen-related cell adhesion molecule 7 |
| 221638_s_at | 79 | AF008937 | 484 | 8.81E−03 | −1.033 | STX16 | syntaxin 16 |
| 221723_s_at | 80 | AF243499 | 485 | 8.08E−03 | −1.033 | SLC4A5 | solute carrier family 4, sodium bicarbonate cotransporter, member 5 |
| 201380_at | 81 | NM_006371 | 486 | 8.45E−04 | −1.032 | CRTAP | cartilage associated protein |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 34063_at | 82 | AB006533 | 487 | 1.03E−03 | −1.032 | RECQL5 | RecQ protein-like 5 |
| 214757_at | 83 | BG178274 | 488 | 5.20E−03 | −1.032 | — | Hypothetical gene supported by AK024602 |
| 218176_at | 84 | NM_022149 | 489 | 4.04E−03 | −1.032 | MAGEF1 | melanoma antigen, family F, 1 |
| 221977_at | 85 | AW303460 | 490 | 7.35E−03 | −1.032 | — | — |
| 214161_at | 86 | BF057458 | 491 | 9.56E−03 | −1.031 | — | — |
| 214857_at | 87 | AL050035 | 492 | 6.21E−03 | −1.031 | — | MRNA; cDNA DKFZp566H0124 (from clone DKFZp566H0124) |
| 216230_x_at | 88 | M59917 | 493 | 1.74E−03 | −1.031 | — | — |
| 205019_s_at | 89 | NM_004624 | 494 | 3.56E−03 | −1.031 | VIPR1 | vasoactive intestinal peptide receptor 1 |
| 221707_s_at | 90 | BC006116 | 495 | 7.60E−03 | −1.031 | FLJ10979 | hypothetical protein FLJ10979 /// hypothetical protein FLJ10979 |
| 208664_s_at | 91 | AU131711 | 496 | 1.15E−04 | −1.030 | TTC3 | tetratricopeptide repeat domain 3 |
| 215167_at | 92 | BE567032 | 497 | 8.69E−03 | −1.030 | CRSP2 | cofactor required for Sp1 transcriptional activation, subunit 2, 150 kDa |
| 215437_x_at | 93 | BE513659 | 498 | 4.06E−03 | −1.030 | BAZ2A | bromodomain adjacent to zinc finger domain, 2A |
| 210892_s_at | 94 | BC004472 | 499 | 3.77E−03 | −1.029 | GTF2I | general transcription factor II, i |
| 212400_at | 95 | AL043266 | 500 | 1.57E−03 | −1.029 | MGC50853 | hypothetical protein MGC50853 |
| 215137_at | 96 | H92070 | 501 | 5.46E−03 | −1.029 | KIAA0508 | KIAA0508 protein |
| 205750_at | 97 | NM_004332 | 502 | 1.95E−03 | −1.028 | BPHL | biphenyl hydrolase-like (serine hydrolase; breast epithelial mucin-associated an |
| 210628_x_at | 98 | AF051344 | 503 | 1.93E−03 | −1.028 | LTBP4 | latent transforming growth factor beta binding protein 4 |
| 218210_at | 99 | NM_024619 | 504 | 1.42E−03 | −1.028 | FN3KRP | fructosamine-3-kinase-related protein |
| 216784_at | 100 | AK025422 | 505 | 2.68E−03 | −1.028 | — | Transcribed locus, weakly similar to XP_375174.1 hypothetical gene supported by |
| 201819_at | 101 | NM_005505 | 506 | 7.48E−03 | −1.028 | SCARB1 | scavenger receptor class B, member 1 |
| 214312_at | 102 | AI693985 | 507 | 2.93E−03 | −1.028 | — | — |
| 215556_at | 103 | AU158442 | 508 | 3.90E−03 | −1.028 | — | — |
| 221756_at | 104 | BE042976 | 473 | 2.52E−03 | −1.027 | MGC17330 | HGFL gene /// HGFL gene |
| 216909_at | 105 | AK021460 | 509 | 5.34E−03 | −1.027 | — | — |
| 220249_at | 106 | NM_012269 | 510 | 8.17E−03 | −1.027 | HYAL4 | hyaluronoglucosaminidase 4 |
| 211272_s_at | 107 | AF064771 | 511 | 3.46E−03 | −1.027 | DGKA | diacylglycerol kinase, alpha 80 kDa |
| 218651_s_at | 108 | NM_018357 | 512 | 7.30E−03 | −1.027 | FLJ11196 | acheron |
| 218285_s_at | 109 | NM_020139 | 513 | 2.93E−03 | −1.027 | DHRS6 | dehydrogenase/reductase (SDR family) member 6 |
| 217385_at | 110 | AL023773 | 514 | 2.79E−03 | −1.027 | — | — |
| 202894_at | 111 | NM_004444 | 515 | 1.52E−03 | −1.026 | EPHB4 | EPH receptor B4 |
| 217631_at | 112 | AI081107 | 516 | 6.97E−03 | −1.026 | IDI2 /// GTPBP4 | isopentenyl-diphosphate delta isomerase 2 /// GTP binding protein 4 |

TABLE 1-continued

Genes which are differentially expressed in blood samples of benign multiple sclerosis
(BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 220487_at | 113 | NM_018968 | 517 | 9.34E−03 | −1.026 | SNTG2 | syntrophin, gamma 2 |
| 203579_s_at | 114 | AI660619 | 518 | 1.98E−03 | −1.026 | SLC7A6 | solute carrier family 7 (cationic amino acid transporter, y+ system), member 6 |
| 215412_x_at | 115 | AB017007 | 519 | 7.10E−04 | −1.026 | PMS2L2 | postmeiotic segregation increased 2-like 2 |
| 212217_at | 116 | AU154782 | 520 | 1.32E−03 | −1.026 | KIAA0436 | putative prolyl oligopeptidase |
| 221602_s_at | 117 | AI084226 | 521 | 3.58E−04 | −1.026 | TOSO | regulator of Fas-induced apoptosis /// regulator of Fas-induced apoptosis |
| 217847_s_at | 118 | NM_005119 | 522 | 8.43E−03 | −1.025 | THRAP3 | thyroid hormone receptor associated protein 3 |
| 215275_at | 119 | AW963138 | 523 | 9.31E−03 | −1.025 | T3JAM | TRAF3-interacting Jun N-terminal kinase (JNK)-activating modulator |
| 221951_at | 120 | AI739035 | 524 | 2.65E−03 | −1.025 | LOC283232 | hypothetical protein LOC283232 |
| 213224_s_at | 121 | AK025724 | 525 | 7.84E−05 | −1.024 | LOC92482 | Hypothetical protein LOC92482 |
| 218967_s_at | 122 | BF112019 | 526 | 5.08E−03 | −1.024 | PTER | phosphotriesterase related |
| 208442_s_at | 123 | NM_000051 | 527 | 9.87E−04 | −1.024 | ATM | ataxia telangiectasia mutated (includes complementation groups A, C and D) |
| 203675_at | 124 | NM_005013 | 528 | 5.38E−03 | −1.024 | NUCB2 | nucleobindin 2 |
| 207105_s_at | 125 | NM_005027 | 529 | 2.15E−03 | −1.023 | PIK3R2 | phosphoinositide-3-kinase, regulatory subunit 2 (p85 beta) |
| 219144_at | 126 | NM_024025 | 530 | 3.23E−03 | −1.023 | MGC1136 | hypothetical protein MGC1136 |
| 212463_at | 127 | BE379006 | 531 | 9.58E−03 | −1.023 | CD59 | CD59 antigen p18-20 (antigen identified by monoclonal antibodies 16.3A5, EJ16, E |
| 202040_s_at | 128 | NM_005056 | 532 | 8.73E−03 | −1.023 | JARID1A | Jumonji, AT rich interactive domain 1A (RBBP2-like) |
| 64432_at | 129 | W05463 | 533 | 4.53E−03 | −1.023 | FLJ39616 | apoptosis related protein PNAS-1 |
| 200965_s_at | 130 | NM_006720 | 534 | 2.98E−03 | −1.022 | ABLIM1 | actin binding LIM protein 1 |
| 205353_s_at | 131 | NM_002567 | 535 | 9.67E−03 | −1.022 | PBP | prostatic binding protein |
| 213177_at | 132 | AB028989 | 536 | 9.13E−03 | −1.022 | MAPK8IP3 | mitogen-activated protein kinase 8 interacting protein 3 |
| 218373_at | 133 | NM_022476 | 537 | 6.35E−03 | −1.022 | FTS | fused toes homolog (mouse) |
| 208333_at | 134 | NM_022363 | 538 | 4.11E−03 | −1.022 | LHX5 | LIM homeobox 5 |
| 206150_at | 135 | NM_001242 | 539 | 8.17E−03 | −1.022 | TNFRSF7 | tumor necrosis factor receptor superfamily, member 7 /// tumor necrosis factor r |
| 202431_s_at | 136 | NM_002467 | 540 | 7.39E−03 | −1.022 | MYC | v-myc myelocytomatosis viral oncogene homolog (avian) |
| 207838_x_at | 137 | NM_020524 | 541 | 3.63E−03 | −1.021 | PBXIP1 | pre-B-cell leukemia transcription factor interacting protein 1 |

TABLE 1-continued

Genes which are differentially expressed in blood samples of benign multiple sclerosis
(BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 218325_s_at | 138 | NM_022105 | 542 | 1.46E−03 | −1.021 | DATF1 | death associated transcription factor 1 |
| 218475_at | 139 | NM_022727 | 543 | 1.53E−03 | −1.021 | HTF9C | HpaII tiny fragments locus 9C |
| 218670_at | 140 | NM_025215 | 544 | 1.05E−03 | −1.021 | PUS1 | pseudouridylate synthase 1 |
| 205594_at | 141 | NM_014897 | 545 | 8.79E−03 | −1.021 | KIAA0924 | KIAA0924 protein |
| 215411_s_at | 142 | AL008730 | 546 | 7.21E−03 | −1.021 | C6orf4 | chromosome 6 open reading frame 4 |
| 203048_s_at | 143 | NM_014639 | 547 | 2.14E−03 | −1.020 | KIAA0372 | KIAA0372 |
| 216885_s_at | 144 | AK026481 | 548 | 4.07E−04 | −1.020 | WDR42A | WD repeat domain 42A |
| 219767_s_at | 145 | NM_005111 | 549 | 3.79E−03 | −1.020 | CRYZL1 | crystallin, zeta (quinone reductase)-like 1 |
| 219131_at | 146 | NM_013319 | 550 | 3.21E−03 | −1.020 | TERE1 | transitional epithelia response protein |
| 213176_s_at | 147 | AI910869 | 551 | 6.21E−03 | −1.020 | LTBP4 | latent transforming growth factor beta binding protein 4 |
| 208661_s_at | 148 | D84294 | 552 | 4.85E−03 | −1.020 | TTC3 | tetratricopeptide repeat domain 3 |
| 208196_x_at | 149 | NM_006162 | 553 | 9.44E−03 | −1.020 | NFATC1 | nuclear factor of activated T-cells, cytoplasmic, calcineurin-dependent 1 |
| 212178_s_at | 150 | AK022555 | 554 | 2.95E−03 | −1.020 | POM121 /// LOC340318 | POM121 membrane glycoprotein (rat) /// hypothetical protein LOC340318 |
| 221601_s_at | 151 | AI084226 | 521 | 2.54E−03 | −1.020 | TOSO | regulator of Fas-induced apoptosis /// regulator of Fas-induced apoptosis |
| 222013_x_at | 152 | BE348837 | 555 | 5.16E−03 | −1.019 | LOC348926 /// MGC16279 /// SB153 /// FLJ10661 | hypothetical protein LOC348926 /// hypothetical protein MGC16279 /// hypothetica |
| 202524_s_at | 153 | AI952009 | 556 | 5.43E−03 | −1.019 | SPOCK2 | sparc/osteonectin, cwcv and kazal-like domains proteoglycan (testican) 2 |
| 212068_s_at | 154 | AB011087 | 557 | 9.23E−03 | −1.019 | KIAA0515 | KIAA0515 |
| 202830_s_at | 155 | NM_001467 | 558 | 5.82E−03 | −1.019 | SLC37A4 | solute carrier family 37 (glycerol-6-phosphate transporter), member 4 |
| 209835_x_at | 156 | BC004372 | 559 | 5.79E−03 | −1.019 | CD44 | CD44 antigen (homing function and Indian blood group system) |
| 212257_s_at | 157 | AW131754 | 560 | 1.51E−03 | −1.019 | SMARCA2 | SWI/SNF related, matrix associated, actin dependent regulator of chromatin, subf |
| 212071_s_at | 158 | BE968833 | 561 | 2.68E−03 | −1.019 | SPTBN1 | spectrin, beta, non-erythrocytic 1 |
| 213322_at | 159 | AL031778 | 562 | 8.31E−04 | −1.019 | C6orf130 | chromosome 6 open reading frame 130 |
| 210645_s_at | 160 | D83077 | 563 | 2.20E−03 | −1.019 | TTC3 | tetratricopeptide repeat domain 3 |
| 202514_at | 161 | AW139131 | 564 | 4.70E−03 | −1.018 | DLG1 | DKFZP586B0319 protein |
| 217122_s_at | 162 | AL031282 | 565 | 4.05E−03 | −1.018 | SLC35E2 | solute carrier family 35, member E2 |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 218440_at | 163 | NM_020166 | 566 | 9.21E−05 | −1.018 | MCCC1 | methylcrotonoyl-Coenzyme A carboxylase 1 (alpha) |
| 210707_x_at | 164 | U38980 | 567 | 3.76E−04 | −1.018 | PMS2L11 | postmeiotic segregation increased 2-like 11 |
| 61734_at | 165 | AI797684 | 568 | 3.19E−03 | −1.018 | RCN3 | reticulocalbin 3, EF-hand calcium binding domain |
| 221500_s_at | 166 | AK026970 | 569 | 1.50E−04 | −1.018 | STX16 | syntaxin 16 |
| 219422_at | 167 | NM_0003790 | 570 | 6.24E−03 | −1.018 | — | — |
| 222244_s_at | 168 | AK000749 | 571 | 5.14E−03 | −1.018 | FLJ20618 | hypothetical protein FLJ20618 |
| 212550_at | 169 | AI149535 | 572 | 1.46E−03 | −1.018 | STAT5B | signal transducer and activator of transcription 5B |
| 206544_x_at | 170 | NM_003070 | 573 | 5.64E−03 | −1.018 | SMARCA2 | SWI/SNF related, matrix associated, actin dependent regulator of chromatin, subf |
| 216380_x_at | 171 | AC005011 | 574 | 3.97E−03 | −1.018 | — | — |
| 203408_s_at | 172 | NM_002971 | 575 | 6.31E−03 | −1.018 | SATB1 | special AT-rich sequence binding protein 1 (binds to nuclear matrix/scaffold-ass |
| 218258_at | 173 | NM_015972 | 576 | 2.71E−03 | −1.017 | POLR1D | polymerase (RNA) I polypeptide D, 16 kDa |
| 212234_at | 174 | AL034550 | 577 | 5.94E−03 | −1.017 | ASXL1 | additional sex combs like 1 (*Drosophila*) |
| 217461_x_at | 175 | M90355 | 578 | 7.56E−03 | −1.017 | — | — |
| 218428_s_at | 176 | NM_016316 | 579 | 8.87E−03 | −1.017 | REV1L | REV1-like (yeast) |
| 215667_x_at | 177 | AI375694 | 580 | 1.00E−03 | −1.017 | PMS2L2 /// PMS2L5 | postmeiotic segregation increased 2-like 2 /// postmeiotic segregation increased |
| 220465_at | 178 | NM_024988 | 581 | 2.08E−03 | −1.017 | FLJ12355 | hypothetical protein FLJ12355 |
| 217988_at | 179 | NM_021178 | 582 | 9.05E−03 | −1.017 | CCNB1IP1 | cyclin B1 interacting protein 1 |
| 221981_s_at | 180 | AA702154 | 583 | 3.45E−03 | −1.017 | FLJ12270 | hypothetical protein FLJ12270 |
| 212201_at | 181 | AW274877 | 584 | 5.96E−03 | −1.017 | KIAA0692 | KIAA0692 protein |
| 208795_s_at | 182 | D55716 | 585 | 1.81E−03 | −1.017 | MCM7 | MCM7 minichromosome maintenance deficient 7 (*S. cerevisiae*) |
| 208336_s_at | 183 | NM_004868 | 586 | 5.33E−03 | −1.017 | GPSN2 | glycoprotein, synaptic 2 |
| 221499_s_at | 184 | AK026970 | 569 | 8.49E−03 | −1.017 | STX16 | syntaxin 16 |
| 202167_s_at | 185 | NM_022362 | 587 | 8.82E−03 | −1.017 | MMS19L | MMS19-like (MET18 homolog, *S. cerevisiae*) |
| 201065_s_at | 186 | NM_001518 | 588 | 4.02E−03 | −1.017 | GTF2I /// GTF2IP1 | general transcription factor II, i /// general transcription factor II, i, pseud |
| 211172_x_at | 187 | AF161075 | 589 | 2.00E−03 | −1.017 | AKAP7 | A kinase (PRKA) anchor protein 7 |
| 218707_at | 188 | NM_018337 | 590 | 7.16E−03 | −1.016 | ZNF444 | zinc finger protein 444 |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 206770_s_at | 189 | NM_012243 | 591 | 9.43E−03 | −1.016 | SLC35A3 | solute carrier family 35 (UDP-N-acetylglucosamine (UDP-GlcNAc) transporter), mem |
| 200898_s_at | 190 | AK002091 | 592 | 2.97E−03 | −1.016 | MGEA5 | meningioma expressed antigen 5 (hyaluronidase) |
| 215519_x_at | 191 | AI081779 | 593 | 3.72E−03 | −1.016 | RUTBC3 | RUN and TBC1 domain containing 3 |
| 212406_s_at | 192 | AB028973 | 594 | 4.48E−03 | −1.016 | C20orf36 | chromosome 20 open reading frame 36 |
| 210826_x_at | 193 | AF098533 | 595 | 4.28E−03 | −1.015 | RAD17 | RAD17 homolog (*S. pombe*) |
| 218444_at | 194 | NM_024105 | 596 | 6.99E−03 | −1.015 | ALG12 | asparagine-linked glycosylation 12 homolog (yeast, alpha-1,6-mannosyltransferase |
| 221822_at | 195 | BE544663 | 597 | 4.91E−03 | −1.015 | LOC112869 | hypothetical protein BC011981 |
| 220755_s_at | 196 | NM_016947 | 598 | 7.95E−04 | −1.015 | C6orf48 | chromosome 6 open reading frame 48 |
| 218970_s_at | 197 | NM_015960 | 599 | 9.75E−03 | −1.015 | CUTC | cutC copper transporter homolog (*E. coli*) |
| 218253_s_at | 198 | NM_006893 | 600 | 5.75E−03 | −1.015 | LGTN | ligatin |
| 221293_s_at | 199 | NM_022047 | 601 | 2.42E−03 | −1.015 | DEF6 | differentially expressed in FDCP 6 homolog (mouse) |
| 217742_s_at | 200 | NM_016628 | 602 | 5.14E−03 | −1.015 | WAC | WW domain containing adaptor with coiled-coil |
| 207127_s_at | 201 | NM_021644 | 603 | 4.06E−03 | −1.014 | HNRPH3 | heterogeneous nuclear ribonucleoprotein H3 (2H9) |
| 217850_at | 202 | NM_014366 | 604 | 5.81E−03 | −1.014 | NS | nucleostemin |
| 212505_s_at | 203 | AL110250 | 605 | 8.73E−03 | −1.014 | KIAA0892 | KIAA0892 |
| 211971_s_at | 204 | AI653608 | 606 | 2.30E−05 | −1.014 | LRPPRC | leucine-rich PPR-motif containing |
| 216387_x_at | 205 | AL353580 | 607 | 5.15E−03 | −1.014 | — | — |
| 218152_at | 206 | NM_018200 | 608 | 8.22E−03 | −1.014 | HMG20A | high-mobility group 20A |
| 201788_at | 207 | NM_007372 | 609 | 4.77E−03 | −1.014 | DDX42 | DEAD (Asp-Glu-Ala-Asp) box polypeptide 42 |
| 201922_at | 208 | NM_014886 | 610 | 6.30E−03 | −1.014 | TINP1 | TGF beta-inducible nuclear protein 1 |
| 212982_at | 209 | AI621223 | 611 | 4.57E−03 | −1.014 | ZDHHC17 | zinc finger, DHHC domain containing 17 |
| 214173_x_at | 210 | AW514900 | 612 | 2.20E−04 | −1.014 | C19orf2 | chromosome 19 open reading frame 2 |
| 211937_at | 211 | NM_001417 | 613 | 3.24E−03 | −1.014 | EIF4B | eukaryotic translation initiation factor 4B |
| 216843_x_at | 212 | U38964 | 614 | 6.22E−03 | −1.014 | — | — |
| 212854_x_at | 213 | AB051480 | 615 | 1.60E−03 | −1.013 | LOC376745 | AG1 |
| 212886_at | 214 | AL080169 | 616 | 4.76E−03 | −1.013 | DKFZP434C171 | DKFZP434C171 protein |
| 220607_x_at | 215 | NM_016397 | 617 | 3.15E−03 | −1.012 | TH1L | TH1-like (*Drosophila*) |
| 212132_at | 216 | AL117499 | 618 | 5.52E−04 | −1.011 | C19orf13 | chromosome 19 open reading frame 13 |
| 214042_s_at | 217 | AW071997 | 619 | 3.11E−03 | −1.011 | RPL22 | ribosomal protein L22 |
| 212660_at | 218 | AI735639 | 620 | 5.22E−03 | −1.011 | PHF15 | PHD finger protein 15 |
| 208944_at | 219 | D50683 | 621 | 5.54E−03 | −1.011 | — | — |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 210011_s_at | 220 | BC000527 | 433 | 9.77E−03 | −1.010 | EWSR1 | Ewing sarcoma breakpoint region 1 |
| 211938_at | 221 | BF247371 | 622 | 8.55E−03 | −1.010 | EIF4B | eukaryotic translation initiation factor 4B |
| 220408_x_at | 222 | NM_017569 | 623 | 6.06E−03 | −1.010 | FAM48A | family with sequence similarity 48, member A |
| 212114_at | 223 | BE967207 | 624 | 9.73E−03 | −1.010 | — | Similar to microtubule-associated proteins 1A/1B light chain 3 |
| 212455_at | 224 | N36997 | 625 | 2.91E−03 | −1.009 | YT521 | splicing factor YT521-B |
| 212299_at | 225 | AL117502 | 626 | 6.14E−03 | −1.009 | NEK9 | NIMA (never in mitosis gene a)-related kinase 9 |
| 200005_at | 226 | NM_003753 | 627 | 4.23E−03 | −1.008 | EIF3S7 | eukaryotic translation initiation factor 3, subunit 7 zeta, 66/67 kDa /// eukaryo |
| 200081_s_at | 227 | BE741754 | 628 | 1.02E−03 | −1.007 | RPS6 | ribosomal protein S6 /// ribosomal protein S6 |
| 213687_s_at | 228 | BE968801 | 629 | 8.26E−03 | −1.006 | RPL35A | ribosomal protein L35a |
| 204102_s_at | 229 | NM_001961 | 630 | 5.59E−03 | −1.006 | EEF2 | eukaryotic translation elongation factor 2 |
| 211666_x_at | 230 | L22453 | 631 | 6.17E−03 | −1.006 | RPL3 | ribosomal protein L3 /// ribosomal protein L3 |
| 209134_s_at | 231 | BC000524 | 632 | 1.77E−03 | −1.005 | RPS6 | ribosomal protein S6 |
| 221700_s_at | 232 | AF348700 | 633 | 2.98E−04 | −1.005 | UBA52 | ubiquitin A-52 residue ribosomal protein fusion product 1 /// ubiquitin A-52 res |
| 200034_s_at | 233 | NM_000970 | 634 | 9.34E−03 | −1.005 | RPL6 | ribosomal protein L6 /// ribosomal protein L6 |
| 201254_x_at | 234 | NM_001010 | 635 | 7.37E−03 | −1.004 | RPS6 | ribosomal protein S6 |
| 212734_x_at | 235 | AI186735 | 636 | 8.06E−03 | −1.003 | RPL13 | ribosomal protein L13 |
| 217718_s_at | 236 | NM_014052 | 637 | 6.36E−03 | 1.005 | YWHAB | tyrosine 3-monooxygenase/tryptophan 5-monooxygenase activation protein, beta pol |
| 208678_at | 237 | BC004443 | 638 | 8.57E−03 | 1.006 | ATP6V1E1 | ATPase, H+ transporting, lysosomal 31 kDa, V1 subunit E isoform 1 |
| 200633_at | 238 | NM_018955 | 639 | 2.94E−03 | 1.006 | UBB | ubiquitin B /// ubiquitin B |
| 201318_s_at | 239 | NM_006471 | 640 | 1.52E−03 | 1.007 | MRLC2 /// MRCL3 | myosin regulatory light chain MRLC2 /// myosin regulatory light chain MRCL3 |
| 202090_s_at | 240 | NM_006830 | 641 | 3.41E−03 | 1.008 | UQCR | ubiquinol-cytochrome c reductase (6.4 kD) subunit |
| 221474_at | 241 | U26162 | 642 | 7.75E−03 | 1.008 | MRLC2 | myosin regulatory light chain MRLC2 |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 214629_x_at | 242 | AF320999 | 643 | 3.29E−03 | 1.009 | RTN4 | reticulon 4 |
| 200067_x_at | 243 | AL078596 | 644 | 9.11E−03 | 1.010 | — | — |
| 201899_s_at | 244 | NM_003336 | 645 | 8.17E−03 | 1.010 | UBE2A | ubiquitin-conjugating enzyme E2A (RAD6 homolog) |
| 210968_s_at | 245 | AF333336 | 646 | 3.86E−03 | 1.010 | RTN4 | reticulon 4 |
| 200609_s_at | 246 | NM_017491 | 647 | 5.41E−04 | 1.010 | WDR1 | WD repeat domain 1 |
| 208805_at | 247 | BC002979 | 648 | 3.97E−03 | 1.011 | PSMA6 | proteasome (prosome, macropain) subunit, alpha type, 6 |
| 218571_s_at | 248 | NM_014169 | 649 | 5.41E−03 | 1.011 | C14orf123 | chromosome 14 open reading frame 123 |
| 217730_at | 249 | NM_022152 | 650 | 5.26E−03 | 1.013 | PP1201 | PP1201 protein |
| 218520_at | 250 | NM_013254 | 651 | 9.23E−03 | 1.013 | TBK1 | TANK-binding kinase 1 |
| 208908_s_at | 251 | AF327443 | 652 | 7.99E−03 | 1.014 | CAST | calpastatin |
| 207467_x_at | 252 | NM_001750 | 653 | 8.54E−03 | 1.014 | CAST | calpastatin |
| 201975_at | 253 | NM_002956 | 654 | 5.39E−03 | 1.015 | RSN | restin (Reed-Steinberg cell-expressed intermediate filament-associated protein) |
| 200814_at | 254 | NM_006263 | 655 | 2.49E−04 | 1.015 | PSME1 | proteasome (prosome, macropain) activator subunit 1 (PA28 alpha) |
| 203090_at | 255 | NM_006923 | 656 | 4.45E−03 | 1.015 | SDF2 | stromal cell-derived factor 2 |
| 201470_at | 256 | NM_004832 | 657 | 2.35E−03 | 1.015 | GSTO1 | glutathione S-transferase omega 1 |
| 212586_at | 257 | AA195244 | 658 | 6.42E−03 | 1.016 | CAST | calpastatin |
| 200703_at | 258 | NM_003746 | 659 | 5.88E−03 | 1.016 | DNCL1 | dynein, cytoplasmic, light polypeptide 1 |
| 217995_at | 259 | NM_021199 | 660 | 9.02E−03 | 1.016 | SQRDL | sulfide quinone reductase-like (yeast) |
| 201346_at | 260 | NM_024551 | 661 | 3.81E−03 | 1.016 | ADIPOR2 | adiponectin receptor 2 |
| 201609_x_at | 261 | AL578502 | 662 | 1.36E−03 | 1.016 | ICMT | isoprenylcysteine carboxyl methyltransferase |
| 202000_at | 262 | BC002772 | 663 | 6.15E−03 | 1.016 | NDUFA6 | NADH dehydrogenase (ubiquinone) 1 alpha subcomplex, 6, 14 kDa |
| 202001_s_at | 263 | BC002772 | 663 | 7.78E−03 | 1.017 | NDUFA6 | NADH dehydrogenase (ubiquinone) 1 alpha subcomplex, 6, 14 kDa |
| 203880_at | 264 | NM_005694 | 664 | 6.24E−03 | 1.017 | COX17 | COX17 homolog, cytochrome c oxidase assembly protein (yeast) |
| 218525_s_at | 265 | NM_017902 | 665 | 9.42E−03 | 1.017 | HIF1AN | hypoxia-inducible factor 1, alpha subunit inhibitor |
| 219798_s_at | 266 | NM_019606 | 666 | 3.38E−03 | 1.017 | FLJ20257 | hypothetical protein FLJ20257 |
| 208398_s_at | 267 | NM_004865 | 667 | 7.76E−03 | 1.017 | TBPL1 | TBP-like 1 |
| 218358_at | 268 | NM_024324 | 668 | 6.57E−03 | 1.017 | — | — |
| 203097_s_at | 269 | NM_014247 | 669 | 4.66E−03 | 1.017 | RAPGEF2 | Rap guanine nucleotide exchange factor (GEF) 2 |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 221598_s_at | 270 | BC002878 | 670 | 7.63E−03 | 1.017 | CRSP8 | cofactor required for Sp1 transcriptional activation, subunit 8, 34 kDa |
| 209546_s_at | 271 | AF323540 | 671 | 6.71E−03 | 1.018 | APOL1 | apolipoprotein L, 1 |
| 50400_at | 272 | AI743990 | 672 | 7.35E−03 | 1.018 | PAOX | polyamine oxidase (exo-N4-amino) |
| 217752_s_at | 273 | NM_018235 | 673 | 4.11E−03 | 1.018 | CNDP2 | CNDP dipeptidase 2 (metallopeptidase M20 family) |
| 201931_at | 274 | NM_000126 | 674 | 6.90E−03 | 1.018 | ETFA | electron-transfer-flavoprotein, alpha polypeptide (glutaric aciduria II) |
| 218567_x_at | 275 | NM_005700 | 675 | 1.00E−02 | 1.019 | DPP3 | dipeptidylpeptidase 3 |
| 202056_at | 276 | AW051311 | 676 | 8.93E−03 | 1.019 | KPNA1 | Karyopherin alpha 1 (importin alpha 5) |
| 218907_s_at | 277 | NM_023942 | 677 | 2.62E−03 | 1.019 | MGC3036 | hypothetical protein MGC3036 |
| 213726_x_at | 278 | AA515698 | 678 | 2.22E−03 | 1.019 | TUBB2 | tubulin, beta, 2 |
| 204448_s_at | 279 | AF031463 | 679 | 7.00E−03 | 1.019 | PDCL | phosducin-like |
| 1405_i_at | 280 | M21121 | 680 | 9.54E−03 | 1.019 | CCL5 | chemokine (C-C motif) ligand 5 |
| 212864_at | 281 | Y16521 | 681 | 9.17E−03 | 1.019 | CDS2 | CDP-diacylglycerol synthase (phosphatidate cytidylyltransferase) 2 |
| 209444_at | 282 | BC001851 | 682 | 1.27E−04 | 1.019 | RAP1GDS1 | RAP1, GTP-GDP dissociation stimulator 1 |
| 208898_at | 283 | AF077614 | 683 | 2.37E−03 | 1.019 | ATP6V1D | ATPase, H+ transporting, lysosomal 34 kDa, V1 subunit D |
| 202377_at | 284 | AW026535 | 684 | 5.30E−03 | 1.019 | OBRGRP /// LEPR | leptin receptor gene-related protein /// leptin receptor |
| 209547_s_at | 285 | BC001043 | 685 | 4.14E−03 | 1.020 | SF4 | splicing factor 4 |
| 202922_at | 286 | BF676980 | 686 | 4.19E−03 | 1.020 | GCLC | glutamate-cysteine ligase, catalytic subunit |
| 201403_s_at | 287 | NM_004528 | 687 | 3.64E−03 | 1.020 | MGST3 | microsomal glutathione S-transferase 3 |
| 213154_s_at | 288 | AI934125 | 688 | 2.75E−03 | 1.020 | BICD2 | bicaudal D homolog 2 (*Drosophila*) |
| 215676_at | 289 | N91109 | 689 | 8.42E−03 | 1.021 | BRF1 | BRF1 homolog, subunit of RNA polymerase III transcription initiation factor IIIB |
| 218927_s_at | 290 | BC002918 | 690 | 8.09E−03 | 1.021 | CHST12 | carbohydrate (chondroitin 4) sulfotransferase 12 |
| 213648_at | 291 | AW614427 | 691 | 6.11E−03 | 1.021 | EXOSC7 | Exosome component 7 |
| 209593_s_at | 292 | AF317129 | 692 | 8.82E−03 | 1.021 | TOR1B | torsin family 1, member B (torsin B) |
| 203731_s_at | 293 | NM_014569 | 693 | 1.78E−03 | 1.022 | ZFP95 | zinc finger protein 95 homolog (mouse) |
| 201234_at | 294 | NM_004517 | 694 | 2.90E−03 | 1.022 | ILK | integrin-linked kinase |
| 214817_at | 295 | BE783668 | 695 | 8.61E−03 | 1.022 | UNC13A | unc-13 homolog A (*C. elegans*) |
| 201761_at | 296 | NM_006636 | 696 | 3.83E−03 | 1.022 | MTHFD2 | methylene tetrahydrofolate dehydrogenase (NAD+ dependent), methenyltetrahydrofol |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 205467_at | 297 | NM_001230 | 697 | 6.50E-03 | 1.022 | CASP10 | caspase 10, apoptosis-related cysteine protease |
| 222318_at | 298 | AI744673 | 698 | 9.20E-03 | 1.022 | FLJ45850 | FLJ45850 protein |
| 209933_s_at | 299 | AF020314 | 699 | 6.24E-03 | 1.022 | CMRF-35H | leukocyte membrane antigen |
| 200734_s_at | 300 | BG341906 | 700 | 4.33E-03 | 1.023 | ARF3 | ADP-ribosylation factor 3 |
| 219899_x_at | 301 | NM_014434 | 701 | 7.97E-03 | 1.023 | NDOR1 | NADPH dependent diflavin oxidoreductase 1 |
| 221563_at | 302 | N36770 | 702 | 3.41E-03 | 1.024 | DUSP10 | dual specificity phosphatase 10 |
| 65517_at | 303 | AA910946 | 703 | 4.00E-03 | 1.024 | AP1M2 | adaptor-related protein complex 1, mu 2 subunit |
| 205126_at | 304 | NM_006296 | 704 | 8.89E-03 | 1.024 | VRK2 | vaccinia related kinase 2 |
| 200696_s_at | 305 | NM_000177 | 705 | 8.30E-03 | 1.024 | GSN | gelsolin (amyloidosis, Finnish type) |
| 208790_s_at | 306 | AF312393 | 706 | 4.43E-03 | 1.025 | PTRF | polymerase I and transcript release factor |
| 205115_s_at | 307 | NM_016196 | 707 | 8.06E-03 | 1.025 | RBM19 | RNA binding motif protein 19 |
| 213982_s_at | 308 | BG107203 | 708 | 8.15E-03 | 1.025 | RABGAP1L | RAB GTPase activating protein 1-like |
| 206992_s_at | 309 | NM_015684 | 709 | 2.03E-03 | 1.025 | ATP5S | ATP synthase, H+ transporting, mitochondrial F0 complex, subunit s (factor B) |
| 201060_x_at | 310 | AI537887 | 710 | 9.12E-04 | 1.025 | STOM | stomatin |
| 209278_s_at | 311 | L27624 | 711 | 7.18E-03 | 1.026 | TFPI2 | tissue factor pathway inhibitor 2 |
| 210542_s_at | 312 | BC000585 | 712 | 4.38E-03 | 1.026 | SLCO3A1 | solute carrier organic anion transporter family, member 3A1 |
| 202006_at | 313 | NM_002835 | 713 | 3.01E-03 | 1.026 | PTPN12 | protein tyrosine phosphatase, non-receptor type 12 |
| 210557_x_at | 314 | M76453 | 714 | 2.04E-03 | 1.026 | CSF1 | colony stimulating factor 1 (macrophage) |
| 210796_x_at | 315 | D86359 | 715 | 2.95E-03 | 1.027 | SIGLEC6 | sialic acid binding Ig-like lectin 6 |
| 220825_s_at | 316 | NM_018240 | 716 | 9.74E-03 | 1.027 | KIRREL | kin of IRRE like (Drosophila) |
| 202378_s_at | 317 | NM_017526 | 717 | 2.72E-03 | 1.027 | OBRGRP | leptin receptor gene-related protein |
| 210241_s_at | 318 | AB007458 | 718 | 3.02E-03 | 1.027 | TP53AP1 | TP53 activated protein 1 |
| 213069_at | 319 | AI148659 | 719 | 2.90E-03 | 1.027 | — | — |
| 216034_at | 320 | AA558468 | 720 | 9.90E-03 | 1.027 | SUHW1 | suppressor of hairy wing homolog 1 (Drosophila) |
| 210793_s_at | 321 | U41815 | 721 | 2.64E-03 | 1.029 | NUP98 | nucleoporin 98 kDa |
| 207375_s_at | 322 | NM_002189 | 722 | 3.71E-03 | 1.029 | IL15RA | interleukin 15 receptor, alpha |
| 206247_at | 323 | NM_005931 | 723 | 2.70E-03 | 1.029 | MICB | MHC class I polypeptide-related sequence B |
| 217078_s_at | 324 | AJ010102 | 724 | 9.65E-03 | 1.029 | CMRF-35H | leukocyte membrane antigen |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 219257_s_at | 325 | NM_021972 | 725 | 1.62E−03 | 1.030 | SPHK1 | sphingosine kinase 1 |
| 204781_s_at | 326 | NM_000043 | 726 | 8.44E−03 | 1.030 | TNFRSF6 | tumor necrosis factor receptor superfamily, member 6 |
| 221536_s_at | 327 | AL136897 | 727 | 2.28E−03 | 1.030 | FLJ11301 | hypothetical protein FLJ11301 |
| 209468_at | 328 | AB017498 | 728 | 8.91E−03 | 1.030 | LRP5 | low density lipoprotein receptor-related protein 5 |
| 201061_s_at | 329 | M81635 | 729 | 1.46E−04 | 1.030 | STOM | stomatin |
| 203499_at | 330 | NM_004431 | 730 | 6.49E−03 | 1.031 | EPHA2 | EPH receptor A2 |
| 213324_at | 331 | AK024281 | 731 | 7.63E−03 | 1.031 | SRC | v-src sarcoma (Schmidt-Ruppin A-2) viral oncogene homolog (avian) |
| 221535_at | 332 | AL136897 | 727 | 3.81E−03 | 1.031 | FLJ11301 | hypothetical protein FLJ11301 |
| 219938_at | 333 | NM_024430 | 732 | 3.19E−03 | 1.032 | PSTPIP2 | proline-serine-threonine phosphatase interacting protein 2 |
| 213787_s_at | 334 | AV702405 | 733 | 1.78E−03 | 1.032 | EBP | emopamil binding protein (sterol isomerase) |
| 219592_at | 335 | NM_024596 | 734 | 8.43E−03 | 1.032 | MCPH1 | microcephaly, primary autosomal recessive 1 |
| 200637_s_at | 336 | AI762627 | 735 | 5.52E−03 | 1.033 | PTPRF | protein tyrosine phosphatase, receptor type, F |
| 202193_at | 337 | NM_005569 | 736 | 4.88E−03 | 1.033 | LIMK2 | LIM domain kinase 2 |
| 214859_at | 338 | AI635302 | 737 | 8.68E−03 | 1.034 | FSTL4 | follistatin-like 4 |
| 209213_at | 339 | BC002511 | 738 | 5.69E−03 | 1.034 | CBR1 | carbonyl reductase 1 |
| 218945_at | 340 | NM_024109 | 739 | 3.75E−03 | 1.034 | MGC2654 | hypothetical protein MGC2654 |
| 220471_s_at | 341 | NM_025107 | 740 | 8.29E−03 | 1.035 | MYCT1 | myc target 1 |
| 59625_at | 342 | AI912351 | 741 | 5.19E−03 | 1.035 | NOL3 | nucleolar protein 3 (apoptosis repressor with CARD domain) |
| 207233_s_at | 343 | NM_000248 | 742 | 2.93E−03 | 1.035 | MITF | microphthalmia-associated transcription factor |
| 214070_s_at | 344 | AW006935 | 743 | 5.14E−03 | 1.036 | ATP10B | ATPase, Class V, type 10B |
| 219785_s_at | 345 | NM_024735 | 744 | 5.84E−03 | 1.036 | FBXO31 | F-box protein 31 |
| 220684_at | 346 | NM_013351 | 745 | 3.34E−03 | 1.037 | TBX21 | T-box 21 |
| 202245_at | 347 | AW084510 | 746 | 7.02E−03 | 1.037 | LSS | lanosterol synthase (2,3-oxidosqualene-lanosterol cyclase) |
| 207298_at | 348 | NM_006632 | 747 | 6.68E−03 | 1.037 | SLC17A3 | solute carrier family 17 (sodium phosphate), member 3 |
| 220201_at | 349 | NM_018835 | 748 | 3.85E−03 | 1.038 | MNAB | membrane associated DNA binding protein |
| 203208_s_at | 350 | BF214329 | 749 | 6.89E−04 | 1.038 | CHPPR | likely ortholog of chicken chondrocyte protein with a poly-proline region |
| 207033_at | 351 | NM_005142 | 750 | 3.42E−04 | 1.039 | GIF | gastric intrinsic factor (vitamin B synthesis) |
| 204929_s_at | 352 | NM_006634 | 751 | 6.38E−03 | 1.039 | VAMP5 | vesicle-associated membrane protein 5 (myobrevin) |
| 209735_at | 353 | AF098951 | 752 | 7.05E−03 | 1.039 | ABCG2 | ATP-binding cassette, sub-family G (WHITE), member 2 |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 209234_at | 354 | BF939474 | 753 | 3.31E−04 | 1.039 | KIF1B | kinesin family member 1B |
| 210102_at | 355 | BC001234 | 754 | 5.97E−03 | 1.040 | LOH11CR2A | loss of heterozygosity, 11, chromosomal region 2, gene A |
| 204114_at | 356 | NM_007361 | 755 | 4.45E−03 | 1.041 | NID2 | nidogen 2 (osteonidogen) |
| 203344_s_at | 357 | NM_002894 | 756 | 1.33E−03 | 1.041 | RBBP8 | retinoblastoma binding protein 8 |
| 216891_at | 358 | U00956 | 757 | 5.03E−03 | 1.042 | — | — |
| 221680_s_at | 359 | AF147782 | 758 | 9.08E−03 | 1.042 | ETV7 | ets variant gene 7 (TEL2 oncogene) |
| 202087_s_at | 360 | NM_001912 | 759 | 3.63E−03 | 1.042 | CTSL | cathepsin L |
| 218243_at | 361 | NM_025158 | 760 | 6.62E−03 | 1.043 | RUFY1 | RUN and FYVE domain containing 1 |
| 201980_s_at | 362 | NM_012425 | 761 | 5.59E−03 | 1.044 | RSU1 | Ras suppressor protein 1 |
| 221280_s_at | 363 | NM_019619 | 762 | 4.65E−04 | 1.044 | PARD3 | par-3 partitioning defective 3 homolog (*C. elegans*) |
| 205108_s_at | 364 | NM_000384 | 763 | 2.36E−04 | 1.045 | APOB | apolipoprotein B (including Ag(x) antigen) |
| 204241_at | 365 | BF055171 | 764 | 6.95E−04 | 1.045 | ACOX3 | acyl-Coenzyme A oxidase 3, pristanoyl |
| 201278_at | 366 | N21202 | 765 | 2.71E−03 | 1.049 | DAB2 | Disabled homolog 2, mitogen-responsive phosphoprotein (*Drosophila*) |
| 202067_s_at | 367 | AI861942 | 766 | 1.95E−03 | 1.050 | LDLR | low density lipoprotein receptor (familial hypercholesterolemia) |
| 202085_at | 368 | NM_004817 | 767 | 3.10E−03 | 1.051 | TJP2 | tight junction protein 2 (zona occludens 2) |
| 214157_at | 369 | AA401492 | 768 | 4.90E−03 | 1.053 | GNAS | GNAS complex locus |
| 221526_x_at | 370 | AF196185 | 769 | 2.72E−03 | 1.053 | PARD3 | par-3 partitioning defective 3 homolog (*C. elegans*) |
| 207738_s_at | 371 | NM_013436 | 770 | 2.00E−03 | 1.054 | NCKAP1 | NCK-associated protein 1 |
| 204769_s_at | 372 | NM_000544 | 771 | 3.15E−03 | 1.054 | TAP2 | transporter 2, ATP-binding cassette, sub-family B (MDR/TAP) |
| 216693_x_at | 373 | AL133102 | 772 | 6.34E−03 | 1.055 | HDGFRP3 | hepatoma-derived growth factor, related protein 3 |
| 202068_s_at | 374 | NM_000527 | 773 | 5.72E−03 | 1.057 | LDLR | low density lipoprotein receptor (familial hypercholesterolemia) |
| 202743_at | 375 | BE622627 | 774 | 7.96E−04 | 1.061 | PIK3R3 | phosphoinositide-3-kinase, regulatory subunit 3 (p55, gamma) |
| 206638_at | 376 | NM_000867 | 775 | 7.47E−03 | 1.061 | HTR2B | 5-hydroxytryptamine (serotonin) receptor 2B |
| 31874_at | 377 | Y07846 | 776 | 2.32E−03 | 1.061 | GAS2L1 | growth arrest-specific 2 like 1 |
| 201798_s_at | 378 | NM_013451 | 777 | 5.01E−03 | 1.062 | FER1L3 | fer-1-like 3, myoferlin (*C. elegans*) |
| 219288_at | 379 | NM_020685 | 778 | 6.67E−04 | 1.063 | C3orf14 | chromosome 3 open reading frame 14 |
| 220167_s_at | 380 | NM_015369 | 779 | 5.44E−04 | 1.064 | TP53TG3 | TP53TG3 protein |

TABLE 1-continued

Genes which are differentially expressed in blood samples of benign multiple sclerosis (BMS) and typical relapsing-remitting multiple sclerosis (RRMS) subjects

| Affymetrix Probeset ID | SEQ ID NO: | Representative Public ID | SEQ ID NO: | p-value BMS vs. typical RRMS | Log Fold Change (BMS vs. typical RRMS) | Gene Symbol | Gene Title |
|---|---|---|---|---|---|---|---|
| 211354_s_at | 381 | U52913 | 780 | 1.67E-03 | 1.066 | LEPR | leptin receptor |
| 213317_at | 382 | AL049313 | 781 | 7.15E-03 | 1.067 | CLIC5 | Chloride intracellular channel 5 |
| 212390_at | 383 | AB007923 | 782 | 8.15E-03 | 1.070 | PDE4DIP | phosphodiesterase 4D interacting protein (myomegalin) |
| 212062_at | 384 | AB014511 | 783 | 8.65E-03 | 1.070 | ATP9A | ATPase, Class II, type 9A |
| 203337_x_at | 385 | NM_004763 | 784 | 6.03E-03 | 1.071 | ITGB1BP1 | integrin beta 1 binding protein 1 |
| 210029_at | 386 | M34455 | 785 | 5.97E-03 | 1.073 | INDO | indoleamine-pyrrole 2,3 dioxygenase |
| 206049_at | 387 | NM_003005 | 786 | 8.60E-03 | 1.074 | SELP | selectin P (granule membrane protein 140 kDa, antigen CD62) |
| 202949_s_at | 388 | NM_001450 | 787 | 6.99E-03 | 1.076 | FHL2 | four and a half LIM domains 2 |
| 211864_s_at | 389 | AF207990 | 788 | 7.27E-03 | 1.076 | FER1L3 | fer-1-like 3, myoferlin (C. elegans) |
| 206254_at | 390 | NM_001963 | 789 | 5.83E-03 | 1.077 | EGF | epidermal growth factor (beta-urogastrone) |
| 210073_at | 391 | L32867 | 790 | 5.66E-04 | 1.077 | SIAT8A | sialyltransferase 8A (alpha-N-acetylneuraminate: alpha-2,8-sialyltransferase, GD |
| 209524_at | 392 | AK001280 | 791 | 1.03E-03 | 1.080 | HDGFRP3 | hepatoma-derived growth factor, related protein 3 |
| 219759_at | 393 | NM_022350 | 792 | 8.03E-04 | 1.081 | LRAP | leukocyte-derived arginine aminopeptidase |
| 202112_at | 394 | NM_000552 | 793 | 1.22E-03 | 1.082 | VWF | von Willebrand factor |
| 219410_at | 395 | NM_018004 | 794 | 4.81E-03 | 1.083 | FLJ10134 | hypothetical protein FLJ10134 |
| 203819_s_at | 396 | AU160004 | 795 | 3.58E-03 | 1.088 | IMP-3 | IGF-II mRNA-binding protein 3 |
| 212730_at | 397 | AK026420 | 796 | 3.19E-03 | 1.090 | DMN | desmuslin |
| 220122_at | 398 | NM_024717 | 797 | 5.82E-03 | 1.090 | MCTP1 | multiple C2-domains with two transmembrane regions 1 |
| 208782_at | 399 | BC000055 | 798 | 2.14E-03 | 1.095 | FSTL1 | follistatin-like 1 |
| 202468_s_at | 400 | NM_003798 | 799 | 1.36E-03 | 1.096 | CTNNAL1 | catenin (cadherin-associated protein), alpha-like 1 |
| 207018_s_at | 401 | NM_004163 | 800 | 4.02E-03 | 1.101 | RAB27B | RAB27B, member RAS oncogene family |
| 210354_at | 402 | M29383 | 801 | 4.60E-03 | 1.102 | — | — |
| 201110_s_at | 403 | NM_003246 | 802 | 9.38E-03 | 1.111 | THBS1 | thrombospondin 1 |
| 207808_s_at | 404 | NM_000313 | 803 | 2.92E-03 | 1.114 | PROS1 | protein S (alpha) |
| 205612_at | 405 | NM_007351 | 804 | 7.97E-03 | 1.118 | MMRN1 | multimerin 1 |
| 214073_at | 406 | BG475299 | 805 | 2.37E-03 | 1.121 | CTTN | cortactin |

Presented are the 406 differentiating genes given by the gene name and description, the Affymetrix probeset identification number, and a representative GenBank Accession number between BMS and typical RRMS patients. p-value - statistical significance by ANOVA; Log Fold Change = refers to the logarithms fold change between the expression level of a polynucleotide in a blood sample of a BMS subject as compared to the expression level in a blood sample of a typical RRMS subject: The (−) sign means that the polynucleotide is downregulated (decreased in level) in BMS as compared to typical RRMS subjects; and the (+) sign means that the polynucleotide is upregulated (increased in level) in BMS as compared to typical RRMS subjects.

Table 2 hereinbelow discloses additional polynucleotides (RNA alternative transcripts) of the above identified 406 genes which expression level is differentiating between typical RRMS and BMS.

TABLE 2

| PROBESET | SEQ ID NO: | Refseq Ids/SEQ ID NO: | | | | REFSEQ_UNIGENE | REFSEQ_BAND |
|---|---|---|---|---|---|---|---|
| 216683_at | 1 | —/— | | | | — | — |
| 219629_at | 2 | NM_017911/997 | | | | C22ORF8 | Hs.265018 |
| 210379_s_at | 3 | NM_012290/948 | | | | TLK1 | Hs.470586 |
| 213472_at | 4 | NM_020405/1022 | | | | PLXDC1 | Hs.125036 |
| 219700_at | 5 | NM_012290/948 | | | | TLK1 | Hs.470586 |
| 211077_s_at | 6 | NM_012290/948 | | | | TLK1 | Hs.470586 |
| 210969_at | 7 | —/— | | | | — | — |
| 216298_at | 8 | —/— | | | | — | — |
| 219834_at | 9 | NM_024744/1051 | | | | ALS2CR8 | Hs.444982 |
| 215262_at | 10 | —/— | | | | — | — |
| 220715_at | 11 | —/— | | | | — | — |
| 207164_s_at | 12 | NM_205768/1103 | NM_006352/1133 | | | ZNF238, ZNF238, PDPR | Hs.69997, Hs.69997, Hs.461183 |
| 220236_at | 13 | NM_017990/999 | | | | NT5E | Hs.153952 |
| 203939_at | 14 | NM_002526/865 | | | | PASK | Hs.397891 |
| 216945_x_at | 15 | NM_015148/970 | | | | HPGD | Hs.77348 |
| 203913_s_at | 16 | NM_000860/834 | | | | HPGD | Hs.77348 |
| 204864_s_at | 17 | NM_175767/1088 | NM_002183/1189 | | | IL6ST, IL6ST, | Hs.532082, Hs.532082, |
| 215698_at | 18 | —/— | | | | — | — |
| 213534_s_at | 19 | NM_015148/970 | | | | PASK | Hs.397891 |
| 210948_s_at | 20 | NM_016269/988 | | | | LEF1 | Hs.125132 |
| 220458_at | 21 | NM_018038/1001 | | | | FLJ10246 | Hs.274274 |
| 212093_s_at | 22 | NM_020749/1025 | NM_001001925/1114 | NM_001001924/1182 | NM_001001927/1216 | NM_001001931/1234 | MTUS1, MTUS1, MTUS1, MTUS1, MTUS1, FLJ14011 | Hs.7946, Hs.7946, Hs.7946, Hs.7946, Hs.7946, Hs.433473 |
| 207120_at | 23 | NM_022103/1033 | | | | VSIG4 | Hs.8904 |
| 204787_at | 24 | NM_007268/939 | | | | — | — |
| 215512_at | 25 | —/— | | | | — | — |
| 46947_at | 26 | —/— | | | | — | — |
| 210012_s_at | 27 | —/— | | | | — | — |

TABLE 2-continued

| PROBESET | SEQ ID NO: | Refseq Ids/SEQ ID NO: | | REFSEQ_UNIGENE | REFSEQ_BAND |
|---|---|---|---|---|---|
| 210192_at | 28 | NM_006095/ 918 | | ATP8A1 | Hs.435052 |
| 207603_at | 29 | —/— | | — | — |
| 218584_at | 30 | NM_024549/ 1047 | | FLJ21127 | Hs.211511 |
| 213470_s_at | 31 | NM_005520/ 912 | | HNRPH1 | Hs.202166 |
| 210461_s_at | 32 | NM_006720/ 930 | NM_001003407/ 1187 NM_001003408/ 1232 | ABLIM1, ABLIM1, ABLIM1, ABLIM1, | Hs.438236, Hs.438236, Hs.438236, Hs.438236, |
| 217656_at | 33 | —/— | | — | — |
| 215177_s_at | 34 | NM_000210/ 826 | | ITGA6 | Hs.133397 |
| 204498_s_at | 35 | NM_001116/ 848 | | ADCY9 | Hs.391860 |
| 216419_at | 36 | —/— | | — | — |
| 204019_s_at | 37 | NM_015677/ 979 | | SH3YL1 | Hs.515951 |
| 214850_at | 38 | NM_207331/ 1106 | | LOC153561 | Hs.545578 |
| 200672_x_at | 39 | NM_003128/ 872 | | SPTBN1 | Hs.503178 |
| 220179_at | 40 | NM_022357/ 1037 | | DPEP3 | Hs.302028 |
| 208591_s_at | 41 | NM_000922/ 835 | | PDE3B | Hs.445711 |
| 219199_at | 42 | NM_014423/ 958 | | AF5Q31 | Hs.519313 |
| 216959_x_at | 43 | NM_005010/ 899 | | NRCAM | Hs.21422 |
| 215041_s_at | 44 | NM_015296/ 973 | | DOCK9 | Hs.314413 |
| 213447_at | 45 | —/— | | — | — |
| 218532_s_at | 46 | NM_019000/ 1016 | | FLJ20152 | Hs.481704 |
| 220485_s_at | 47 | NM_018556/ 1011 | NM_080816/ 1150 | SIRPB2, SIRPB2, GALNT4 | Hs.50716, Hs.50716, Hs.534374 |
| 220442_at | 48 | NM_003774/ 881 | | | |
| 211856_x_at | 49 | NM_006139/ 919 | | CD28 | Hs.1987 |
| 206828_at | 50 | NM_003328/ 875 | | TXK | Hs.479669 |
| 214447_at | 51 | NM_005238/ 907 | | ETS1 | Hs.369438 |
| 215244_at | 52 | —/— | | — | — |
| 206579_at | 53 | NM_006298/ 922 | | ZNF192 | Hs.57679 |

TABLE 2-continued

| PROBESET | SEQ ID NO: | Refseq Ids/SEQ ID NO: | | | | REFSEQ_UNIGENE | REFSEQ_BAND |
|---|---|---|---|---|---|---|---|
| 205254_x_at | 54 | NM_201632/ 1099 | NM_201634/ 1173 | NM_213648/ 1215 | NM_003202/ 1219 | TCF7, TCF7, TCF7, TCF7, | Hs.519580, Hs.519580, Hs.519580, Hs.519580, |
| 210349_at | 55 | NM_001744/ 856 | | | | CAMK4 | Hs.220629 |
| 208157_at | 56 | NM_009586/ 942 | | | | SIM2 | Hs.146186 |
| 214972_at | 57 | — | | | | | |
| 207334_s_at | 58 | NM_003242/ 873 | | | | TGFBR2 | Hs.82028 |
| 217666_at | 59 | — | | | | | |
| 215771_x_at | 60 | NM_020975/ 1026 | | | | RET, RET, | Hs.350321, Hs.350321, |
| 216139_s_at | 61 | NM_033392/ 1057 | NM_020630/ 1143 | | | MAPK8IP3, MAPK8IP3, | Hs.207763, Hs.207763, |
| 216902_s_at | 62 | NM_018427/ 1010 | NM_015133/ 1138 | | | RRN3 | Hs.460078 |
| 208265_at | 63 | NM_020161/ 1019 | | | | DKFZP547H025 | Hs.283092 |
| 209456_s_at | 64 | NM_033645/ 1059 | NM_033644/ 1148 | | | FBXW11, FBXW11, FBXW11, | Hs.484138, Hs.484138, Hs.484138, |
| 217237_at | 65 | — | | | | | |
| 217208_s_at | 66 | NM_004087/ 885 | | | | DLG1 | Hs.292549 |
| 221757_at | 67 | NM_052880/ 1060 | | | | MGC17330 | Hs.26670 |
| 213481_at | 68 | — | | | | | |
| 219025_at | 69 | NM_020404/ 1021 | | | | CD164L1 | Hs.195727 |
| 215201_at | 70 | — | | | | | |
| 205378_at | 71 | NM_000665/ 833 | NM_015831/ 1139 | | | ACHE, ACHE, ITGB1BP2 | Hs.154495, Hs.154495, Hs.109999 |
| 219829_at | 72 | NM_012278/ 947 | | | | | |
| 216908_x_at | 73 | NM_018427/ 1010 | NM_145237/ 1156 | | | RRN3, LOC94431, | Hs.460078, Hs.546468, |
| 217184_s_at | 74 | NM_206961/ 1105 | NM_002344/ 1121 | | | LTK, LTK, | Hs.434481, Hs.434481, |
| 211181_x_at | 75 | NM_001001890/ 843 | NM_001754/ 1179 | | | RUNX1, RUNX1, EVER1 | Hs.149261, Hs.149261, Hs.16165 |
| 214958_s_at | 76 | NM_007267/ 938 | | | | KIAA2010 | Hs.533887 |
| 220369_at | 77 | NM_017936/ 998 | | | | | |
| 211848_s_at | 78 | NM_006890/ 932 | | | | CEACAM7 | Hs.74466 |

TABLE 2-continued

| PROBESET | SEQ ID NO: | Refseq Ids/SEQ ID NO: | | | REFSEQ_UNIGENE | REFSEQ_BAND |
|---|---|---|---|---|---|---|
| 221638_s_at | 79 | NM_003763/ 880 | NM_001001434/ 842 | NM_001001433/ 1181 | STX16, STX16, STX16, | Hs.307913, Hs.307913, Hs.307913, |
| 221723_s_at | 80 | NM_021196/ 1028 | NM_133479/ 1152 | NM_133478/ 1201 | SLC4A5, SLC4A5, SLC4A5, | Hs.469033, Hs.469033, Hs.469033, |
| 201380_at | 81 | NM_006371/ 923 | | | CRTAP | Hs.517888 |
| 34063_at | 82 | NM_001003715/ 845 | NM_001003716/ 1178 | NM_004259/ 1191 | RECQL5, RECQL5, RECQL5, | Hs.514480, Hs.514480, Hs.514480, |
| 214757_at | 83 | —/— | | | — | — |
| 218176_at | 84 | NM_022149/ 1034 | | | MAGEF1 | Hs.306123 |
| 221977_at | 85 | —/— | | | — | — |
| 214161_at | 86 | —/— | | | — | — |
| 214857_at | 87 | —/— | | | — | — |
| 216230_x_at | 88 | NM_000543/ 829 | NM_001007593/ 1118 | | SMPD1, SMPD1, | Hs.498173, Hs.498173, |
| 205019_s_at | 89 | NM_004624/ 893 | | | VIPR1 | Hs.348500 |
| 221707_s_at | 90 | NM_018289/ 1006 | | | FLJ10979 | Hs.461819 |
| 208664_s_at | 91 | NM_001001894/ 844 | NM_003316/ 1180 | | TTC3, TTC3, | Hs.368214, Hs.368214, |
| 215167_at | 92 | —/— | | | — | — |
| 215437_x_at | 93 | NM_013449/ 955 | | | BAZ2A | Hs.314263 |
| 210892_s_at | 94 | NM_001518/ 854 | NM_033001/ 1146 | NM_033000/ 1198 | NM_032999/ 1222 | GTF2I, GTF2I, GTF2I, GTF2I, | Hs.520459, Hs.520459, Hs.520459, Hs.520459, |
| 212400_at | 95 | NM_203305/ 1101 | | | EEIG1 | Hs.460208 |
| 215137_at | 96 | —/— | | | — | — |
| 205750_at | 97 | NM_004332/ 888 | | | BPHL | Hs.10136 |
| 210628_x_at | 98 | NM_003573/ 877 | | | LTBP4 | Hs.466766 |
| 218210_at | 99 | NM_024619/ 1050 | | | FN3KRP | Hs.31431 |
| 216784_at | 100 | —/— | | | — | — |
| 201819_at | 101 | NM_005505/ 911 | | | SCARB1 | Hs.298813 |
| 214312_at | 102 | —/— | | | — | — |
| 215556_at | 103 | —/— | | | — | — |
| 221756_at | 104 | NM_052880/ 1060 | | | MGC17330 | Hs.26670 |
| 216909_at | 105 | —/— | | | — | — |

TABLE 2-continued

| PROBESET | SEQ ID NO: | Refseq Ids/SEQ ID NO: | | | REFSEQ_UNIGENE | REFSEQ_BAND |
|---|---|---|---|---|---|---|
| 220249_at | 106 | NM_012269/946 | | | HYAL4 | Hs.28673 |
| 211272_s_at | 107 | NM_201554/1098 | NM_201445/1119 | NM_201444/1229 | DGKA, DGKA, DGKA, DGKA, FLJ11196 | Hs.524488, Hs.524488, Hs.524488, Hs.524488, Hs.416755 |
| 218651_s_at | 108 | NM_018357/1008 | | | DHRS6 | Hs.124696 |
| 218285_s_at | 109 | NM_020139/1018 | | | — | — |
| 217385_at 202894_at | 110 111 | —/ NM_004444/890 | | | EPHB4 | Hs.437008 |
| 217631_at 220487_at | 112 113 | —/ NM_018968/1015 | | | SNTG2 | Hs.148819 |
| 203579_s_at | 114 | NM_003983/884 | | | SLC7A6 | Hs.351571 |
| 215412_x_at | 115 | NM_005395/908 | NM_001003686/1115 | NM_001003687/1183 | PMS2L3, PMS2L3, PMS2L3, PMS2L5, POM121, PMS2, | Hs.549057, Hs.549057, Hs.549057, Hs.397073, Hs.488624, Hs.487470, |
| 212217_at 221602_s_at | 116 117 | —/ NM_005449/909 | | | TOSO | Hs.58831 |
| 217847_s_at | 118 | NM_005119/905 | | | THRAP3 | Hs.160211 |
| 215275_at 221951_at | 119 120 | —/ NM_174940/1087 | NM_174930/1086 | NM_002679/867 | LOC283232 | Hs.448664 |
| 213224_s_at 218967_s_at | 121 122 | —/ NM_030664/1055 | NM_001001484/1113 | | PTER, PTER, ATM, ATM, | Hs.444321, Hs.444321, Hs.435561, Hs.435561, |
| 208442_s_at | 123 | NM_138292/1069 | NM_000051/1109 | | NUCB2 | Hs.128686 |
| 203675_at | 124 | NM_005013/900 | | | PIK3R2 | Hs.371344 |
| 207105_s_at | 125 | NM_005027/901 | | | MGC1136 | Hs.8719 |
| 219144_at | 126 | NM_024025/1042 | | | CD59, CD59, CD59, CD59, | Hs.278573, Hs.278573, Hs.278573, Hs.278573, |
| 212463_at | 127 | NM_000611/831 | NM_203331/1175 | NM_203330/1212 | NM_203329/1230 | |
| 202040_s_at | 128 | NM_005056/902 | | | JARID1A | Hs.76272 |

TABLE 2-continued

| PROBESET | SEQ ID NO: | Refseq Ids/SEQ ID NO: | | | REFSEQ_UNIGENE | REFSEQ_BAND |
|---|---|---|---|---|---|---|
| 64432_at | 129 | NM_016534/ 991 | | | FLJ39616 | Hs.333120 |
| 200965_s_at | 130 | NM_006720/ 930 | NM_002313/ 1120 | NM_001003407/ 1187 | NM_001003408/ 1232 | ABLIM1, ABLIM1, ABLIM1, ABLIM1, PBP | Hs.438236, Hs.438236, Hs.438236, Hs.438236, Hs.433863 |
| 205353_s_at | 131 | NM_002567/ 866 | | | | PBP | |
| 213177_at | 132 | NM_033392/ 1057 | NM_015133/ 1138 | | MAPK8IP3, MAPK8IP3, FTS | Hs.207763, Hs.207763, Hs.380897 |
| 218373_at | 133 | NM_022476/ 1040 | | | | |
| 208333_at | 134 | NM_022363/ 1039 | | | LHX5 | Hs.302029 |
| 206150_at | 135 | NM_001242/ 851 | | | TNFRSF7 | Hs.355307 |
| 202431_s_at | 136 | NM_002467/ 863 | | | MYC | Hs.202453 |
| 207838_x_at | 137 | NM_020524/ 1023 | | | PBXIP1 | Hs.505806 |
| 218325_s_at | 138 | NM_080797/ 1062 | NM_080796/ 1149 | | DATF1, DATF1, DATF1 | Hs.551527, Hs.551527, Hs.551527 |
| 218475_at | 139 | NM_182984/ 1090 | NM_022727/ 1144 | | HTF9C, HTF9C, PUS1 | Hs.549133, Hs.549133, Hs.507295 |
| 218670_at | 140 | NM_025215/ 1053 | | | | |
| 205594_at | 141 | NM_014897/ 967 | | | ZNF652 | Hs.463375 |
| 215411_s_at | 142 | NM_147200/ 1076 | NM_147686/ 1160 | | C6ORF4, C6ORF4, KIAA0372 | Hs.486228, Hs.486228, Hs.482868 |
| 203048_s_at | 143 | NM_014639/ 962 | | | | |
| 216885_s_at | 144 | NM_015726/ 982 | | | WDR42A | Hs.492236 |
| 219767_s_at | 145 | NM_005111/ 903 | NM_145311/ 1157 | NM_145858/ 1202 | CRYZL1, CRYZL1, CRYZL1 | Hs.352671, Hs.352671, Hs.352671 |
| 219131_at | 146 | NM_013319/ 953 | | | TERE1 | Hs.522933 |
| 213176_at | 147 | NM_003573/ 877 | | | LTBP4 | Hs.466766 |
| 208661_s_at | 148 | NM_001001894/ 844 | NM_003316/ 1180 | | TTC3, TTC3 | Hs.368214, Hs.368214 |
| 208196_x_at | 149 | NM_172388/ 1083 | NM_172389/ 1164 | NM_172387/ 1206 | NM_006162/ 1220 | NFATC1, NFATC1, NFATC1, NFATC1 | Hs.534074, Hs.534074, Hs.534074, Hs.534074 |
| 212178_s_at | 150 | NM_172020/ 1081 | | | POM121 | Hs.488624 |

TABLE 2-continued

| PROBESET | SEQ ID NO: | Refseq Ids/SEQ ID NO: | | | REFSEQ_UNIGENE | REFSEQ_BAND |
|---|---|---|---|---|---|---|
| 221601_s_at | 151 | NM_005449/ 909 | | | TOSO | Hs.58831 |
| 222013_x_at | 152 | NM_152563/ 1077 | NM_032916/ 1145 | | FLJ10661, MGC16279, FLJ10661, SPOCK2 | Hs.61142, Hs.458413, Hs.61142, Hs.523009 |
| 202524_s_at | 153 | NM_014767/ 963 | NM_018172/ 1196 | | — | — |
| 212068_s_at | 154 | — | | | — | — |
| 202830_s_at | 155 | NM_001467/ 853 | | | SLC37A4 | Hs.132760 |
| 209835_x_at | 156 | NM_001001391/ 841 | NM_001001390/ 1177 | NM_001001389/ 1186 | CD44, CD44, CD44, CD44, CD44 | Hs.502328, Hs.502328, Hs.502328, Hs.502328, Hs.502328 |
| 212257_s_at | 157 | NM_139045/ 1071 | NM_003070/ 1124 | NM_000610/ 1231 | SMARCA2, SMARCA2 | Hs.298990, Hs.298990 |
| 212071_s_at | 158 | — | | | — | — |
| 213322_at | 159 | | | | C6ORF130 | Hs.549281 |
| 210645_s_at | 160 | NM_001001894/ 844 | NM_003316/ 1180 | | TTC3, TTC3 | Hs.368214, Hs.368214 |
| 202514_at | 161 | — | | | — | — |
| 217122_s_at | 162 | NM_014854/ 964 | | | SLC35E2 | Hs.551612 |
| 218440_at | 163 | NM_020166/ 1020 | | | MCCC1 | Hs.47649 |
| 210707_x_at | 164 | NM_174930/ 1086 | NM_002679/ 867 | NM_001003686/ 1115 | NM_001003687/ 1183 | NM_000535/ 828 | PMS2L5, POM121, PMS2L3, PMS2L3, PMS2L3, PMS2, RCN3 | Hs.397073, Hs.488624, Hs.549057, Hs.549057, Hs.549057, Hs.487470, Hs.439184 |
| 61734_at | 165 | NM_020650/ 1024 | | | | | |
| 221500_s_at | 166 | NM_001001434/ 842 | NM_003763/ 880 | NM_001001433/ 1181 | STX16, STX16, STX16 | Hs.307913, Hs.307913, Hs.307913 |
| 219422_at | 167 | — | | | — | — |
| 222244_s_at | 168 | NM_017903/ 996 | | | FLJ20618 | Hs.551545 |
| 212550_at | 169 | NM_012448/ 950 | | | STAT5B | Hs.132864 |
| 206544_x_at | 170 | NM_139045/ 1071 | NM_003070/ 1124 | | SMARCA2, SMARCA2 | Hs.298990, Hs.298990 |
| 216380_x_at | 171 | NM_001031/ 847 | | | RPS28 | Hs.546293 |
| 203408_s_at | 172 | NM_002971/ 870 | | | SATB1 | Hs.517717 |

TABLE 2-continued

| PROBESET | SEQ ID NO: | Refseq Ids/SEQ ID NO: | | | REFSEQ_UNIGENE | REFSEQ_BAND |
|---|---|---|---|---|---|---|
| 218258_at | 173 | NM_015972/ 984 | | | MGC9850 | Hs.507584 |
| 212234_at | 174 | NM_015338/ 976 | | | ASXL1 | Hs.374043 |
| 217461_x_at | 175 | NM_001207/ 849 | | | BTF3 | Hs.529798 |
| 218428_s_at | 176 | NM_016316/ 989 | | | REV1L | Hs.443077 |
| 215667_x_at | 177 | NM_002679/ 867 | NM_174930/ 1086 | NM_005395/ 908 | NM_001003686/ 1115 | NM_001003687/ 1183 | POM121, PMS2L5, PMS2L3, PMS2L3, PMS2L3, | Hs.488624, Hs.397073, Hs.549057, Hs.549057, Hs.549057, |
| 220465_at | 178 | —/ | | | | |
| 217988_at | 179 | NM_021178/ 1027 | | | CCNB1IP1, CCNB1IP1, CCNB1IP1, CCNB1IP1, FLJ12270 | Hs.107003, Hs.107003, Hs.107003, Hs.107003, Hs.280951 |
| 221981_s_at | 180 | NM_030581/ 1054 | | | | |
| 212201_at | 181 | —/ | | | | |
| 208795_s_at | 182 | NM_005916/ 916 | NM_182776/ 1168 | NM_182852/ 1169 | | MCM7, MCM7, GPSN2, GPSN2, | Hs.438720, Hs.438720, Hs.515642, Hs.515642, |
| 208336_s_at | 183 | NM_004868/ 898 | NM_138501/ 1153 | | | STX16, STX16, STX16, MMS19L | Hs.307913, Hs.307913, Hs.307913, Hs.500721 |
| 221499_s_at | 184 | NM_001001434/ 842 | NM_003763/ 880 | NM_001001433/ 1181 | | | |
| 202167_s_at | 185 | NM_022362/ 1038 | | | | |
| 201065_s_at | 186 | NR_002206/ 1107 | NM_001518/ 854 | NM_033001/ 1146 | NM_033000/ 1198 | NM_032999/ 1222 | GTF2I, GTF2I, GTF2I, GTF2I, | Hs.520459, Hs.520459, Hs.520459, Hs.520459, |
| 211172_x_at | 187 | NM_004842/ 896 | NM_138633/ 1154 | NM_016377/ 1194 | | | AKAP7, AKAP7, AKAP7, ZNF444 | Hs.486483, Hs.486483, Hs.486483, Hs.24545 |
| 218707_at | 188 | NM_018337/ 1007 | | | | |
| 206770_s_at | 189 | NM_012243/ 945 | | | SLC35A3 | Hs.448979 |
| 200898_s_at | 190 | NM_012215/ 943 | | | MGEA5 | Hs.500842 |
| 215519_x_at | 191 | NM_015705/ 981 | | | RUTBC3 | Hs.474914 |
| 212406_s_at | 192 | NM_018257/ 1005 | | | C20ORF36 | Hs.473317 |

TABLE 2-continued

| PROBESET | SEQ ID NO: | Refseq Ids/SEQ ID NO: | | | | | | | | REFSEQ_UNIGENE | REFSEQ_BAND |
|---|---|---|---|---|---|---|---|---|---|---|---|
| 210826_x_at | 193 | NM_133341/ 1066 | NM_133339/ 1151 | NM_133340/ 1200 | NM_133344/ 1224 | NM_133343/ 1239 | NM_133342/ 1237 | NM_133338/ 1243 | NM_002873/ 1246 | RAD17, RAD17, RAD17, RAD17, RAD17, RAD17, RAD17, ALG12 | Hs.16184, Hs.16184, Hs.16184, Hs.16184, Hs.16184, Hs.16184, Hs.16184, Hs.526711 |
| 218444_at | 194 | NM_024105/ 1043 | | | | | | | | LOC112869 | Hs.460487 |
| 221822_at | 195 | NM_138414/ 1070 | | | | | | | | C6ORF48 | Hs.109798 |
| 220755_s_at | 196 | NM_016947/ 992 | | | | | | | | CUTC | Hs.16606 |
| 218970_s_at | 197 | NM_015960/ 983 | | | | | | | | LGTN | Hs.497581 |
| 218253_s_at | 198 | NM_006893/ 933 | | | | | | | | DEF6 | Hs.15476 |
| 221293_s_at | 199 | NM_022047/ 1032 | | | | | | | | WAC, WAC, WAC, | Hs.435610, Hs.435610, Hs.435610, |
| 217742_s_at | 200 | NM_100486/ 1063 | NM_016628/ 1140 | NM_100264/ 1199 | | | | | | HNRPH3, HNRPH3, | Hs.499891, Hs.499891, |
| 207127_s_at | 201 | NM_021644/ 1030 | NM_012207/ 1136 | | | | | | | GNL3, GNL3, GNL3, | Hs.313544, Hs.313544, Hs.313544, |
| 217850_at | 202 | NM_206826/ 1104 | NM_014366/ 1137 | NM_206825/ 1213 | | | | | | KIAA0892 | Hs.112751 |
| 212505_s_at | 203 | NM_015329/ 974 | | | | | | | | LRPPRC | Hs.368084 |
| 211971_s_at | 204 | NM_133259/ 1065 | | | | | | | | | |
| 216387_x_at | 205 | NM_013269/ 952 | NM_001004420/ 1117 | NM_001004419/ 1185 | NM_002520/ 1218 | | | | | OCIL, OCIL, OCIL, NPM1, HMG20A | Hs.268326, Hs.268326, Hs.268326, Hs.519452, Hs.69594 |
| 218152_at | 206 | NM_018200/ 1002 | | | | | | | | | |
| 201788_at | 207 | NM_203499/ 1102 | NM_007372/ 1135 | | | | | | | DDX42, DDX42, TINP1 | Hs.8765, Hs.8765, Hs.482526 |
| 201922_at | 208 | NM_014886/ 966 | | | | | | | | | |
| 212982_at | 209 | NM_015336/ 975 | | | | | | | | ZDHHC17 | Hs.4014 |
| 214173_x_at | 210 | NM_134447/ 1068 | | | | | | | | C19ORF2, C19ORF2, | Hs.466391, Hs.466391, |
| 211937_at | 211 | NM_001417/ 852 | NM_003796/ 1128 | | | | | | | EIF4B | Hs.512629 |

TABLE 2-continued

| PROBESET | SEQ ID NO: | Refseq Ids/SEQ ID NO: | | | | | | | REFSEQ_UNIGENE | REFSEQ_BAND |
|---|---|---|---|---|---|---|---|---|---|---|
| 216843_x_at | 212 | NM_000535/ 828 | NM_174930/ 1086 | NM_002679/ 867 | NM_005395/ 908 | NM_001003686/ 1115 | NM_001003687/ 1183 | NM_032958/ 1242 | NM_032959/ 1247 | PMS2, PMS2, L5, POM121, PMS2L3, PMS2L3, PMS2L3, POLR2I2, POLR2I2, | Hs.487470, Hs.397073, Hs.488624, Hs.549057, Hs.549057, Hs.549057, Hs.433879, Hs.433879, |
| 212854_x_at | 213 | NM_032264/ 1056 | NM_173638/ 1166 | NM_183372/ 1209 | | | | | | AE2, MGC8902, LOC200030, DKFZP434C171 | Hs.325422, Hs.512037, Hs.515837, Hs.132994 |
| 212886_at | 214 | NM_015621/ 978 | | | | | | | | | |
| 220607_x_at | 215 | NM_016397/ 990 | NM_198976/ 1172 | | | | | | | TH1L, TH1L, C19ORF13 | Hs.517148, Hs.517148, Hs.407368 |
| 212132_at | 216 | NM_015578/ 977 | | | | | | | | | |
| 214042_s_at | 217 | NM_000983/ 839 | | | | | | | | RPL22 | Hs.515329 |
| 212660_at | 218 | NM_015288/ 972 | | | | | | | | PHF15 | Hs.483419 |
| 208944_at 210011_s_at | 219 220 | — NM_013986/ 956 | NM_005243/ 1130 | | | | | | | — EWSR1, EWSR1, EIF4B | — Hs.374477, Hs.374477, Hs.512629 |
| 211938_at | 221 | NM_001417/ 852 | | | | | | | | | |
| 220408_x_at | 222 | NM_017569/ 994 | | | | | | | | FAM48A | Hs.435815 |
| 212114_at 212455_at | 223 224 | — NM_133370/ 1067 | | | | | | | | — YT521 | — Hs.175955 |
| 212299_at 200005_at | 225 226 | — NM_003753/ 879 | | | | | | | | — EIF3S7 | — Hs.55682 |
| 200081_s_at | 227 | NM_001010/ 846 | | | | | | | | RPS6 | Hs.408073 |
| 213687_s_at | 228 | NM_000996/ 840 | | | | | | | | RPL35A | Hs.529631 |
| 204102_s_at | 229 | NM_001961/ 859 | | | | | | | | EEF2 | Hs.515070 |
| 211666_x_at | 230 | NM_000967/ 836 | | | | | | | | RPL3 | Hs.119598 |
| 209134_s_at | 231 | NM_001010/ 846 | | | | | | | | RPS6 | Hs.408073 |
| 221700_s_at | 232 | NM_003333/ 876 | | | | | | | | UBA52 | Hs.5308 |
| 200034_s_at | 233 | NM_000970/ 837 | | | | | | | | RPL6 | Hs.528668 |

TABLE 2-continued

| PROBESET | SEQ ID NO: | Refseq Ids/SEQ ID NO: | | | REFSEQ_UNIGENE | REFSEQ_BAND |
|---|---|---|---|---|---|---|
| 201254_x_at | 234 | NM_001010/ 846 | | | RPS6 | Hs.408073 |
| 212734_x_at | 235 | NM_000977/ 838 | NM_033251/ 1147 | | RPL13, RPL13, | Hs.410817, Hs.410817, |
| 217718_s_at | 236 | NM_139323/ 1073 | NM_003404/ 1126 | | YWHAB, YWHAB, | Hs.279920, Hs.279920, |
| 208678_at | 237 | NM_001696/ 855 | | | ATP6V1E1 | Hs.517338 |
| 200633_at | 238 | NM_018955/ 1014 | | | UBB | Hs.356190 |
| 201318_s_at | 239 | NM_033546/ 1058 | NM_006471/ 1134 | | MRLC2, MRCL3, | Hs.464472, Hs.190086, |
| 202090_s_at | 240 | NM_006830/ 931 | | | UQCR | Hs.8372 |
| 221474_at | 241 | NM_033546/ 1058 | | | MRLC2 | Hs.464472 |
| 214629_x_at | 242 | NM_153828/ 1080 | NM_207520/ 1176 | NM_207521/ 1214 | RTN4, RTN4, RTN4, RTN4, | Hs.429581, Hs.429581, Hs.429581, Hs.429581, |
| 200067_x_at | 243 | NM_152827/ 1078 | NM_003795/ 1127 | NM_152828/ 1203 | SNX3, SNX3, SNX3, | Hs.12102, Hs.12102, Hs.12102, |
| 201899_s_at | 244 | NM_181762/ 1089 | NM_003336/ 1125 | NM_181777/ 1207 | UBE2A, UBE2A, UBE2A, | Hs.379466, Hs.379466, Hs.379466, |
| 210968_s_at | 245 | NM_153828/ 1080 | NM_207520/ 1176 | NM_207521/ 1214 NM_020532/ 1221 NM_007008/ 1236 | RTN4, RTN4, RTN4, RTN4, RTN4, | Hs.429581, Hs.429581, Hs.429581, Hs.429581, Hs.429581, |
| 200609_s_at | 246 | NM_005112/ 904 | NM_017491/ 1142 | | WDR1, WDR1, | Hs.128548, Hs.128548, |
| 208805_at | 247 | NM_002791/ 868 | | | PSMA6 | Hs.446260 |
| 218571_s_at | 248 | NM_014169/ 957 | | | C14ORF123 | Hs.279761 |
| 217730_at | 249 | NM_022152/ 1035 | | | PP1201 | Hs.98475 |
| 218520_at | 250 | NM_013254/ 951 | | | TBK1 | Hs.505874 |
| 208908_s_at | 251 | NM_173061/ 1085 | NM_173062/ 1165 | NM_173060/ 1084 NM_001750/ 1217 | CAST, CAST, CAST, CAST, | Hs.440961, Hs.440961, Hs.440961, Hs.440961, |
| 207467_x_at | 252 | NM_173061/ 1085 | NM_173062/ 1165 | NM_173060/ 1084 NM_001750/ 1217 | CAST, CAST, CAST, CAST, | Hs.440961, Hs.440961, Hs.440961, Hs.440961, |

TABLE 2-continued

| PROBESET | SEQ ID NO: | Refseq Ids/SEQ ID NO: | REFSEQ_UNIGENE | REFSEQ_BAND |
|---|---|---|---|---|
| 201975_at | 253 | NM_198240/1093 | RSN, RSN, | Hs.524809, Hs.524809, |
| 200814_at | 254 | NM_006263/920 | PSME1, PSME1, | Hs.75348, Hs.75348, |
| 203090_at | 255 | NM_006923/934 | SDF2 | Hs.514036 |
| 201470_at | 256 | NM_004832/895 | GSTO1 | Hs.190028 |
| 212586_at | 257 | NM_173060/1084 | CAST | Hs.440961 |
| 200703_at | 258 | NM_003746/878 | DNCL1 | Hs.5120 |
| 217995_at | 259 | NM_021199/1029 | SQRDL | Hs.511251 |
| 201346_at | 260 | NM_024551/1048 | ADIPOR2 | Hs.371642 |
| 201609_x_at | 261 | NM_012405/949 | ICMT, ICMT, | Hs.515688, Hs.515688, |
| 202000_at | 262 | NM_002490/864 | NDUFA6 | Hs.274416 |
| 202001_s_at | 263 | NM_002490/864 | NDUFA6 | Hs.274416 |
| 203880_at | 264 | NM_005694/914 | COX17 | Hs.534383 |
| 218525_s_at | 265 | NM_017902/995 | HIF1AN | Hs.500788 |
| 219798_s_at | 266 | NM_019606/1017 | FLJ20257 | Hs.178011 |
| 208398_s_at | 267 | NM_004865/897 | TBPL1 | Hs.486507 |
| 218358_at | 268 | NM_024324/1045 | MGC11256 | Hs.211282 |
| 203097_s_at | 269 | —/— | — | — |
| 221598_s_at | 270 | NM_004269/887 | CRS98 | Hs.374262 |
| 209546_s_at | 271 | AF323540/811 | GenBank | Hs.114309 |
| 50400_at | 272 | AI743990/812 | GenBank | Hs.24859 |
| 217752_s_at | 273 | NM_018235/1003 | GenBank | Hs.273230 |
| 201931_at | 274 | NM_000126/825 | GenBank | Hs.169919 |
| 218567_x_at | 275 | NM_005700/915 | GenBank | Hs.22880 |
| 202056_at | 276 | AW051311/816 | GenBank | Hs.169149 |
| 218907_s_at | 277 | NM_023942/1041 | GenBank | Hs.284135 |

TABLE 2-continued

| PROBESET | SEQ ID NO: | Refseq Ids/SEQ ID NO: | REFSEQ_UNIGENE | REFSEQ_BAND |
|---|---|---|---|---|
| 213726_x_at | 278 | AA515698/806 | GenBank | Hs.251653 |
| 204448_s_at | 279 | AF031463/808 | GenBank | Hs.9302 |
| 1405_i_at | 280 | M21121/823 | GenBank | — |
| 212864_at | 281 | Y16521/1108 | GenBank | Hs.24812 |
| 209444_at | 282 | BC001851/819 | GenBank | Hs.7940 |
| 208898_at | 283 | AF077614/809 | GenBank | Hs.272630 |
| 202377_at | 284 | AW026535/815 | GenBank | Hs.23581 |
| 209547_s_at | 285 | BC001043/818 | GenBank | Hs.15075 |
| 202922_at | 286 | BF676980/821 | GenBank | Hs.151393 |
| 201403_s_at | 287 | NM_004528/892 | GenBank | Hs.111811 |
| 213154_s_at | 288 | AI934125/814 | GenBank | Hs.17411 |
| 215676_at | 289 | N91109/824 | GenBank | Hs.32935 |
| 218927_s_at | 290 | NM_018641/1012 | GenBank | Hs.25204 |
| 213648_at | 291 | AW614427/817 | GenBank | Hs.182877 |
| 209593_s_at | 292 | AF317129/810 | GenBank | Hs.252682 |
| 203731_s_at | 293 | NM_014569/960 | GenBank | Hs.110839 |
| 201234_at | 294 | NM_004517/891 | GenBank | Hs.6196 |
| 214817_at | 295 | BE783668/820 | GenBank | Hs.175780 |
| 201761_at | 296 | NM_006636/929 | GenBank | Hs.154672 |
| 205467_at | 297 | NM_001230/850 | GenBank | Hs.5353 |
| 222318_at | 298 | AI744673/813 | GenBank | Hs.186970 |
| 209933_s_at | 299 | AF020314/807 | GenBank | Hs.9688 |
| 200734_s_at | 300 | BG341906/822 | GenBank | Hs.119177 |
| 219899_x_at | 301 | NM_014434/959 | NDOR1 | Hs.512564 |

TABLE 2-continued

| PROBESET | SEQ ID NO: | Refseq Ids/SEQ ID NO: | | | REFSEQ_UNIGENE | REFSEQ_BAND |
|---|---|---|---|---|---|---|
| 221563_at | 302 | NM_144729/ 1074 | NM_144728/ 1155 | NM_007207/ 1192 | DUSP10, DUSP10, DUSP10, | Hs.497822, Hs.497822, Hs.497822, |
| 65517_at | 303 | NM_005498/ 910 | | | AP1M2 | Hs.18894 |
| 205126_at | 304 | NM_006296/ 921 | | | VRK2 | Hs.468623 |
| 200696_s_at | 305 | NM_198252/ 1094 | NM_000177/ 1110 | | GSN, GSN, | Hs.522373, Hs.522373, |
| 208790_s_at | 306 | NM_012232/ 944 | | | PTRF | Hs.437191 |
| 205115_s_at | 307 | NM_016196/ 987 | | | RBM19 | Hs.7482 |
| 213982_s_at | 308 | NM_014857/ 965 | | | RABGAP1L | Hs.495391 |
| 206992_s_at | 309 | NM_015684/ 980 | NM_001003805/ 1116 | NM_001003803/ 1184 | ATP5S, ATP5S, ATP5S, | Hs.438489, Hs.438489, Hs.438489, |
| 201060_x_at | 310 | NM_198194/ 1092 | NM_004099/ 1129 | NM_017723/ 1195 | STOM, STOM, FLJ20245, | Hs.253903, Hs.253903, Hs.495541, |
| 209278_s_at | 311 | NM_006528/ 924 | | | TFPI2 | Hs.438231 |
| 210542_s_at 202006_at | 312 313 | —/ NM_002835/ 869 | | | — PTPN12 | — Hs.61812 |
| 210557_x_at | 314 | NM_172211/ 1082 | NM_000757/ 1112 | NM_172210/ 1205 | CSF1, CSF1, CSF1, CSF1, | Hs.173894, Hs.173894, Hs.173894, Hs.173894, |
| 210796_x_at | 315 | NM_198846/ 1097 | NM_198845/ 1171 | NM_001245/ 1188 | SIGLEC6, SIGLEC6, SIGLEC6, | Hs.397255, Hs.397255, Hs.397255, |
| 220825_s_at | 316 | NM_018240/ 1004 | | | KIRREL | Hs.272234 |
| 202378_s_at | 317 | NM_017526/ 993 | | | LEPR | Hs.23581 |
| 210241_s_at | 318 | NM_007233/ 936 | | | TP53AP1 | Hs.274329 |
| 213069_at 216034_at | 319 320 | —/ NM_080740/ 1061 | | | — SUHW1 | — Hs.178665 |

TABLE 2-continued

| PROBESET | SEQ ID NO: | Refseq Ids/SEQ ID NO: | | | | REFSEQ_UNIGENE | REFSEQ_BAND |
|---|---|---|---|---|---|---|---|
| 210793_s_at | 321 | NM_139131/ 1072 | NM_005387/ 1131 | | | NUP98, NUP98, | Hs.524750, Hs.524750 |
| 207375_s_at | 322 | NM_002189/ 860 | NM_172200/ 1163 | | | IL15RA, IL15RA, | Hs.524117, Hs.524117, |
| 206247_at | 323 | NM_005931/ 917 | | | | MICB | Hs.211580 |
| 217078_s_at | 324 | NM_007261/ 937 | | | | CMRF-35H | Hs.9688 |
| 219257_s_at | 325 | NM_021972/ 1031 | NM_182965/ 1170 | | | SPHK1, SPHK1, | Hs.68061, Hs.68061, |
| 204781_s_at | 326 | NM_152876/ 1079 | NM_152877/ 1161 | NM_152874/ 1204 | NM_152875/ 1225 | NM_152873/ 1238 | NM_152871/ 1240 | NM_152872/ 1244 | NM_000043/ 1245 | FAS, FAS, FAS, FAS, FAS, FAS, FAS, | Hs.244139, Hs.244139, Hs.244139, Hs.244139, Hs.244139, Hs.244139, Hs.244139, |
| 221536_s_at | 327 | NM_018385/ 1009 | | | | FLJ11301 | Hs.518505 |
| 209468_at | 328 | NM_002335/ 861 | | | | LRP5 | Hs.6347 |
| 201061_s_at | 329 | NM_198194/ 1092 | NM_004099 1129 | | | STOM, STOM, | Hs.253903, Hs.253903, |
| 203499_at | 330 | NM_004431/ 889 | | | | EPHA2 | Hs.171596 |
| 213324_at | 331 | NM_198291/ 1095 | NM_005417/ 1132 | | | SRC, SRC, | Hs.195659, Hs.195659, |
| 221535_at | 332 | NM_018385/ 1009 | | | | FLJ11301 | Hs.518505 |
| 219938_s_at | 333 | NM_024430/ 1046 | | | | PSTPIP2 | Hs.368623 |
| 213787_s_at | 334 | NM_006579/ 926 | | | | EBP | Hs.522636 |
| 219592_at | 335 | NM_024596/ 1049 | | | | MCPH1 | Hs.550532 |
| 200637_s_at | 336 | NM_130440/ 1064 | NM_002840/ 1122 | | | PTPRF, PTPRF, | Hs.272062, Hs.272062, |
| 202193_at | 337 | NM_005569/ 913 | NM_016733/ 1141 | | | LIMK2, LIMK2, | Hs.474596, Hs.474596, |
| 214859_at | 338 | NM_015082/ 969 | | | | FSTL4 | Hs.483390 |
| 209213_at | 339 | NM_001757/ 857 | | | | CBR1 | Hs.88778 |

TABLE 2-continued

| PROBESET | SEQ ID NO: | Refseq Ids/SEQ ID NO: | | | | REFSEQ_UNIGENE | REFSEQ_BAND |
|---|---|---|---|---|---|---|---|
| 218945_at | 340 | NM_024109/ 1044 | | | | MGC2654 | Hs.306380 |
| 220471_s_at | 341 | NM_025107/ 1052 | | | | MYCT1 | Hs.18160 |
| 59625_at | 342 | NM_003946/ 883 | | | | NOL3 | Hs.513667 |
| 207233_s_at | 343 | NM_198158/ 1091 | NM_198178/ 1210 | NM_198177/ 1228 | NM_006722/ 1235 | NM_198159/ 1241 | MITF, MITF, MITF, MITF, MITF, MITF, | Hs.166017, Hs.166017, Hs.166017, Hs.166017, Hs.166017, Hs.166017, |
| 214070_s_at | 344 | —/— | | | | — | — |
| 219785_s_at | 345 | —/— | | | | — | — |
| 220684_at | 346 | NM_013351/ 954 | | | | TBX21 | Hs.272409 |
| 202245_at | 347 | NM_002340/ 862 | | | | LSS | Hs.517366 |
| 207298_at | 348 | NM_006632/ 927 | | | | SLC17A3 | Hs.327179 |
| 220201_at | 349 | NM_018835/ 1013 | | | | MNAB | Hs.533499 |
| 203208_s_at | 350 | NM_014637/ 961 | | | | CHPPR | Hs.521608 |
| 207033_at | 351 | NM_051142/ 906 | | | | GIF | Hs.110014 |
| 204929_s_at | 352 | NM_006634/ 928 | | | | VAMP5 | Hs.172684 |
| 209735_at | 353 | NM_004827/ 894 | | | | ABCG2 | Hs.480218 |
| 209234_at | 354 | NM_015074/ 968 | | | | KIF1B | Hs.97858 |
| 210102_at | 355 | NM_198315/ 1096 | | | | LOH11CR2A | Hs.152944 |
| 204114_at | 356 | NM_007361/ 941 | | | | NID2 | Hs.369840 |
| 203344_s_at | 357 | NM_203292/ 1100 | NM_203291/ 1174 | NM_002894/ 1190 | | | RBBP8, RBBP8, RBBP8, | Hs.546282, Hs.546282, Hs.546282, |
| 216891_at | 358 | —/— | | | | — | — |
| 221680_s_at | 359 | NM_016135/ 986 | NM_145918/ 1159 | | | | ETV7 | Hs.272398 |
| 202087_s_at | 360 | NM_001912/ 858 | NM_005417/ 1132 | | | | CTSL, CTSL, | Hs.418123, Hs.418123, |
| 213324_at | 331 | NM_198291/ 1095 | | | | | SRC, SRC, | Hs.195659, Hs.195659, |
| 221535_at | 332 | NM_018385/ 1009 | | | | | FLJ11301 | Hs.518505 |

TABLE 2-continued

| PROBESET | SEQ ID NO: | Refseq Ids/SEQ ID NO: | | | | REFSEQ_UNIGENE | REFSEQ_BAND |
|---|---|---|---|---|---|---|---|
| 219938_s_at | 333 | NM_024430/ 1046 | | | | PSTPIP2 | Hs.368623 |
| 213787_s_at | 334 | NM_006579/ 926 | | | | EBP | Hs.522636 |
| 219592_at | 335 | NM_024596/ 1049 | | | | MCPH1 | Hs.550532 |
| 200637_s_at | 336 | NM_130440/ 1064 | NM_002840/ 1122 | | | PTPRF, PTPRF, | Hs.272062, Hs.272062, |
| 202193_at | 337 | NM_005569/ 913 | NM_016733/ 1141 | | | LIMK 2, LIMK 2, | Hs.474596, Hs.474596, |
| 214859_at | 338 | NM_015082/ 969 | | | | FSTL4 | Hs.483390 |
| 209213_at | 339 | NM_001757/ 857 | | | | CBR1 | Hs.88778 |
| 218945_at | 340 | NM_024109/ 1044 | | | | MGC2654 | Hs.306380 |
| 220471_s_at | 341 | NM_025107/ 1052 | | | | MYCT1 | Hs.18160 |
| 59625_at | 342 | NM_003946/ 883 | | | | NOL3 | Hs.513667 |
| 207233_s_at | 343 | NM_198158/ 1091 | NM_198178/ 1210 | NM_198177/ 1228 | NM_006722/ 1235 | MITF, MITF, MITF, MITF, MITF, | Hs.166017, Hs.166017, Hs.166017, Hs.166017, Hs.166017, |
| 214070_s_at | 344 | —/ | | | NM_198159/ 1241 | — | — |
| 219785_s_at | 345 | —/ | | | | — | — |
| 220684_at | 346 | NM_013351/ 954 | | | | TBX21 | Hs.272409 |
| 202245_at | 347 | NM_002340/ 862 | | | | LSS | Hs.517366 |
| 207298_at | 348 | NM_006632/ 927 | | | | SLC17A3 | Hs.327179 |
| 220201_at | 349 | NM_018835/ 1013 | | | | MNAB | Hs.533499 |
| 203208_s_at | 350 | NM_014637/ 961 | | | | CHPPR | Hs.521608 |
| 207033_at | 351 | NM_005142/ 906 | | | | GIF | Hs.110014 |
| 204929_s_at | 352 | NM_006634/ 928 | | | | VAMP5 | Hs.172684 |
| 209735_at | 353 | NM_004827/ 894 | | | | ABCG2 | Hs.480218 |
| 209234_at | 354 | NM_015074/ 968 | | | | KIF1B | Hs.97858 |
| 210102_at | 355 | NM_198315/ 1096 | | | | LOH11CR2A | Hs.152944 |

TABLE 2-continued

| PROBESET | SEQ ID NO: | Refseq Ids/SEQ ID NO: | | REFSEQ_UNIGENE | REFSEQ_BAND |
|---|---|---|---|---|---|
| 204114_at | 356 | NM_007361/ 941 | | NID2 | Hs.369840 |
| 203344_s_at | 357 | NM_203292/ 1100 | NM_203291/ 1174 | RBBP8, RBBP8, RBBP8, | Hs.546282, Hs.546282, Hs.546282, |
| 216891_at | 358 | —/— | | — | — |
| 221680_s_at | 359 | NM_016135/ 986 | | ETV7 | Hs.272398 |
| 202087_s_at | 360 | NM_001912/ 858 | NM_145918/ 1159 | CTSL, CTSL, SIAT8A | Hs.418123, Hs.418123, Hs.408614 |
| 210073_at | 391 | NM_003034/ 871 | | | |
| 209524_at | 392 | NM_016073/ 985 | | HDGFRP3 | Hs.513954 |
| 219759_at | 393 | NM_022350/ 1036 | | LRAP | Hs.482910 |
| 202112_at | 394 | NM_000552/ 830 | | VWF | Hs.440848 |
| 219410_at | 395 | NM_018004/ 1000 | | FLJ10134 | Hs.126598 |
| 203819_s_at | 396 | NM_006547/ 925 | | IMP-3 | Hs.432616 |
| 212730_at | 397 | NM_015286/ 971 | NM_145728/ 1158 | DMN, DMN, | Hs.207106, Hs.207106, |
| 220122_at | 398 | —/— | | — | — |
| 208782_at | 399 | NM_007085/ 935 | | FSTL1 | Hs.269512 |
| 202468_s_at | 400 | NM_003798/ 882 | | CTNNAL1 | Hs.58488 |
| 207018_s_at | 401 | NM_004163/ 886 | | RAB27B | Hs.25318 |
| 210354_at | 402 | NM_000619/ 832 | | IFNG | Hs.856 |
| 201110_s_at | 403 | NM_003246/ 874 | | THBS1 | Hs.164226 |
| 207808_s_at | 404 | NM_000313/ 827 | | PROS1 | Hs.64016 |
| 205612_at | 405 | NM_007351/ 940 | | MMRN1 | Hs.268107 |
| 214073_at | 406 | —/— | | — | — |

The genes encoding RNA polymerase I transcription factor (RRN3) and leucine-rich PPR-motif containing protein (LRPRC) were found as most significantly down-regulated genes in BMS signature (Table 1, hereinabove). RRN33 (transcription initiation factor TIF-IA), a 72-kDa protein, is essential for ribosomal DNA (rDNA) transcription and acts as a bridge between RNA pol I and the committed rDNA promoter (Hirschler-Laszkiewicz I, et al., 2003; Miller G, et al., 2001; 20:1373-1382). The suppression of polymerase I regulation mechanism is confirmed by down-regulation of polymerase (RNA) I polypeptide D (POLR1D).

LRPPRC is a candidate gene for the French-Canadian type of Leigh syndrome, a form of cytochrome c oxidase deficiency, and plays a role in translation or stability of mitochondrially encoded cytochrome c oxidase (COX) subunits (Mootha V K, et al., 2003). The LRPPC together with POLR1D molecules comprise a complex with NFkBIB protein (Bouwmeester T, et al., 2004) that inhibits proinflammatory NFkB pathway.

Without being bound by any theory, the suppression of molecules involved in polymerase I related mechanism, COXI and NFkB regulation could account for the differences between BMS and typical RRMS patients. In addition, the polymerase I related mechanism can be potential drug targets for the treatment of RRMS aimed to switch RRMS to the BMS variant. One of commercially available drug that has proven effects on polymerase I mechanism is a diterpenoid triepoxide Triptolide (TPT), isolated from the Chinese herb *Tripterygium wilfordii* (Leuenroth S J and Crews C M. Triptolide-induced transcriptional arrest is associated with changes in nuclear substructure. Cancer Res. 2008; 68:5257-5266). Triptolide has various anti-inflammatory effects (Liu Y, et al. Triptolide, a component of Chinese herbal medicine, modulates the functional phenotype of dendritic cells. Transplantation. 2007; 84:1517-1526), it modulates T-cell inflammatory responses and ameliorates Experimental Autoimmune Encephalomyelitis (Wang Y, et al. Triptolide modulates T-cell inflammatory responses and ameliorates experimental autoimmune encephalomyelitis. J Neurosci Res. 2008; 86:2441-2449).

More specifically TPT demonstrated to suppress of T lymphocyte function including T cell apoptosis induction, inhibition of lymphocyte proliheration and IFNγ production (Chen B J. 2001. Triptolide, a novel immunosuppressive and anti-inflammatory agent purified from a Chinese herb *Tripterygium wilfordii* Hook f. Leuk Lymphoma 42:253-265; Qiu D, Kao P N. 2003 Immunosuppressive and anti-inflammatory mechanisms of triptolide, the principal active diterpenoid from the Chinese medicinal herb *Tripterygium wilfordii* Hook f. Drugs R D 4:1-18; Yang Y, Liu Z, Tolosa E, Yang J, Li L. 1998. Triptolide induces apoptotic death of T lymphocyte. Immunopharmacology 40:139-149; Chan M A, Kohlmeier J E, Branden M, Jung M, Benedict S H. 1999. Triptolide is more effective in preventing T cell proliferation and interferon-gamma production than is FK506. Phytother Res 13:464-467). The TPT decreased IL2 and IL2 receptor expression by inhibiting activation of the purine box regulator of the NFkB of activated T cells (Qiu 1999). Additionally, it was demonstrated that TPT can inhibit the maturation, antigen processing, and presentation of dendritic cells and can suppress tumor necrosis factor (TNF)-a and IL-6 production by activated macrophages (Zhu K J, Shen Q Y, Cheng H, Mao X H, Lao L M, Hao G L. 2005. Triptolide affects the differentiation, maturation and function of human dendritic cells. Int Immunopharmacol 5:1415-1426; Wu Y, Cui J, Bao X, Chan S, Young D O, Liu D, Shen P. 2006. Triptolide attenuates oxidative stress, NF-kappaB activation and multiple cytokine gene expression in murine peritoneal macrophage. Int J Mol Med 17:141-150).

Table 3, hereinbelow, discloses the genes involved in the RNA polymerase I pathway, which are likely to be involved in typical RRMS or BMS pathology.

TABLE 3

Genes involved in the RNA polymerase I pathway

| Affymetrix ProbSet | SEQ ID NO: | Representative Public ID/SEQ ID NO: | Gene Symbol | Gene Title |
|---|---|---|---|---|
| 216902_s_at | 62 | AF001549/1284; NM_018427/1285 | RRN3 | RRN3 RNA polymerase I transcription factor homolog |
| 211971_s_at | 204 | AI653608/1286; NM_133259/1287 | LRPPRC | leucine-rich PPR-motif containing |
| 220113_x_at | 1248 | NM_019014/1288 | POLR1B | polymerase (RNA) I polypeptide B, 128 kDa |
| 207515_s_at | 1249 | NM_004875/1289 | POLR1C | polymerase (RNA) I polypeptide C, 30 kDa |
| 209317_at | 1250 | AF008442/1290 | POLR1C | polymerase (RNA) I polypeptide C, 30 kDa |
| 218258_at | 173 | NM_015972/1291 | POLR1D | polymerase (RNA) I polypeptide D, 16 kDa |
| 202725_at | 1251 | NM_000937/1292 | POLR2A | polymerase (RNA) II (DNA directed) polypeptide A, 220 kDa |
| 217420_s_at | 1252 | M21610/1293 | POLR2A | polymerase (RNA) II (DNA directed) polypeptide A, 220 kDa |
| 201803_at | 1253 | NM_000938/1294 | POLR2B | polymerase (RNA) II (DNA directed) polypeptide B, 140 kDa |
| 208996_s_at | 1254 | BC000409/1295 | POLR2C | polymerase (RNA) II (DNA directed) polypeptide C, 33 kDa |
| 214263_x_at | 1255 | AI192781/1296 | POLR2C | polymerase (RNA) II (DNA directed) polypeptide C, 33 kDa |
| 216282_x_at | 1256 | AJ224143/1297 | POLR2C | polymerase (RNA) II (DNA directed) polypeptide C, 33 kDa |
| 203664_s_at | 1257 | NM_004805/1298 | POLR2D | polymerase (RNA) II (DNA directed) polypeptide D |

TABLE 3-continued

Genes involved in the RNA polymerase I pathway

| Affymetrix ProbSet | SEQ ID NO: | Representative Public ID/SEQ ID NO: | Gene Symbol | Gene Title |
|---|---|---|---|---|
| 214144_at | 1258 | BF432147/1299 | POLR2D | polymerase (RNA) II (DNA directed) polypeptide D |
| 213887_s_at | 1259 | AI554759/1300 | POLR2E | polymerase (RNA) II (DNA directed) polypeptide E, 25 kDa |
| 217854_s_at | 1260 | BC004441/1301 | POLR2E | polymerase (RNA) II (DNA directed) polypeptide E, 25 kDa |
| 209511_at | 1261 | BC003582/1302 | POLR2F | polymerase (RNA) II (DNA directed) polypeptide F |
| 202306_at | 1262 | NM_002696/1303 | POLR2G | polymerase (RNA) II (DNA directed) polypeptide G |
| 209302_at | 1263 | U37689/1304 | POLR2H | polymerase (RNA) II (DNA directed) polypeptide H |
| 212955_s_at | 1264 | AL037557/1305 | POLR2I | polymerase (RNA) II (DNA directed) polypeptide I, 14.5 kDa |
| 212782_x_at | 1265 | BG335629/1306 | POLR2J | polymerase (RNA) II (DNA directed) polypeptide J, 13.3 kDa |
| 216242_x_at | 1266 | AW402635/1307 | POLR2J2 | DNA directed RNA polymerase II polypeptide J-related gene |
| 214740_at | 1267 | BE676209/1308 | POLR2J2 /// MGC13098 | DNA directed RNA polymerase II polypeptide J-related gene /// hypothetical prote |
| 202634_at | 1268 | AL558030/1309 | POLR2K | polymerase (RNA) II (DNA directed) polypeptide K, 7.0 kDa |
| 202635_s_at | 1269 | NM_005034/1310 | POLR2K | polymerase (RNA) II (DNA directed) polypeptide K, 7.0 kDa |
| 202586_at | 1270 | AA772747/1311 | POLR2L | polymerase (RNA) II (DNA directed) polypeptide L, 7.6 kDa |
| 211730_s_at | 1271 | BC005903/1312 | POLR2L | polymerase (RNA) II (DNA directed) polypeptide L, 7.6 kDa /// polymerase (RNA) II |
| 219459_at | 1272 | NM_018082/1313 | POLR3B | polymerase (RNA) III (DNA directed) polypeptide B |
| 209382_at | 1273 | U93867/1314 | POLR3C | polymerase (RNA) III (DNA directed) polypeptide C (62 kD) |
| 210573_s_at | 1274 | BC004424/1315 | POLR3C | polymerase (RNA) III (DNA directed) polypeptide C (62 kD) |
| 208361_s_at | 1275 | NM_001722/1316 | POLR3D | polymerase (RNA) III (DNA directed) polypeptide D, 44 kDa |
| 218016_s_at | 1276 | NM_018119/1317 | POLR3E | polymerase (RNA) III (DNA directed) polypeptide E (80 kD) |
| 205218_at | 1277 | NM_006466/1318 | POLR3F | polymerase (RNA) III (DNA directed) polypeptide F, 39 kDa |
| 206653_at | 1278 | BF062139/1319 | POLR3G | Polymerase (RNA) III (DNA directed) polypeptide G (32 kD) |
| 206654_s_at | 1279 | NM_006467/1320 | POLR3G | polymerase (RNA) III (DNA directed) polypeptide G (32 kD) |
| 218866_s_at | 1280 | AF060223/1321 | POLR3K | polymerase (RNA) III (DNA directed) polypeptide K, 12.3 kDa |
| 203782_s_at | 1281 | NM_005035/1322 | POLRMT | polymerase (RNA) mitochondrial (DNA directed) |
| 203783_x_at | 1282 | BF057617/1323 | POLRMT | polymerase (RNA) mitochondrial (DNA directed) |
| 202466_at | 1283 | NM_006999/1324 | POLS | polymerase (DNA directed) sigma |

The measurement of RRN3, LRPPRC, POLR1D and other polymerase I mechanism related biomarkers could be used for diagnosis and prediction of BMS. Additionally those markers could be useful for typical RRMS patients to monitor the efficacy of various immunomodulatory drugs for assessment of patients with good response to treatment.

Measurement of BMS biomarkers can be performed on the mRNA level by the quantitative reverse-transcriptase polymerase chain reaction (QRT-PCR) method and on protein level by LUMINEX technology. Possible modification of the invention is developing biomarkers on protein level (e.g., using ELISA, Western Blot analysis and the like) in PBMC and serum.

Multiple sclerosis (MS) is a heterogeneous disease. To better diagnose and treat MS patients the various types of disease have to be distinguished. The teachings of the invention enable, for the first time, to distinguish between BMS and typical RRMS patients using molecular tools, which when combined with accurate clinical information enables to dissect the biological complexity of MS.

In the current study the use of gene expression profiling enabled to diagnose benign MS using a phenotypic approach to differentiate subtypes of the disease. The identified gene expression phenotypes also enable to better understand the biology of benign MS and to develop therapeutics strategies to treat MS.

The gene expression signature generated herein of benign MS enables refining MS to diagnose low risk patients versus high risk patients and accordingly suggest appropriate treatment.

The benign MS patients that represent low risk would not be treated while the high risk relapsing-remitting MS patients will be treated. In addition, the teachings of the invention enable to monitor response to treatment and better use of current approved medications.

The teachings of the invention can be used to develop a kit or device for diagnosis and prediction of typical RRMS clinical outcome, improving medical decision support systems and individualizing patient care. In addition, the teachings of the invention can be used to develop new drugs that will imitate BMS gene expression signature and will result in silencing of the active RRMS.

Example 2

Study Subject and Methods
Subjects—
31 patients (age 44.5±1.5; female to male ratio 24:7) with BMS were characterized by mean EDSS 1.95±0.15, disease duration 17.0±1.3 years, annual EDSS rate 0.13±0.01, annual relapse rate 0.23±0.04. 36 patients (age 40.3±1.8; female to male ratio 8:3) with RRMS were characterized by mean EDSS 3.54±0.23, disease duration 10.9±1.4 years, annual EDSS rate 0.45±0.06, annual relapse rate 0.64±0.09.

RNA Isolation and Microarray Expression Profiling—
Peripheral blood mononuclear cells (PBMC) were separated on ficoll-hypaque gradient. Total RNA was isolated using the TRIzol Reagent (Invitrogen, Carlsbad, Calif.), and cDNA was synthesized, labeled and hybridized to HG-U133A-2 array (Affymetrix, Inc, Santa Clara, Calif.) containing 22,215 gene-transcripts, washed and scanned (Hewlett Packard, GeneArray-TM scanner G2500A) according to manufacturer's protocol Affymetrix (Inc, Santa Clara, Calif.).

Data Analysis—
Data analysis was performed using the Partek Genomics Solution software [World Wide Web (dot) partek (dot) com]. Expression values were computed from raw CEL (cells) files by applying the Robust Multi-Chip Average (RMA) background correction algorithm. The RMA correction included: 1) values background correction; 2) quantile normalization; 3) log 2 transformation; 4) median polish summarization. The gene transcripts were filtered using Affymetrix MASS Present/Absent Detection. Thereafter, 9987 transcript that were detected as Present in 100% microarrays were used for analysis. In order to avoid the noise caused by variable set effects each set was normalized to pre-saved distribution pattern of a well balanced set used as a reference distribution. To reduce batch effect ANOVA multiple model analysis was applied. Source of variation was analyzed; nuisance batches effects such as working batch, patient age, gender and treatment were eliminated. Most informative genes (MIGs) were defined as genes that passed Falls Discavery Rate (FDR) correction with p<0.05 by ANOVA linear contrasts model. Thereafter, predictive algorithm based on two level cross validation method, Super Vector Machine (SVM) and K-Nearest Neighbor algorithms were applied to calculate MIGs classification rates. Only genes which were included in classifiers (from 1 to 10 genes) with more than 70% correct classification rates were analyzed.

Experimental Results

Identification of Classification Rates of Genes Involved in the RNA Polymerase I Pathway Between Typical RRMS and BMS Disease Course—
Tables 4A-C presents the corrected classification rates for all combinations of RRN3, LRPPRC and POLR1D genes of the RNA polymerase I pathway for the entire BMS and typical RRMS group (Table 4A), for the BMS group (Table 4B) and for the typical RRMS group (Table 4C). The best predictive performance for each classifier is presented.

TABLE 4A

| Classifiers | Aver. % Correct | St. Err (%) |
|---|---|---|
| RRN3 | 63.6 | 11.2 |
| LRPPRC | 73.3 | 9.5 |
| POLR1D | 72.7 | 9.5 |
| RRN3, POLR1D | 72.7 | 9.5 |
| RRN3, LRPPRC | 63.6 | 10.2 |
| POLR1D, LRPPRC | 81.8 | 8.2 |
| RRN3, LRPPRC, POLR1D | 77.2 | 8.9 |

Average % correct = Average percent of correct classification between BMS and typical RRMS patients using specific classifier;
St. Err. = standard error;

TABLE 4B

| Classifiers | BMS % corr |
|---|---|
| RRN3 | 67 |
| LRPPRC | 80 |
| POLR1D | 60 |
| RRN3, POLR1D | 60 |
| RRN3, LRPPRC | 30 |
| POLR1D, LRPPRC | 80 |
| RRN3, LRPPRC, POLR1D | 70 |

BMS % Corr. = Average percent of correct classification for BMS patients using specific classifier;

TABLE 4C

| Classifiers | Typical RRMS % corr |
|---|---|
| RRN3 | 60 |
| LRPPRC | 67 |
| POLR1D | 80 |
| RRN3, POLR1D | 83 |
| RRN3, LRPPRC | 90 |
| POLR1D, LRPPRC | 83 |
| RRN3, LRPPRC, POLR1D | 83 |

RRMS % Corr. - Average percent of correct classification for typical RRMS patients using specific classifier.

The results presented in Table 4B demonstrate that for classification of BMS, each of the genes of the RNA polymerase I pathway, i.e., RRN3, LRPPRC and POLR1D exhibits a correct classification rate of 67%, 80% and 60%, respectively. The results presented in Table 4C demonstrate that for classification of typical RRMS, each of RRN3, LRPPRC and POLR1D exhibits a correct classification rate of 60%, 67% and 80%, respectively. In addition, an increased rate of correct classification of typical RRMS, which is a more complex and heterogenous condition, can be achieved using a combination of 2 or 3 genes of the RNA polymerase I pathway. For example, a correct classification rate of 83% is obtained using the combination of RRN3 and POLR1D; a correct classification rate of 83% is obtained using the combination of POLR1D and LRPPRC; and a correct classification rate of 90% is obtained using the combination of RRN3 and LRPPRC (Table 4C, above).

The classification for the combination of RRN3 and LRPPRC resulted in outstanding classification rate of 90% of typical RRMS (TMS) (Table 4C), while showing a low 30% classification for these 2 genes for BMS (Table 4B), further supporting the differentiations between the two disease patterns.

To conclude, correct classification for both groups would be achieved using more than one combination of genes of the RNA polymerase I pathway, for example LRPPRC alone or with POLR1D reached 80% classification rate for BMS and RRN3 and LRPPRC correctly classify 90% of TMS patients.

Identification of Biomarkers for Differentiation of Patients with BMS or Typical RRMS Course of Disease—
BMS patients differentiated from typical RRMS by 177 MIGs (Table 5). The 17 genes with higher classification performance (Table 6) were identified from MIGs by applying predictive algorithms.

TABLE 5

MIGs discriminating between BMS and typical RRMS patients

| Affymetrix ProbSet ID | SEQ NO ID: | Representative Public ID | SEQ ID NO: | p-value BMS vs typical RRMS | Log Fold Change (BMS vs typical RRMS) | Gene Symbol | Gene description |
|---|---|---|---|---|---|---|---|
| 216902_s_at | 62 | AF001549 | 468 | 2.12E−08 | −2.01 | RRN3 | RRN3 RNA polymerase I transcription factor homolog (yeast) |
| 210502_s_at | 1410 | AF042386 | 1534 | 2.30E−08 | −1.28 | PPIE | peptidylprolyl isomerase E (cyclophilin E) |
| 211615_s_at | 1418 | M92439 | 1512 | 2.44E−08 | −1.20 | LRPPRC | leucine-rich PPR-motif containing /// leucine-rich PPR-motif containing |
| 37950_at | 1500 | X74496 | 1526 | 1.05E−06 | 1.19 | PREP | prolyl endopeptidase |
| 218258_at | 173 | NM_015972 | 984 | 1.92E−06 | −1.18 | POLR1D | polymerase (RNA) I polypeptide D, 16 kDa |
| 214439_x_at | 1453 | AF043899 | 1535 | 2.24E−06 | −1.62 | BIN1 | bridging integrator 1 |
| 214450_at | 1454 | NM_001335 | 1629 | 3.82E−06 | −1.45 | CTSW | cathepsin W (lymphopain) /// cathepsin W (lymphopain) |
| 214470_at | 1455 | NM_002258 | 1615 | 3.83E−06 | −1.77 | KLRB1 | killer cell lectin-like receptor subfamily B, member 1 /// killer cell lectin-li |
| 205789_at | 1373 | NM_001766 | 1627 | 4.32E−06 | 1.62 | CD1D | CD1D antigen, d polypeptide /// CD1D antigen, d polypeptide |
| 206584_at | 1378 | NM_015364 | 1650 | 5.84E−06 | 1.59 | LY96 | lymphocyte antigen 96 |
| 212252_at | 1425 | AA181179 | 1660 | 6.14E−06 | 1.62 | CAMKK2 | calcium/calmodulin-dependent protein kinase kinase 2, beta |
| 212748_at | 1431 | AB037859 | 1583 | 7.92E−06 | 1.18 | MKL1 | megakaryoblastic leukemia (translocation) 1 |
| 211654_x_at | 1419 | M17565 | 1519 | 9.99E−06 | 2.75 | HLA-DQB1 | major histocompatibility complex, class II, DQ beta 1 /// major histocompatibili |
| 204860_s_at | 1370 | AI817801 | 1673 | 1.21E−05 | 1.62 | BIRC1 | baculoviral IAP repeat-containing 1 |
| 211971_s_at | 204 | AI653608 | 606 | 1.62E−05 | −1.14 | LRPPRC | leucine-rich PPR-motif containing |
| 202832_at | 1347 | NM_014635 | 1601 | 2.21E−05 | −1.33 | GCC2 | GRIP and coiled-coil domain containing 2 |
| 40446_at | 1502 | AL021366 | 1537 | 2.62E−05 | −1.39 | PHF1 | PHD finger protein 1 |
| 210136_at | 1404 | AW070431 | 1676 | 2.71E−05 | −1.76 | MBP | Myelin basic protein |
| 202441_at | 1342 | AL568449 | 1691 | 3.92E−05 | 1.37 | C10orf69 | chromosome 10 open reading frame 69 |
| 213241_at | 1442 | AF035307 | 1532 | 4.12E−05 | 1.55 | PLXNC1 | Plexin C1 |
| 212978_at | 1435 | AU146004 | 1686 | 4.13E−05 | 1.56 | TA-LRRP | T-cell activation leucine repeat-rich protein |
| 220005_at | 1490 | NM_023914 | 1591 | 4.55E−05 | 2.43 | P2RY13 | purinergic receptor P2Y, G-protein coupled, 13 /// purinergic receptor P2Y, G-pr |
| 218304_s_at | 1473 | NM_022776 | 1645 | 4.89E−05 | 1.58 | OSBPL11 | oxysterol binding protein-like 11 |
| 218932_at | 1480 | NM_017953 | 1652 | 5.00E−05 | −1.27 | FLJ20729 | hypothetical protein FLJ20729 |

TABLE 5-continued

MIGs discriminating between BMS and typical RRMS patients

| Affymetrix ProbSet ID | SEQ NO ID: | Representative Public ID | SEQ ID NO: | p-value BMS vs typical RRMS | Log Fold Change (BMS vs typical RRMS) | Gene Symbol | Gene description |
|---|---|---|---|---|---|---|---|
| 213106_at | 1440 | AI769688 | 1670 | 5.57E−05 | −1.51 | ATP8A1 | ATPase, aminophospholipid transporter (APLT), Class I, type 8A, member 1 |
| 219892_at | 1489 | NM_023003 | 1648 | 5.63E−05 | 1.86 | TM6SF1 | transmembrane 6 superfamily member 1 |
| 219666_at | 1486 | NM_022349 | 1585 | 6.07E−05 | 1.81 | MS4A6A | membrane spanning 4-domains, subfamily A, member 6A |
| 206120_at | 1376 | NM_001772 | 1631 | 6.26E−05 | 1.58 | CD33 | CD33 antigen (gp67) |
| 209970_x_at | 1403 | M87507 | 1523 | 6.51E−05 | 1.33 | CASP1 | caspase 1, apoptosis-related cysteine protease (interleukin 1, beta, convertase) |
| 200980_s_at | 1330 | NM_000284 | 1654 | 8.59E−05 | −1.27 | PDHA1 | pyruvate dehydrogenase (lipoamide) alpha 1 |
| 200610_s_at | 1326 | NM_005381 | 1613 | 8.97E−05 | −1.17 | NCL | nucleolin |
| 213418_at | 1445 | NM_002155 | 1609 | 8.99E−05 | 2.73 | HSPA6 | heat shock 70 kDa protein 6 (HSP70B') |
| 212421_at | 1429 | AB023147 | 1545 | 9.22E−05 | 1.66 | C22orf9 | chromosome 22 open reading frame 9 |
| 210201_x_at | 1407 | AF001383 | 1531 | 9.59E−05 | −1.59 | BIN1 | bridging integrator 1 |
| 207000_s_at | 1381 | NM_005605 | 1600 | 9.72E−05 | −1.32 | PPP3CC | protein phosphatase 3 (formerly 2B), catalytic subunit, gamma isoform (calcineur |
| 203139_at | 1352 | NM_004938 | 1623 | 0.000102879 | 1.78 | DAPK1 | death-associated protein kinase 1 |
| 211368_s_at | 1416 | U13700 | 1527 | 0.000107311 | 1.36 | CASP1 | caspase 1, apoptosis-related cysteine protease (interleukin 1, beta, convertase) |
| 212820_at | 1433 | AB020663 | 1582 | 0.000108529 | 1.70 | RC3 | rabconnectin-3 |
| 216945_x_at | 15 | U79240 | 421 | 0.000111457 | −1.86 | PASK | PAS domain containing serine/threonine kinase |
| 209337_at | 1395 | AF063020 | 1540 | 0.000112781 | −1.35 | PSIP1 | PC4 and SFRS1 interacting protein 1 |
| 201756_at | 1337 | NM_002946 | 1599 | 0.000114388 | −1.41 | RPA2 | replication protein A2, 32 kDa |
| 221565_s_at | 1493 | BC000039 | 1602 | 0.00011473 | 1.50 | FAM26B | family with sequence similarity 26, member B |
| 117_at | 1325 | X51757cds | #N/A | 0.000116998 | 2.01 | HSPA6 | heat shock 70 kDa protein 6 (HSP70B') |
| 43544_at | 1503 | AA314406 | 1661 | 0.000118986 | −1.65 | THRAP5 | thyroid hormone receptor associated protein 5 |
| 219132_at | 1483 | NM_021255 | 1621 | 0.000121966 | 1.36 | PELI2 | pellino homolog 2 (Drosophila) |
| 57715_at | 1507 | W72694 | 1657 | 0.000123909 | 1.35 | FAM26B | family with sequence similarity 26, member B |
| 220066_at | 1491 | NM_022162 | 1569 | 0.000125076 | 1.53 | CARD15 | caspase recruitment domain family, member 15 |
| 212414_s_at | 1428 | D50918 | 1528 | 0.000139145 | −1.53 | SEPT6 | septin 6 |
| 213902_at | 1448 | AI379338 | 1666 | 0.000139994 | 1.32 | ASAH1 | N-acylsphingosine amidohydrolase (acid ceramidase) 1 |
| 212998_x_at | 1436 | AI583173 | 1667 | 0.000143667 | 2.26 | HLA-DQB1 | major histocompatibility complex, class II, DQ beta 1 /// major histocompatibili |
| 202931_x_at | 1350 | NM_004305 | 1584 | 0.000148834 | −1.55 | BIN1 | bridging integrator 1 |
| 204112_s_at | 1361 | NM_006895 | 1619 | 0.00014954 | 1.81 | HNMT | histamine N-methyltransferase |
| 205467_at | 297 | NM_001230 | 850 | 0.000150498 | 1.44 | CASP10 | caspase 10, apoptosis related cysteine protease |

TABLE 5-continued

MIGs discriminating between BMS and typical RRMS patients

| Affymetrix ProbSet ID | SEQ NO ID: | Representative Public ID | SEQ ID NO: | p-value BMS vs typical RRMS | Log Fold Change (BMS vs typical RRMS) | Gene Symbol | Gene description |
|---|---|---|---|---|---|---|---|
| 209199_s_at | 1394 | N22468 | 1656 | 0.000157534 | 1.51 | MEF2C | MADS box transcription enhancer factor 2, polypeptide C (myocyte enhancer factor |
| 211676_s_at | 1421 | AF056979 | 1578 | 0.000157969 | 1.40 | IFNGR1 | interferon gamma receptor 1 /// interferon gamma receptor 1 |
| 203492_x_at | 1355 | AA918224 | 1664 | 0.000163582 | −1.22 | KIAA0092 | translokin |
| 211776_s_at | 1423 | BC006141 | 1577 | 0.000164075 | 3.18 | EPB41L3 | erythrocyte membrane protein band 4.1-like 3 /// erythrocyte membrane protein ba |
| 56919_at | 1505 | AI806628 | 1672 | 0.000173847 | 1.32 | KIAA1449 | WD repeat endosomal protein |
| 202521_at | 1344 | NM_006565 | 1616 | 0.0001784 | −1.14 | CTCF | CCCTC-binding factor (zinc finger protein) |
| 211727_s_at | 1422 | BC005895 | 1576 | 0.000179886 | −1.49 | COX11 | COX11 homolog, cytochrome c oxidase assembly protein (yeast) /// COX11 homolog, |
| 204222_s_at | 1363 | NM_006851 | 1628 | 0.00018487 | 1.54 | GLIPR1 | GLI pathogenesis-related 1 (glioma) |
| 204839_at | 1369 | NM_015918 | 1603 | 0.000185062 | −1.21 | POP5 | processing of precursor 5, ribonuclease P/MRP subunit (S. cerevisiae) |
| 39729_at | 1501 | L19185 | 1524 | 0.000185886 | −1.62 | PRDX2 | peroxiredoxin 2 |
| 221078_s_at | 1492 | NM_018084 | 1646 | 0.000188529 | 1.49 | KIAA1212 | KIAA1212 |
| 35156_at | 1499 | AL050297 | 1548 | 0.000196739 | −1.24 | LOC203069 | Hypothetical protein LOC203069 |
| 219630_at | 1485 | NM_005764 | 1606 | 0.000198793 | 1.94 | MAP17 | membrane-associated protein 17 |
| 202662_s_at | 1345 | NM_002223 | 1625 | 0.00020557 | 1.34 | ITPR2 | inositol 1,4,5-triphosphate receptor, type 2 |
| 210212_x_at | 1409 | BC002600 | 1571 | 0.000219441 | −1.27 | MTCP1 | mature T-cell proliferation 1 |
| 217925_s_at | 1471 | NM_022758 | 1610 | 0.000224904 | −1.21 | C6orf106 | chromosome 6 open reading frame 106 |
| 218739_at | 1477 | NM_016006 | 1643 | 0.000228499 | 1.75 | ABHD5 | abhydrolase domain containing 5 |
| 56197_at | 1504 | AI783924 | 1671 | 0.000231008 | −1.24 | PLSCR3 | phospholipid scramblase 3 |
| 208653_s_at | 1388 | AF263279 | 1561 | 0.00023174 | 1.46 | CD164 | CD164 antigen, sialomucin |
| 213292_s_at | 1444 | AA908770 | 1663 | 0.00023191 | 1.54 | SNX13 | sorting nexin 13 |
| 201194_at | 1331 | NM_003009 | 1608 | 0.000240228 | −1.36 | SEPW1 | selenoprotein W, 1 |
| 201619_at | 1336 | NM_006793 | 1596 | 0.000250445 | 1.27 | PRDX3 | peroxiredoxin 3 |
| 203569_s_at | 1356 | NM_003611 | 1640 | 0.000272476 | −1.45 | OFD1 | oral-facial-digital syndrome 1 |
| 213979_s_at | 1450 | BF984434 | 1689 | 0.00027541 | −3.22 | — | — |
| 203814_s_at | 1359 | NM_000904 | 1635 | 0.000281273 | 1.67 | NQO2 | NAD(P)H dehydrogenase, quinone 2 |
| 215118_s_at | 1462 | AW519168 | 1680 | 0.000302493 | −2.77 | MGC27165 | Hypothetical protein MGC27165 |
| 203624_at | 1357 | NM_005088 | 1607 | 0.000330513 | −1.38 | DXYS155E | DNA segment on chromosome X and Y (unique) 155 expressed sequence |
| 206999_at | 1380 | NM_001559 | 1588 | 0.000344019 | 2.07 | IL12RB2 | interleukin 12 receptor, beta 2 |
| 205842_s_at | 1374 | AF001362 | 1538 | 0.000351718 | 1.85 | JAK2 | Janus kinase 2 (a protein tyrosine kinase) |
| 210166_at | 1405 | AF051151 | 1536 | 0.000353968 | 1.63 | TLR5 | toll-like receptor 5 |
| 219714_s_at | 1487 | NM_018398 | 1612 | 0.000364622 | 2.39 | CACNA2D3 | calcium channel, voltage-dependent, alpha 2/delta 3 subunit |

TABLE 5-continued

MIGs discriminating between BMS and typical RRMS patients

| Affymetrix ProbSet ID | SEQ NO ID: | Representative Public ID | SEQ ID NO: | p-value BMS vs typical RRMS | Log Fold Change (BMS vs typical RRMS) | Gene Symbol | Gene description |
|---|---|---|---|---|---|---|---|
| 212311_at | 1426 | AA522514 | 1662 | 0.000370292 | −1.36 | KIAA0746 | KIAA0746 protein |
| 213830_at | 1447 | AW007751 | 1675 | 0.000370999 | −1.69 | TRD @ | T-cell receptor delta chain HE/801 /// T cell receptor delta locus |
| 213005_s_at | 1438 | D79994 | 1614 | 0.000376513 | 2.26 | ANKRD15 | ankyrin repeat domain 15 |
| 202944_at | 1351 | NM_000262 | 1639 | 0.000376931 | 1.68 | NAGA | N-acetylgalactosaminidase, alpha- |
| 206011_at | 1375 | AI719655 | 1668 | 0.000379898 | 1.49 | CASP1 | caspase 1, apoptosis-related cysteine protease (interleukin 1, beta, convertase) |
| 204332_s_at | 1365 | M64073 | 1516 | 0.000382893 | −1.22 | AGA | aspartylglucosaminidase |
| 215592_at | 1463 | AU147620 | 1687 | 0.000385413 | −1.91 | — | Transcribed locus, weakly similar to XP_375099.1 hypothetical protein LOC283585 |
| 201798_s_at | 378 | NM_013451 | 777 | 0.000387903 | 2.24 | FER1L3 | fer-1-like 3, myoferlin (C. elegans) |
| 212069_s_at | 1424 | AK026025 | 1566 | 0.000388281 | −1.17 | KIAA0515 | KIAA0515 |
| 206255_at | 1377 | NM_001715 | 1597 | 0.000395152 | −1.72 | BLK | B lymphoid tyrosine kinase |
| 221932_s_at | 1497 | AA133341 | 1658 | 0.000396589 | −1.42 | C14orf87 | chromosome 14 open reading frame 87 |
| 203246_s_at | 1353 | NM_006545 | 1611 | 0.000402598 | −1.33 | TUSC4 | tumor suppressor candidate 4 |
| 213534_s_at | 19 | D50925 | 425 | 0.000408073 | −1.73 | PASK | PAS domain containing serine/threonine kinase |
| 219045_at | 1481 | NM_019034 | 1604 | 0.000412198 | −1.33 | RHOF | ras homolog gene family, member F (in filopodia) |
| 202347_s_at | 1340 | AB022435 | 1550 | 0.000414497 | −1.16 | HIP2 | huntingtin interacting protein 2 |
| 212636_at | 1430 | AL031781 | 1543 | 0.000420707 | 1.61 | QKI | quaking homolog, KH domain RNA binding (mouse) |
| 202392_s_at | 1341 | NM_014338 | 1598 | 0.000423758 | 1.26 | PISD | phosphatidylserine decarboxylase |
| 216950_s_at | 1467 | X14355 | 1509 | 0.000437652 | 2.62 | FCGR1A | Fc fragment of IgG, high affinity Ia, receptor for (CD64) |
| 214511_x_at | 1457 | L03419 | 1515 | 0.000447516 | 2.83 | LOC440607 /// FCGR1A | Fc-gamma receptor I B2 /// Fc fragment of IgG, high affinity Ia, receptor for (C |
| 219316_s_at | 1484 | NM_017791 | 1641 | 0.000472922 | 1.68 | C14orf58 | chromosome 14 open reading frame 58 |
| 220122_at | 398 | NM_024717 | 797 | 0.000473634 | 3.36 | MCTP1 | multiple C2-domains with two transmembrane regions 1 |
| 64883_at | 1508 | AI744083 | 1669 | 0.000478581 | 1.51 | MOSPD2 | motile sperm domain containing 2 |
| 203279_at | 1354 | NM_014674 | 1644 | 0.000479669 | −1.24 | EDEM1 | ER degradation enhancer, mannosidase alpha-like 1 |
| 208891_at | 1390 | BC003143 | 1573 | 0.000483009 | 1.98 | DUSP6 | dual specificity phosphatase 6 |
| 205715_at | 1372 | NM_004334 | 1636 | 0.000490107 | 1.60 | BST1 | bone marrow stromal cell antigen 1 |
| 214085_x_at | 1451 | AI912583 | 1674 | 0.000510466 | 1.67 | HRB2 | HIV-1 rev binding protein 2 |
| 215000_s_at | 1461 | AL117593 | 1553 | 0.000515959 | 1.24 | FEZ2 | fasciculation and elongation protein zeta 2 (zygin II) |
| 202194_at | 1339 | AL117354 | 1556 | 0.000523169 | 1.36 | CGI-100 | CGI-100 protein |
| 210202_s_at | 1408 | U87558 | 1530 | 0.000532952 | −1.46 | BIN1 | bridging integrator 1 |
| 218181_s_at | 1472 | NM_017792 | 1560 | 0.000547382 | 1.13 | MAP4K4 | mitogen-activated protein kinase kinase kinase kinase 4 |

TABLE 5-continued

MIGs discriminating between BMS and typical RRMS patients

| Affymetrix ProbSet ID | SEQ NO ID: | Representative Public ID | SEQ ID NO: | p-value BMS vs typical RRMS | Log Fold Change (BMS vs typical RRMS) | Gene Symbol | Gene description |
|---|---|---|---|---|---|---|---|
| 204023_at | 1360 | NM_002916 | 1595 | 0.000553752 | −1.48 | RFC4 | replication factor C (activator 1) 4, 37 kDa |
| 207872_s_at | 1384 | NM_006863 | 1551 | 0.000561178 | 1.58 | LILRA1 | leukocyte immunoglobulin-like receptor, subfamily A (with TM domain), member 1 |
| 202878_s_at | 1349 | NM_012072 | 1622 | 0.000583921 | 1.42 | C1QR1 | complement component 1, q subcomponent, receptor 1 |
| 201285_at | 1333 | NM_013446 | 1649 | 0.000593976 | −1.21 | MKRN1 | makorin, ring finger protein, 1 /// makorin, ring finger protein, 1 |
| 211612_s_at | 1417 | U62858 | 1529 | 0.000613797 | 1.80 | IL13RA1 | interleukin 13 receptor, alpha 1 /// interleukin 13 receptor, alpha 1 |
| 219117_s_at | 1482 | NM_016594 | 1647 | 0.000616534 | −1.61 | FKBP11 | FK506 binding protein 11, 19 kDa |
| 215761_at | 1464 | AK000156 | 1557 | 0.000618215 | 2.26 | RC3 | rabconnectin-3 |
| 200800_s_at | 1328 | NM_005345 | 1642 | 0.000625103 | 1.65 | HSPA1A /// HSPA1B | heat shock 70 kDa protein 1A /// heat shock 70 kDa protein 1B |
| 202816_s_at | 1346 | AW292882 | 1679 | 0.000641212 | 1.44 | SS18 | synovial sarcoma translocation, chromosome 18 |
| 209440_at | 1397 | BC001605 | 1572 | 0.000646328 | −1.25 | PRPS1 | phosphoribosyl pyrophosphate synthetase 1 |
| 204221_x_at | 1362 | U16307 | 1587 | 0.000654803 | 1.51 | HRB2 | HIV-1 rev binding protein 2 |
| 57082_at | 1506 | AA169780 | 1659 | 0.000658787 | −1.41 | ARH | LDL receptor adaptor protein |
| 201887_at | 1338 | NM_001560 | 1589 | 0.000679598 | 1.52 | IL13RA1 | interleukin 13 receptor, alpha 1 |
| 215933_s_at | 1465 | Z21533 | 1510 | 0.000692626 | 1.47 | HHEX | hematopoietically expressed homeobox |
| 208774_at | 1389 | AV700224 | 1685 | 0.000699738 | 1.20 | CSNK1D | Casein kinase 1, delta |
| 201478_s_at | 1334 | U59151 | 1533 | 0.000707429 | −1.18 | DKC1 | dyskeratosis congenita 1, dyskerin |
| 208918_s_at | 1391 | AI334128 | 1665 | 0.000708781 | 1.38 | FLJ13052 | NAD kinase |
| 208158_s_at | 1386 | NM_018030 | 1581 | 0.000726407 | 1.37 | OSBPL1A | oxysterol binding protein-like 1A /// oxysterol binding protein-like 1A |
| 202838_at | 1348 | NM_000147 | 1651 | 0.00073801 | 1.43 | FUCA1 | fucosidase, alpha-L-1, tissue |
| 205039_s_at | 1371 | NM_006060 | 1633 | 0.000754874 | 2.05 | ZNFN1A1 | zinc finger protein, subfamily 1A, 1 (Ikaros) |
| 204834_at | 1368 | NM_006682 | 1626 | 0.000760238 | 1.74 | FGL2 | fibrinogen-like 2 |
| 200701_at | 1327 | NM_006432 | 1592 | 0.000763959 | 1.41 | NPC2 | Niemann-Pick disease, type C2 |
| 204254_s_at | 1364 | NM_000376 | 1617 | 0.00077458 | 1.64 | VDR | vitamin D (1,25-dihydroxyvitamin D3) receptor |
| 217922_at | 1470 | AL157902 | 1562 | 0.000779841 | −1.34 | MAN1A2 | Mannosidase, alpha, class 1A, member 2 |
| 218888_s_at | 1479 | NM_018092 | 1586 | 0.000801694 | 1.39 | NETO2 | neuropilin (NRP) and tolloid (TLL)-like 2 |
| 210947_s_at | 1414 | J04810 | 1514 | 0.000810544 | 1.30 | MSH3 | mutS homolog 3 (*E. coli*) |
| 208923_at | 1392 | BC005097 | 1575 | 0.000816109 | 1.41 | CYFIP1 | cytoplasmic FMR1 interacting protein 1 |
| 209429_x_at | 1396 | AF112207 | 1555 | 0.000818155 | −1.22 | — | — |
| 204566_at | 1366 | NM_003620 | 1593 | 0.000823091 | 1.67 | PPM1D | protein phosphatase 1D magnesium-dependent, delta isoform |
| 218854_at | 1478 | NM_013352 | 1630 | 0.000823847 | 1.47 | SART2 | squamous cell carcinoma antigen recognized by T cells 2 |

TABLE 5-continued

MIGs discriminating between BMS and typical RRMS patients

| Affymetrix ProbSet ID | SEQ NO ID: | Representative Public ID | SEQ ID NO: | p-value BMS vs typical RRMS | Log Fold Change (BMS vs typical RRMS) | Gene Symbol | Gene description |
|---|---|---|---|---|---|---|---|
| 213198_at | 1441 | AL117643 | 1554 | 0.000836 | 1.33 | ACVR1B | activin A receptor, type IB |
| 218642_s_at | 1476 | NM_024300 | 1618 | 0.000849263 | −1.21 | CHCHD7 | coiled-coil-helix-coiled-coil-helix domain containing 7 |
| 203645_s_at | 1358 | NM_004244 | 1632 | 0.000851877 | 1.60 | CD163 | CD163 antigen |
| 208117_s_at | 1385 | NM_031206 | 1653 | 0.000852389 | −1.32 | FLJ12525 | hypothetical protein FLJ12525 /// hypothetical protein FLJ12525 |
| 218519_at | 1474 | NM_017945 | 1594 | 0.000854014 | 1.30 | SLC35A5 | solute carrier family 35, member A5 |
| 217764_s_at | 1469 | AF183421 | 1563 | 0.000871159 | 1.30 | RAB31 | RAB31, member RAS oncogene family |
| 214765_s_at | 1459 | AK024677 | 1564 | 0.000919505 | 1.50 | ASAHL | N-acylsphingosine amidohydrolase (acid ceramidase)-like |
| 212799_at | 1432 | BE217875 | 1682 | 0.00093697 | 1.31 | — | Clone 23570 mRNA sequence |
| 204744_s_at | 1367 | NM_013417 | 1624 | 0.000961709 | −1.24 | IARS | isoleucine-tRNA synthetase |
| 218526_s_at | 1475 | NM_014185 | 1559 | 0.000964651 | −1.22 | RANGNRF | RAN guanine nucleotide release factor |
| 211139_s_at | 1415 | AF045452 | 1539 | 0.000972219 | 1.40 | NAB1 | NGFI-A binding protein 1 (EGR1 binding protein 1) |
| 213958_at | 1449 | AW134823 | 1677 | 0.000977101 | −1.39 | CD6 | CD6 antigen /// CD6 antigen |
| 221695_s_at | 1494 | AF239798 | 1558 | 0.000979214 | 1.37 | MAP3K2 | mitogen-activated protein kinase kinase kinase 2 /// mitogen-activated protein k |
| 210176_at | 1406 | AL050262 | 1549 | 0.000989413 | 1.62 | TLR1 | toll-like receptor 1 |
| 212314_at | 1427 | AB018289 | 1542 | 0.00099 | −1.34 | KIAA0746 | KIAA0746 protein |
| 209882_at | 1402 | AF084462 | 1544 | 0.000992617 | 1.42 | RIT1 | Ras-like without CAAX 1 |
| 214500_at | 1456 | AF044286 | 1541 | 0.00102256 | 1.51 | H2AFY | H2A histone family, member Y |
| 213088_s_at | 1439 | BE551340 | 1684 | 0.00104481 | −1.17 | DNAJC9 | DnaJ (Hsp40) homolog, subfamily C, member 9 |
| 200821_at | 1329 | NM_013995 | 1638 | 0.00104551 | 1.22 | LAMP2 | lysosomal-associated membrane protein 2 |
| 210732_s_at | 1411 | AF342816 | 1574 | 0.00106818 | 1.84 | LGALS8 | lectin, galactoside-binding, soluble, 8 (galectin 8) |
| 201224_s_at | 1332 | AU147713 | 1688 | 0.00107129 | −1.23 | SRRM1 | serine/arginine repetitive matrix 1 |
| 202444_s_at | 1343 | NM_006459 | 1634 | 0.00107236 | 1.72 | C10orf69 | chromosome 10 open reading frame 69 |
| 206707_x_at | 1379 | NM_015864 | 1580 | 0.00107472 | −1.24 | C6orf32 | chromosome 6 open reading frame 32 |
| 221839_s_at | 1496 | AK026088 | 1567 | 0.00107916 | −1.34 | UBAP2 | ubiquitin associated protein 2 |
| 213279_at | 1443 | AL050217 | 1547 | 0.00108194 | 1.21 | DHRS1 | dehydrogenase/reductase (SDR family) member 1 |
| 214974_x_at | 1460 | AK026546 | 1568 | 0.00109223 | 2.67 | CXCL5 | chemokine (C—X—C motif) ligand 5 |
| 209583_s_at | 1399 | AF063591 | 1570 | 0.00109644 | 1.65 | CD200 | CD200 antigen |
| 209870_s_at | 1401 | AW571582 | 1681 | 0.00112322 | −1.39 | APBA2 | amyloid beta (A4) precursor protein-binding, family A, member 2 (X11-like) |
| 201494_at | 1335 | NM_005040 | 1605 | 0.0011371 | 1.27 | PRCP | prolylcarboxypeptidase (angiotensinase C) |
| 219806_s_at | 1488 | NM_020179 | 1637 | 0.00113985 | 1.36 | FN5 | FN5 protein |
| 208651_x_at | 1387 | M58664 | 1513 | 0.00119019 | −1.38 | CD24 | CD24 antigen (small cell lung carcinoma cluster 4 antigen) |

TABLE 5-continued

MIGs discriminating between BMS and typical RRMS patients

| Affymetrix ProbSet ID | SEQ NO ID: | Representative Public ID | SEQ ID NO: | p-value BMS vs typical RRMS | Log Fold Change (BMS vs typical RRMS) | Gene Symbol | Gene description |
|---|---|---|---|---|---|---|---|
| 216191_s_at | 1466 | X72501 | 1522 | 0.00132593 | −1.84 | TRDD3 /// TRD @ | T cell receptor delta diversity 3 /// T cell receptor delta locus |
| 217143_s_at | 1468 | X06557 | 1511 | 0.00187286 | −1.83 | TRDD3 /// TRD @ | T cell receptor delta diversity 3 /// T cell receptor delta locus | vs. = versus.

TABLE 6

Genes which when included in classifiers of no more than 10 genes exhibit at least 70% correct classification rates between BMS and typical RRMS patients

| Probeset ID | SEQ ID NO: | Gene Symbol | P value (min) | BMS vs RRMS | Sequence Derived From | SEQ ID NO: | Gene Title | Full Length Ref. Sequences | SEQ ID NO: |
|---|---|---|---|---|---|---|---|---|---|
| 222204_s_at | 1498 | RRN3 | $2.1 * 10^{-8}$ | (−) | AL110238 | 1552 | RNA polymerase I transcription factor RRN3 | NM_018427 | 1010 |
| 221714_s_at | 1495 | LOC94431 | | | BC006441 | 1579 | similar to RNA polymerase I transcription factor RRN3 | NM_145237 | 1156 |
| 211615_s_at | 1418 | LRPPRC | $2.4 * 10^{-8}$ | (−) | M92439 | 1512 | leucine-rich PPR-motif containing protein | NM_133259 | 1065 |
| 211971_s_at | 204 | LRPPRC | | | AI653608 | 606 | leucine-rich PPR motif containing protein | NM_133259 | 1065 |
| 218258_at | 173 | POLR1D | $1.9 * 10^{-6}$ | (−) | NM_015972 | 984 | hypothetical protein MGC9850 | NM_152705 | 1695 |
| 205789_at | 1373 | CD1D | $4.3 * 10^{-6}$ | (+) | NM_001766 | 1627 | CD1D antigen, d polypeptide | NM_001766 | 1627 |
| 212999_x_at | 1437 | HLA-DQB1 | $9.9 * 10^{-6}$ | (+) | AW276186 | 1678 | major histocompatibility complex, class II, DQ beta 1 precursor | NM_002123 | 1699 |
| 209823_x_at | 1400 | HLA-DQB1 | | | M17955 | 1518 | major histocompatibility complex, class II, DQ beta 1 precursor | NM_002123 | 1699 |
| 209480_at | 1398 | HLA-DQB1 | | | M16276 | 1521 | major histocompatibility complex, class II, DQ beta 1 precursor | NM_002123 | 1699 |
| 211656_x_at | 1420 | HLA-DQB1 | | | M32577 | 1520 | major histocompatibility complex, class II, DQ beta 1 precursor | NM_002123 | 1699 |
| 211654_x_at | 1419 | HLA-DQB1 | | | M17565 | 1519 | major histocompatibility complex, class II, DQ beta 1 precursor | NM_002123 | 1699 |
| 210747_at | 1412 | HLA-DQB1 | | | M24364 | 1525 | major histocompatibility complex, class II, DQ beta 1 precursor | NM_002123 | 1699 |

TABLE 6-continued

Genes which when included in classifiers of no more than 10 genes exhibit at least 70% correct classification rates between BMS and typical RRMS patients

| Probeset ID | SEQ ID NO: | Gene Symbol | P value (min) | BMS vs RRMS | Sequence Derived From | SEQ ID NO: | Gene Title | Full Length Ref. Sequences | SEQ ID NO: |
|---|---|---|---|---|---|---|---|---|---|
| 206584_at | 1378 | LY96 | 5.8 * 10−6 | (+) | NM_015364 | 1650 | lymphocyte antigen 96; // MD-2 protein | NM_015364 | 1650 |
| 207359_at | 1383 | CAMKK2 | 6.1 * 10−6 | (+) | NM_006549 | 1590 | calcium/calmodulin-dependent protein kinase kinase 2, beta isoform 1 | NM_006549 | 1590 |
| 214209_s_at | 1452 | CAMKK2 | | | BE504895 | 1683 | calcium/calmodulin-dependent protein kinase kinase 2, beta isoform 1 | NM_006549 | 1590 |
| 213812_s_at | 1446 | CAMKK2 | | | AK024748 | 1565 | calcium/calmodulin-dependent protein kinase kinase 2, beta isoform 1 | NM_006549 | 1590 |
| 210787_s_at | 1413 | CAMKK2 | | | AF140507 | 1546 | calcium/calmodulin-dependent protein kinase kinase 2, beta isoform 1 | NM_006549 | 1590 |
| 212252_at | 1425 | CAMKK2 | | | AA181179 | 1660 | calcium/calmodulin-dependent protein kinase kinase 2, beta isoform 1 | NM_006549 | 1590 |
| 214643_x_at | 1458 | BIN1 | 2.2 * 10−6 | (−) | BG034080 | 1690 | bridging integrator 1 isoform 8 | NM_004305 // NM_139343 | 1693 //1694 |
| 210202_s_at | 1408 | BIN1 | | | U87558 | 1530 | bridging integrator 1 isoform 8 | NM_004305 // NM_139343 // | 1693 //1694 |
| 214439_x_at | 1453 | BIN1 | | | AF043899 | 1535 | bridging integrator 1 isoform 8 | NM_004305 // NM_139343 // | 1693 //1694 |
| 202931_x_at | 1350 | BIN1 | | | NM_004305 | 1584 | bridging integrator 1 isoform 8 | NM_004305 // NM_139343 // | 1693 //1694 |
| 210201_x_at | 1407 | BIN1 | | | AF001383 | 1531 | bridging integrator 1 isoform 8 | NM_004305 // NM_139343 // | 1693 //1694 |
| 214450_at | 1454 | CTSW | 3.8 * 10−6 | (−) | NM_001335 | 1629 | cathepsin W preproprotein | NM_001335 | 1629 |
| 214470_at | 1455 | KLRB1 | 3.8 * 10−6 | (−) | NM_002258 | 1615 | killer cell lectin-like receptor subfamily B, member 1 | NM_002258 | 1615 |
| 212748_at | 1431 | MKL1 | 7.9 * 10−9 | (+) | AB037859 | 1583 | megakaryoblastic leukemia (translocation) 1 | NM_020831 | 1696 |
| 209072_at | 1393 | MBP | 2.7 * 10−5 | (−) | M13577 | 1517 | myelin basic protein | NM_002385 | 1620 |
| 210136_at | 1404 | MBP | | | AW070431 | 1676 | myelin basic protein | NM_002385 | 1620 |
| 207323_s_at | 1382 | MBP | | | NM_002385 | 1620 | myelin basic protein | NM_002385 | 1620 |
| 212978_at | 1435 | TA-LRRP | 4.1 * 10−5 | (+) | AU146004 | 1686 | T-cell activation leucine repeat-rich protein | NM_015350 | 1700 |
| 212976_at | 1434 | TA-LRRP | | | R41498 | 1655 | T-cell activation leucine repeat-rich protein | NM_015350 | 1700 |
| 117_at | 1325 | HSPA6 | 8.9 * 10−5 | (+) | X51757 | 1692 | heat shock 70 kDa protein 6 (HSP70B') | NM_002155 | 1609 |

TABLE 6-continued

Genes which when included in classifiers of no more than 10 genes exhibit at least 70% correct classification rates between BMS and typical RRMS patients

| Probeset ID | SEQ ID NO: | Gene Symbol | P value (min) | BMS vs RRMS | Sequence Derived From | SEQ ID NO: | Gene Title | Full Length Ref. Sequences | SEQ ID NO: |
|---|---|---|---|---|---|---|---|---|---|
| 213418_at | 1445 | HSPA6 | | | NM_002155 | 1609 | heat shock 70 kDa protein 6 (HSP70B') | NM_002155 | 1609 |
| 200610_s_at | 1326 | NCL | 8.9 * 10−5 | (−) | NM_005381 | 1613 | nucleolin | NM_005381 | 1613 |
| 216191_s_at | 1466 | TRD @ | 3.7 * 10−4 | (−) | X72501 | 1522 | T cell receptor delta locus | — | #N/A |
| 217143_s_at | 1468 | TRD @ | | | X06557 | 1511 | T cell receptor delta locus | — | #N/A |
| 213830_at | 1447 | TRD @ | | | AW007751 | 1675 | T cell receptor delta locus | — | #N/A |
| 213005_s_at | 1438 | KANK | 3.7 * 10−4 | (+) | D79994 | 1614 | kidney ankyrin repeat-containing protein | NM_015158 // NM_153186 | 1698 //1697 |

Presented are 38 gene transcripts which correspond for 17 human genes which classify BMS and typical RRMS patients.
Genes given by the gene name and description, the Affymetrix probeset identification number, and a representative GenBank Accession numbers.
The (−) sign means that the polynucleotide is downregulated (decreased in level) in BMS as compared to typical RRMS subjects;
and the (+) sign means that the polynucleotide is upregulated (increased in level) in BMS as compared to RRMS subjects.

Examples of classifiers are presented as following: NCL, MKL1, CTSW, KLRB1 and LRPPRC which results in correct classification rate of 79% of BMS and typical RRMS; and NCL, MKL1, CTSW, KLRB1, POLR1D, CD1D, and CAMKK2 which results in correct classification rate of 77% of BMS and typical RRMS.

Example 3

Testing the Effect of an Anti MS Drug in Experimental Allergic Encephalomyelitis (EAE)—Animal MS Model Animal Model for Multiple Sclerosis—

EAE is induced in female Lewis rats (N=15; 6-8 weeks old, body weight 180-200 g) by hind footpad subcutaneous inoculation with emulsion of 25 mg guinea-pig MBP (myelin basic protein) in CFA containing 40 mg of *Mycobacterium tuberculosis* (Difco, Detroit, Mich.) in 0.1 ml oil. Control rats (N=15) are injected with the same emulsion where saline solution replaces MBP. The EAE is scored as follows: 0—No obvious changes in motor function on of the rats in comparison to non-immunized rats; 1—Limp tail; 2—Limp tail and weakness of hind legs; 3—Limp tail and complete paralysis of hind legs, or limp tail with paralysis of one front and one hind leg. Or all of: walking only along the edges of the cage, pushing against the cage wall, pushing against the cage wall, spinning when picked up by the tail; 4—Limp tail, complete hind leg and partial front leg paralysis; 5—Complete hind and complete front leg paralysis, no movement around the cage, or mouse is spontaneously rolling in the cage, mouse is found dead due to paralysis.

Treatment with an Anti MS Drug or with an Agent which Downregulates at Least One Gene of the RNA Polymerase Pathway—

A therapeutically effective amount of a drug or an agent which downregulates the expression level of a gene involved in the RNA polymerase I pathway (e.g., TPT) is administered to the animal on the day of EAE induction and blood samples are drawn before and after treatment, at predetermined time points which include baseline=Time 0, Day 12—peak disease, Day 17 and day 21.

Testing the Level of Expression of Genes Involved in the RNA Polymerase I Pathway—

Blood samples, obtained from the control and treated animals, are tested using Q-RT-PCR for bio-markers of benign multiple sclerosis (e.g., $RRN_3$, $POLR_1D$ and LRPPRC). Control animals are compared to animals on the peak of EAE disease and to animals treated by the anti MS drug (e.g., TPT).

Example 4

In Vitro Testing Efficacy of a Drug In Vitro Using Cells of a Multiple Sclerosis Subject Peripheral blood samples are obtained from female subjects with typical RRMS disease course. All patients are free of immunomodulatory or corticosteroid treatments at least 30 days before blood withdrawal. PBMC are extracted from peripheral blood, separated by Ficoll-Hypaque gradient. 15 ml of peripheral blood from patients is diluted 1:1 with Phosphate Buffered Saline (PBS) (without $Ca^{2+}/Mg^{2+}$). Blood samples are underlied with 10 ml of Ficoll-Lymphoprep (Axis Chield, Norway) and spinned (Eppendorf centrifuge, Germany) at 2300 RPM for 30 minutes. PBMCs are collected, washed with PBS and counted and incubated at 37° C. in a humidified $CO_2$ incubator with or without anti MS drugs. After incubation, total RNA is extracted using both Trizol (Invitrogen, USA) and Phase-Lock-Gel columns (Eppendorf, Germany) including a DNase digestion step. RNA integrity is assessed by RNA Experion automated electrophoresis system.

Treatment with an Anti MS Drug or with an Agent which Downregulates at Least One Gene of the RNA Polymerase Pathway—

A therapeutically effective amount of a drug or an agent which downregulates the expression level of a gene involved in the RNA polymerase I pathway (e.g., TPT) is incubated during 3 hours with the PBMC (of the subject having typical RRMS) and compared with PBMC (of the subject having typical RRMS) incubated during 3 hours without drug or with placebo excluding therapeutic component.

Testing the Level of Expression of Genes Involved in the RNA Polymerase I Pathway—

Total RNA samples, obtained from PBMC of a subject having typical RRMS trayed in-vitro with anti-RNA polymerase I agents (e.g. TPT), are tested using Q-RT-PCR for bio-markers of benign multiple sclerosis (e.g., $RRN_3$, $POLR_1D$ and LRPPRC). The results compared with PBMC from same patients incubated without drag or with placebo.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Hirschler-Laszkiewicz I, Cavanaugh A H, Mirza A et al. Rrn3 becomes inactivated in the process of ribosomal DNA transcription. J Biol Chem. 2003; 278:18953-18959;
2. Miller G, Panov K I, Friedrich J K et al. hRRN3 is essential in the SL1-mediated recruitment of RNA Polymerase I to rRNA gene promoters. Embo J. 2001; 20:1373-1382;
3. Achiron A, Gurevich M, Snir Y et al Zinc-ion binding and cytokine activity regulation pathways predicts outcome in relapsing-remitting multiple sclerosis. Clin Exp Immunol. 2007; 149:235-242;
4. Mootha V K, Lepage P, Miller K et al. Identification of a gene causing human cytochrome c oxidase deficiency by integrative genomics. Proc Natl Acad Sci USA. 2003; 100:605-610;
5. Bouwmeester T, Bauch A, Ruffner H et al. A physical and functional map of the human TNF-alpha/NF-kappa B signal transduction pathway. Nat Cell Biol. 2004; 6:97-105;
6. Leuenroth S J, Crews C M. Triptolide-induced transcriptional arrest is associated with changes in nuclear substructure. Cancer Res. 2008; 68:5257-5266;
7. Liu Y, Chen Y, Lamb J R, Tam P K. Triptolide, a component of Chinese herbal medicine, modulates the functional phenotype of dendritic cells. Transplantation. 2007; 84:1517-1526;
8. Wang Y, Mei Y, Feng D, Xu L. Triptolide modulates T-cell inflammatory responses and ameliorates experimental autoimmune encephalomyelitis. J Neurosci Res. 2008; 86:2441-2449;
9. Pittock S J, Rodriguez M. Benign multiple sclerosis: a distinct clinical entity with therapeutic implications. Curr Top Microbiol Immunol. 2008; 318:1-17;
10. L Costelloe, A Thompson, C Walsh, N Tubridy, and M Hutchinson Long-term clinical relevance of criteria for designating multiple sclerosis as benign after 10 years of disease J. Neurol. Neurosurg. Psychiatry, November 2008; 79: 1245-1248.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09758831B2). An electronic copy of the "Sequence Listing" will also be available from the USPTO upon request and payment of the fee set forth in 37 CFR 1.19(b)(3).

What is claimed is:

1. A composition comprising a probeset for classifying a disease course in a subject diagnosed with multiple sclerosis comprising a plurality of oligonucleotides and no more than 50 oligonucleotides, wherein said plurality of oligonucleotides comprise oligonucleotides that specifically recognize RRN3, POLR1D and LRPPRC; and a biological sample of a subject diagnosed with multiple sclerosis.

2. The composition of claim 1, wherein said biological sample comprises a blood sample.

3. The composition of claim 1, wherein said plurality of oligonucleotides comprises no more than 25 oligonucleotides.

4. The composition of claim 1, wherein said classifying a disease course comprises distinguishing between benign multiple sclerosis (BMS) and relapsing-remitting multiple sclerosis (RRMS).

* * * * *